United States Patent
Talbert et al.

(10) Patent No.: US 11,213,194 B2
(45) Date of Patent: Jan. 4, 2022

(54) OPTICAL FIBER WAVEGUIDE IN AN ENDOSCOPIC SYSTEM FOR HYPERSPECTRAL, FLUORESCENCE, AND LASER MAPPING IMAGING

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International

( * ) Notice: Subject to any disclaimer, the term of this patent is extended or adjusted under 35 U.S.C. 154(b) by 0 days.

(21) Appl. No.: 16/859,832

(22) Filed: Apr. 27, 2020

(65) Prior Publication Data

US 2020/0397271 A1    Dec. 24, 2020

Related U.S. Application Data

(60) Provisional application No. 62/864,281, filed on Jun. 20, 2019.

(51) Int. Cl.
| | |
|---|---|
| *A61B 1/07* | (2006.01) |
| *H04N 7/18* | (2006.01) |
| *A61B 1/00* | (2006.01) |
| *A61B 1/05* | (2006.01) |
| *A61B 1/045* | (2006.01) |

(Continued)

(52) U.S. Cl.
CPC ............ *A61B 1/07* (2013.01); *A61B 1/00006* (2013.01); *A61B 1/043* (2013.01); *A61B 1/045* (2013.01); *A61B 1/05* (2013.01); *A61B 1/051* (2013.01); *A61B 1/063* (2013.01); *A61B 1/0638* (2013.01); *A61B 1/0669* (2013.01); *G02B 6/0006* (2013.01); *G02B 6/0008* (2013.01); *G02B 6/04* (2013.01); *G06T 7/0012* (2013.01); *H04N 5/2253* (2013.01); *H04N 5/2256* (2013.01);

(Continued)

(58) Field of Classification Search
CPC ....... A61B 5/0071; A61B 5/20; A61B 5/4893; A61B 5/7203; A61B 5/489; A61B 5/0261; A61B 5/725; A61B 2560/0223; A61B 2576/00; H04N 5/2352; H04N 2005/2255

See application file for complete search history.

(56) References Cited

U.S. PATENT DOCUMENTS

| | | |
|---|---|---|
| 5,318,024 A | 6/1994 | Kittrell et al. |
| 5,363,387 A | 11/1994 | Sinofsky |

(Continued)

FOREIGN PATENT DOCUMENTS

| | | |
|---|---|---|
| CN | 111526775 A | 8/2020 |
| CN | 111565620 A | 8/2020 |

(Continued)

*Primary Examiner* — Nasim N Nirjhar
(74) *Attorney, Agent, or Firm* — Terrence J. Edwards; TechLaw Ventures, PLLC

(57) ABSTRACT

Optical fiber waveguide for communicating electromagnetic radiation pulsed by an emitter in an endoscopic imaging system. A system includes an emitter for emitting pulses of electromagnetic radiation and an endoscope comprising an image sensor for sensing reflected electromagnetic radiation. The system includes a waveguide communicating the pulses of electromagnetic radiation from the emitter to the endoscope. The system is such that at least a portion of the pulses of electromagnetic radiation emitted by the emitter comprises one or more of a hyperspectral emission, a fluorescence emission, and/or a laser mapping pattern.

32 Claims, 28 Drawing Sheets

(51) Int. Cl.
    *A61B 1/06*           (2006.01)
    *A61B 1/04*           (2006.01)
    *H04N 5/225*         (2006.01)
    *G06T 7/00*           (2017.01)
    *F21V 8/00*           (2006.01)
    *G02B 6/04*           (2006.01)
    *H04N 5/235*         (2006.01)
    *A61B 5/026*         (2006.01)
    *A61B 1/307*         (2006.01)
    *A61B 5/00*           (2006.01)

(52) U.S. Cl.
    CPC ............ *H04N 5/2353* (2013.01); *H04N 7/18* (2013.01); *A61B 1/0005* (2013.01); *A61B 1/00009* (2013.01); *A61B 1/0646* (2013.01); *A61B 1/307* (2013.01); *A61B 5/0261* (2013.01); *A61B 5/489* (2013.01); *A61B 5/4887* (2013.01); *A61B 5/4893* (2013.01); *G06T 2207/10064* (2013.01); *G06T 2207/10068* (2013.01); *G06T 2207/20221* (2013.01); *G06T 2207/30004* (2013.01); *H04N 2005/2255* (2013.01)

(56) References Cited

U.S. PATENT DOCUMENTS

| | | | |
|---|---|---|---|
| 5,749,830 A | 5/1998 | Kaneko et al. | |
| 6,110,106 A | 8/2000 | MacKinnon et al. | |
| 6,236,879 B1 | 5/2001 | Konings | |
| 6,291,824 B1* | 9/2001 | Battarbee | A61B 5/0073 250/330 |
| 6,975,898 B2 | 12/2005 | Seibel | |
| 8,537,203 B2 | 9/2013 | Seibel et al. | |
| 8,602,971 B2 | 12/2013 | Farr | |
| 9,509,917 B2 | 11/2016 | Blanquart et al. | |
| 9,547,165 B2 | 1/2017 | Yang et al. | |
| 9,839,365 B1 | 12/2017 | Homyl et al. | |
| 10,277,875 B2 | 4/2019 | Blanquart et al. | |
| 10,568,496 B2 | 2/2020 | Blanquart et al. | |
| 2001/0000317 A1 | 4/2001 | Yoneya et al. | |
| 2002/0123666 A1 | 9/2002 | Matsumoto | |
| 2002/0161282 A1 | 10/2002 | Fulghum | |
| 2003/0100824 A1 | 5/2003 | Warren et al. | |
| 2003/0109860 A1* | 6/2003 | Black | A61B 18/20 606/10 |
| 2004/0007675 A1* | 1/2004 | Gillispie | G01N 21/6408 250/458.1 |
| 2004/0186351 A1 | 9/2004 | Imaizumi et al. | |
| 2004/0234152 A1 | 11/2004 | Liege et al. | |
| 2005/0020926 A1 | 1/2005 | Wiklof et al. | |
| 2005/0107808 A1 | 5/2005 | Evans et al. | |
| 2006/0069314 A1 | 3/2006 | Farr | |
| 2006/0239723 A1 | 10/2006 | Okuda et al. | |
| 2006/0276966 A1 | 12/2006 | Cotton et al. | |
| 2007/0016077 A1 | 1/2007 | Nakaoka et al. | |
| 2007/0046778 A1 | 3/2007 | Ishihara et al. | |
| 2007/0086495 A1 | 4/2007 | Sprague et al. | |
| 2007/0242330 A1 | 10/2007 | Rosman et al. | |
| 2007/0276234 A1 | 11/2007 | Shahidi | |
| 2008/0077200 A1* | 3/2008 | Bendett | A61N 5/0618 607/89 |
| 2008/0081950 A1 | 4/2008 | Koenig et al. | |
| 2008/0177139 A1 | 7/2008 | Courtney et al. | |
| 2009/0306478 A1 | 12/2009 | Mizuyoshi | |
| 2009/0312607 A1* | 12/2009 | Sunagawa | A61B 5/0071 600/160 |
| 2010/0049180 A1 | 2/2010 | Wells et al. | |
| 2010/0056928 A1* | 3/2010 | Zak | A61B 5/0071 600/476 |
| 2010/0128109 A1 | 5/2010 | Banks | |
| 2010/0261958 A1 | 10/2010 | Webb et al. | |
| 2010/0277087 A1 | 11/2010 | Ikeda | |
| 2011/0087212 A1 | 4/2011 | Aldridge et al. | |
| 2011/0152619 A1* | 6/2011 | Hixon | G02B 6/32 600/135 |
| 2011/0196355 A1 | 8/2011 | Mitchell et al. | |
| 2011/0237942 A1* | 9/2011 | Zako | A61B 5/0077 600/431 |
| 2012/0071867 A1 | 3/2012 | Ryan et al. | |
| 2012/0123205 A1 | 5/2012 | Nie et al. | |
| 2012/0294498 A1 | 11/2012 | Popovic | |
| 2013/0176395 A1 | 7/2013 | Kazakevich | |
| 2013/0338436 A1* | 12/2013 | Dresher | A61B 1/00165 600/109 |
| 2014/0005555 A1* | 1/2014 | Tesar | A61B 17/0293 600/476 |
| 2014/0052004 A1 | 2/2014 | D'Alfonso et al. | |
| 2014/0111623 A1 | 4/2014 | Zhao et al. | |
| 2014/0160259 A1 | 6/2014 | Blanquart et al. | |
| 2014/0163319 A1* | 6/2014 | Blanquart | H04N 5/361 600/109 |
| 2014/0300750 A1 | 10/2014 | Nagamune | |
| 2014/0336501 A1 | 11/2014 | Matsumoto | |
| 2015/0044751 A1* | 2/2015 | Chiou | C12M 41/00 435/173.6 |
| 2015/0073209 A1 | 3/2015 | Ikeda | |
| 2015/0116513 A1 | 4/2015 | Chen et al. | |
| 2015/0216398 A1* | 8/2015 | Yang | G01J 3/0208 600/109 |
| 2015/0223733 A1 | 8/2015 | Al-Alusi | |
| 2015/0309284 A1 | 10/2015 | Kagawa et al. | |
| 2016/0006914 A1 | 1/2016 | Neumann | |
| 2016/0042513 A1 | 2/2016 | Yudovsky | |
| 2016/0062103 A1 | 3/2016 | Yang et al. | |
| 2016/0157725 A1* | 6/2016 | Munoz | H04N 5/33 600/430 |
| 2016/0183775 A1 | 6/2016 | Blanquart et al. | |
| 2016/0195706 A1 | 7/2016 | Fujii | |
| 2017/0055817 A1* | 3/2017 | Dybiec | A61B 1/00096 |
| 2017/0112370 A1* | 4/2017 | Daidoji | G02B 23/2461 |
| 2017/0209050 A1 | 7/2017 | Fengler et al. | |
| 2017/0280029 A1 | 9/2017 | Steiner | |
| 2017/0360275 A1 | 12/2017 | Yoshizaki | |
| 2018/0177387 A1 | 6/2018 | Talbert et al. | |
| 2018/0183981 A1 | 6/2018 | Talbert et al. | |
| 2019/0149713 A1 | 5/2019 | Blanquart et al. | |
| 2019/0191974 A1 | 6/2019 | Talbert et al. | |
| 2019/0191975 A1 | 6/2019 | Talbert et al. | |
| 2019/0191976 A1 | 6/2019 | Talbert et al. | |
| 2019/0191977 A1 | 6/2019 | Talbert et al. | |
| 2019/0191978 A1 | 6/2019 | Talbert et al. | |
| 2019/0197712 A1 | 6/2019 | Talbert et al. | |
| 2020/0329952 A1* | 10/2020 | Kiedrowski | G02B 23/2476 |
| 2020/0397260 A1 | 12/2020 | Talbert et al. | |
| 2020/0397261 A1 | 12/2020 | Talbert et al. | |
| 2020/0397262 A1 | 12/2020 | Talbert et al. | |
| 2020/0397265 A1 | 12/2020 | Talbert et al. | |
| 2020/0397270 A1 | 12/2020 | Talbert et al. | |

FOREIGN PATENT DOCUMENTS

| | | |
|---|---|---|
| CN | 111601536 A | 8/2020 |
| WO | 2015077493 A1 | 5/2015 |
| WO | 2017201093 A1 | 11/2017 |
| WO | 2018049215 A1 | 3/2018 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |
| WO | 2020257695 A1 | 12/2020 |
| WO | 2020257696 A1 | 12/2020 |
| WO | 2020257697 A1 | 12/2020 |
| WO | 2020257698 A1 | 12/2020 |
| WO | 2020257699 A1 | 12/2020 |

* cited by examiner

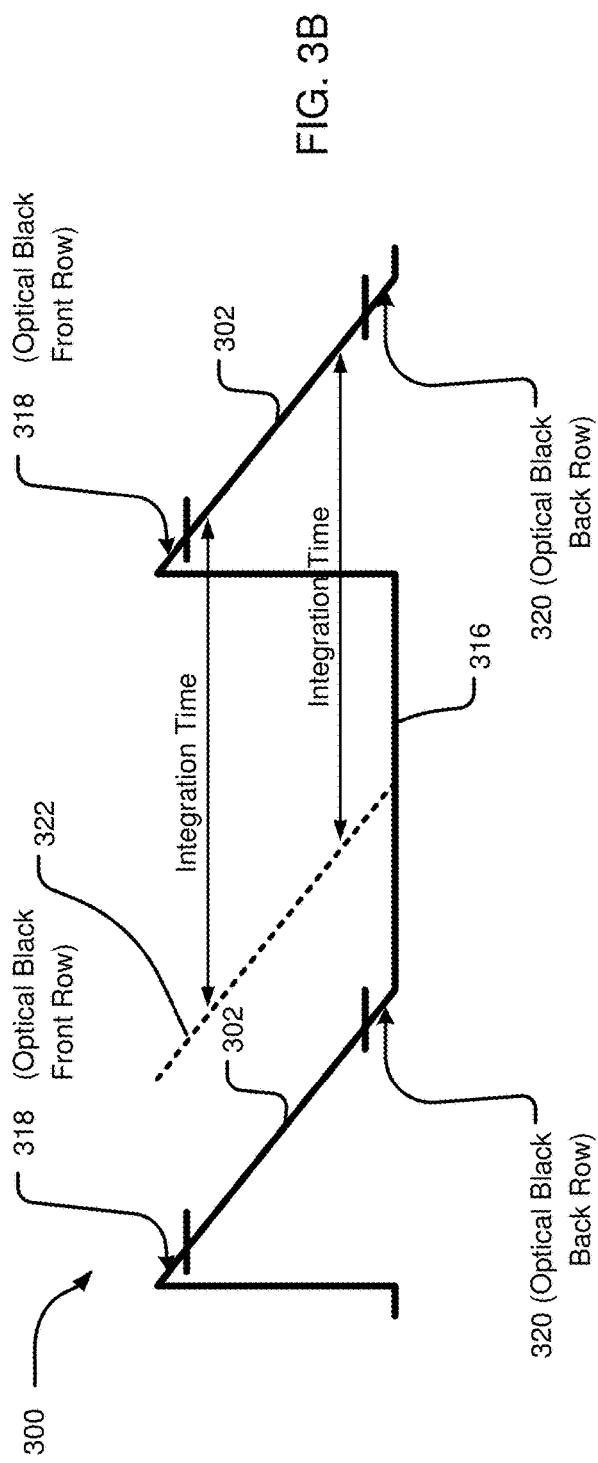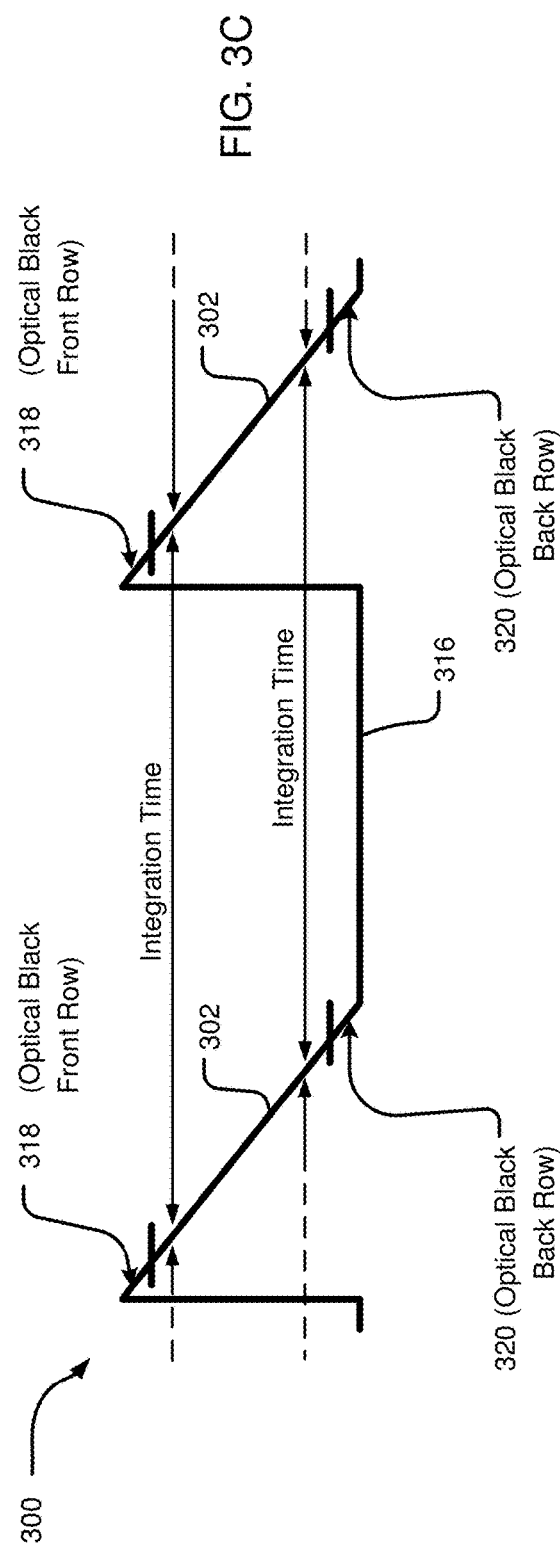

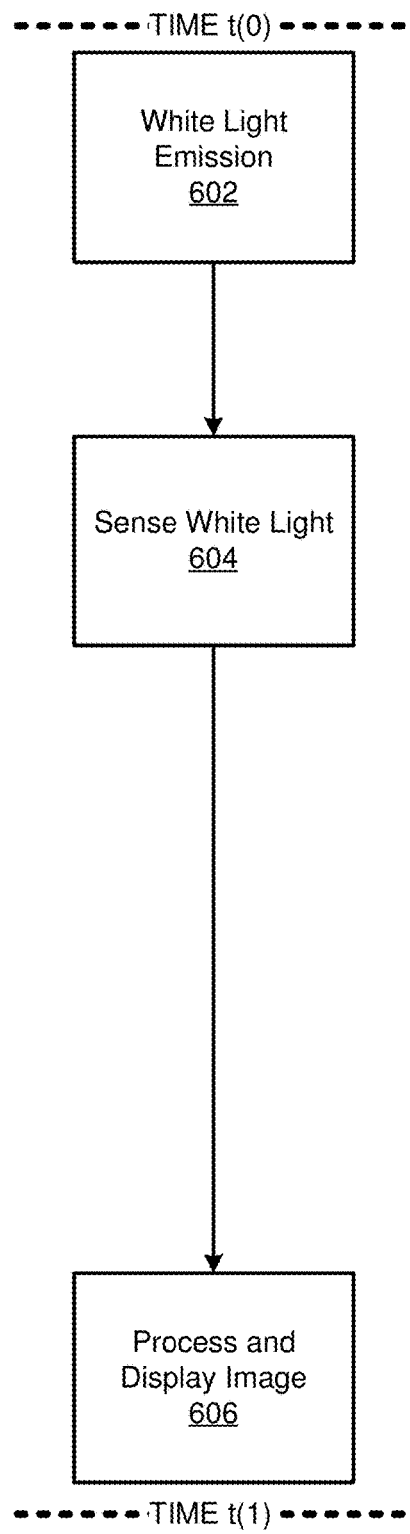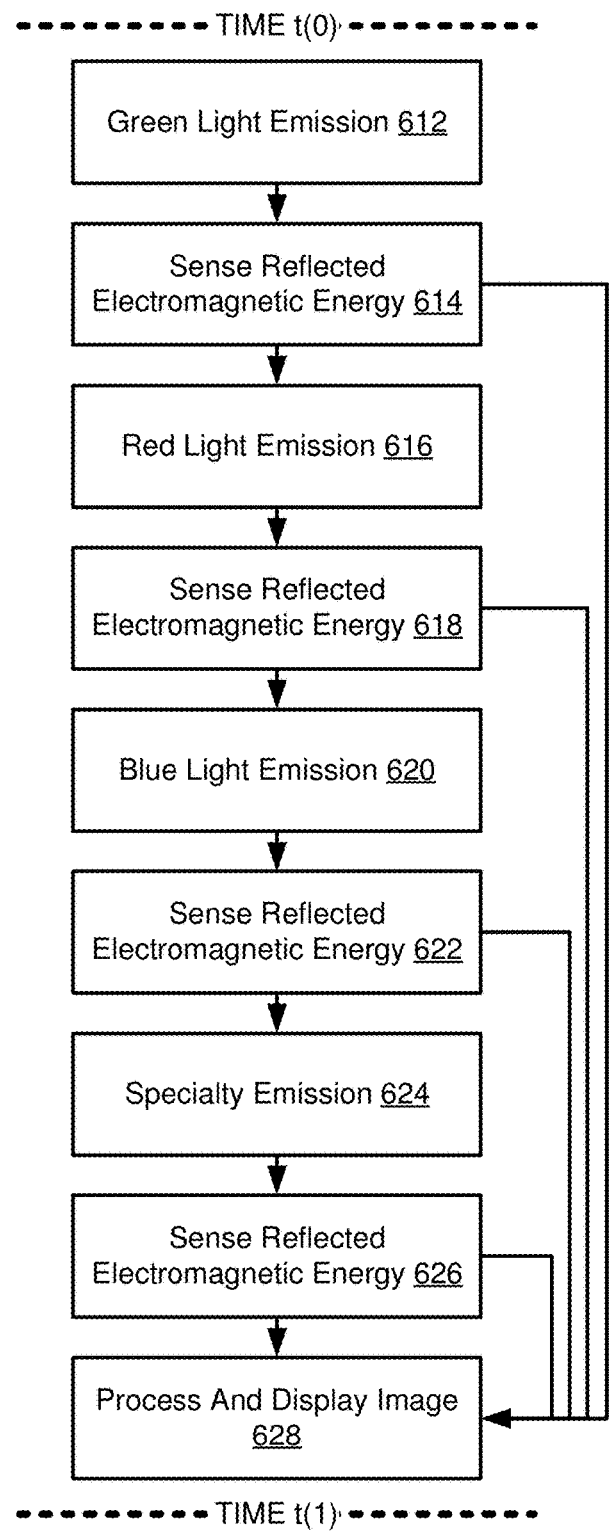
FIG. 6A
(Prior Art)
FIG. 6B

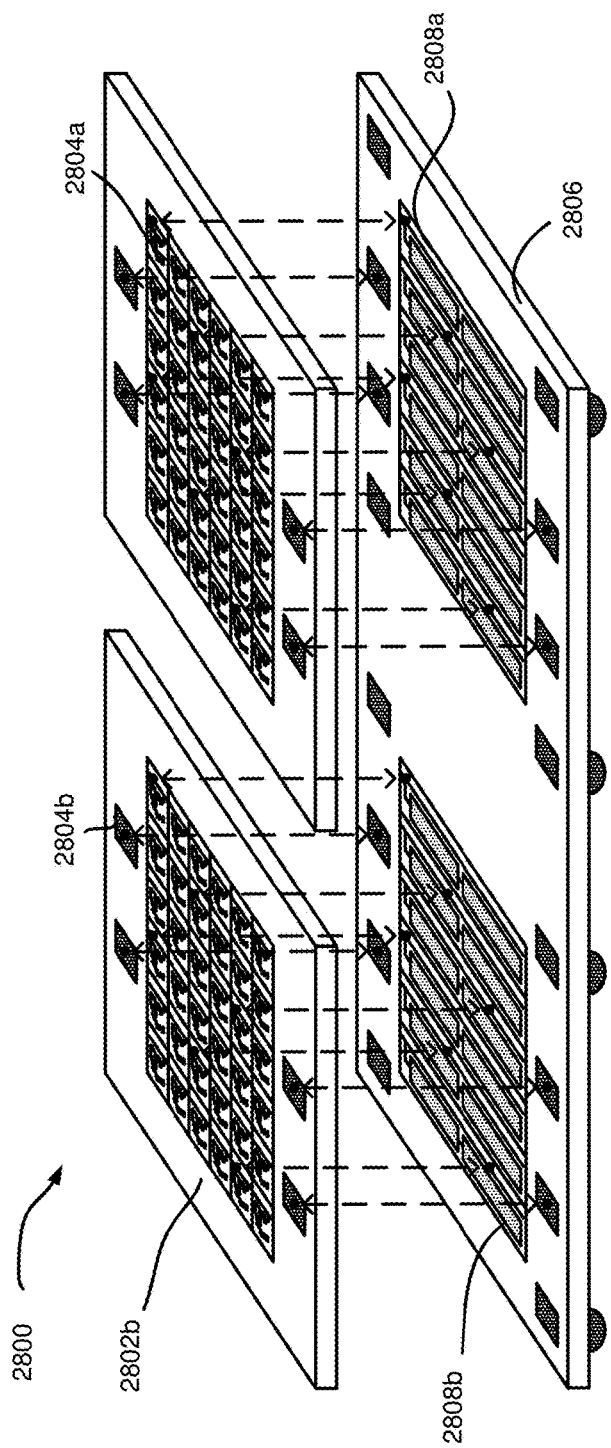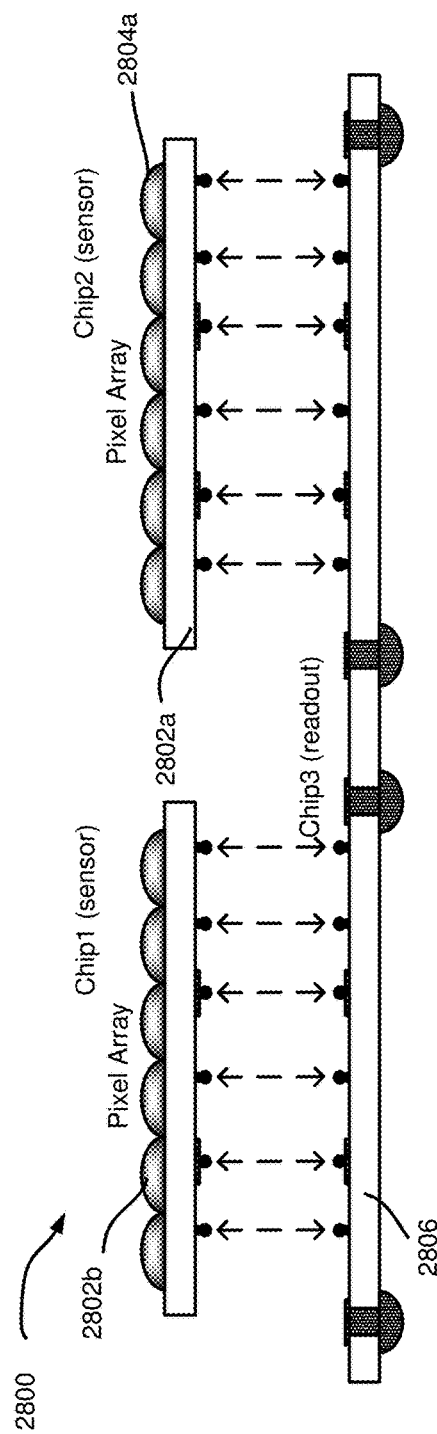

OPTICAL FIBER WAVEGUIDE IN AN ENDOSCOPIC SYSTEM FOR HYPERSPECTRAL, FLUORESCENCE, AND LASER MAPPING IMAGING

CROSS-REFERENCE TO RELATED APPLICATIONS

This application claims the benefit of U.S. Provisional Patent Application No. 62/864,281, filed Jun. 20, 2019, titled "SYSTEMS, METHODS, AND DEVICES FOR PROVIDING ILLUMINATION IN AN ENDOSCOPIC HYPERSPECTRAL AND FLUORESCENCE IMAGING ENVIRONMENT," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This disclosure is directed to digital imaging and is particularly directed to hyperspectral imaging, fluorescence imaging, and/or laser mapping imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with fluorescence, hyperspectral, and/or laser mapping data in addition to color image data. Fluorescence imaging captures the emission of light by a substance that has absorbed electromagnetic radiation and "glows" as it emits a relaxation wavelength. Hyperspectral imaging can be used to identify different materials, biological processes, and chemical processes by emitting different partitions of electromagnetic radiation and assessing the spectral responses of materials. Laser mapping imaging can capture the surface shape of objects and landscapes and measure distances between objects within a scene. Laser mapping imaging may further encompass tool tracking wherein the distances and/or dimensions of tools within a scene can be tracked relative to each other, relative to an imaging device, and/or relative to structures within the scene. In some implementations, it may be desirable to use one or more of fluorescence imaging, hyperspectral imaging, and/or laser mapping imaging in combination when imaging a scene.

However, applications of fluorescence, hyperspectral, and laser mapping technology known in the art typically require highly specialized equipment that may not be useful for multiple applications. Further, such technologies provides a limited view of an environment and typically must be used in conjunction with multiple separate systems and multiple separate image sensors that are made sensitive to specific bands of electromagnetic radiation. It is therefore desirable to develop an imaging system that can be used in a space constrained environment to generate fluorescence, hyperspectral, and/or laser mapping imaging data.

In light of the foregoing, described herein are systems, methods, and devices for fluorescence, hyperspectral, and laser mapping imaging in a light deficient environment. Such systems, methods, and devices may provide multiple datasets for identifying critical structures in a body and providing precise and valuable information about a body cavity.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 3A to 3D are illustrations of the operational cycles of a sensor used to construct an exposure frame;

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIGS. 28A and 28B illustrate a perspective view and a side view, respectively, of an implementation of an imaging sensor having a plurality of pixel arrays for producing a three-dimensional image, wherein the plurality of pixel arrays and the image sensor are built on a plurality of substrates.

DETAILED DESCRIPTION

Figure 1:
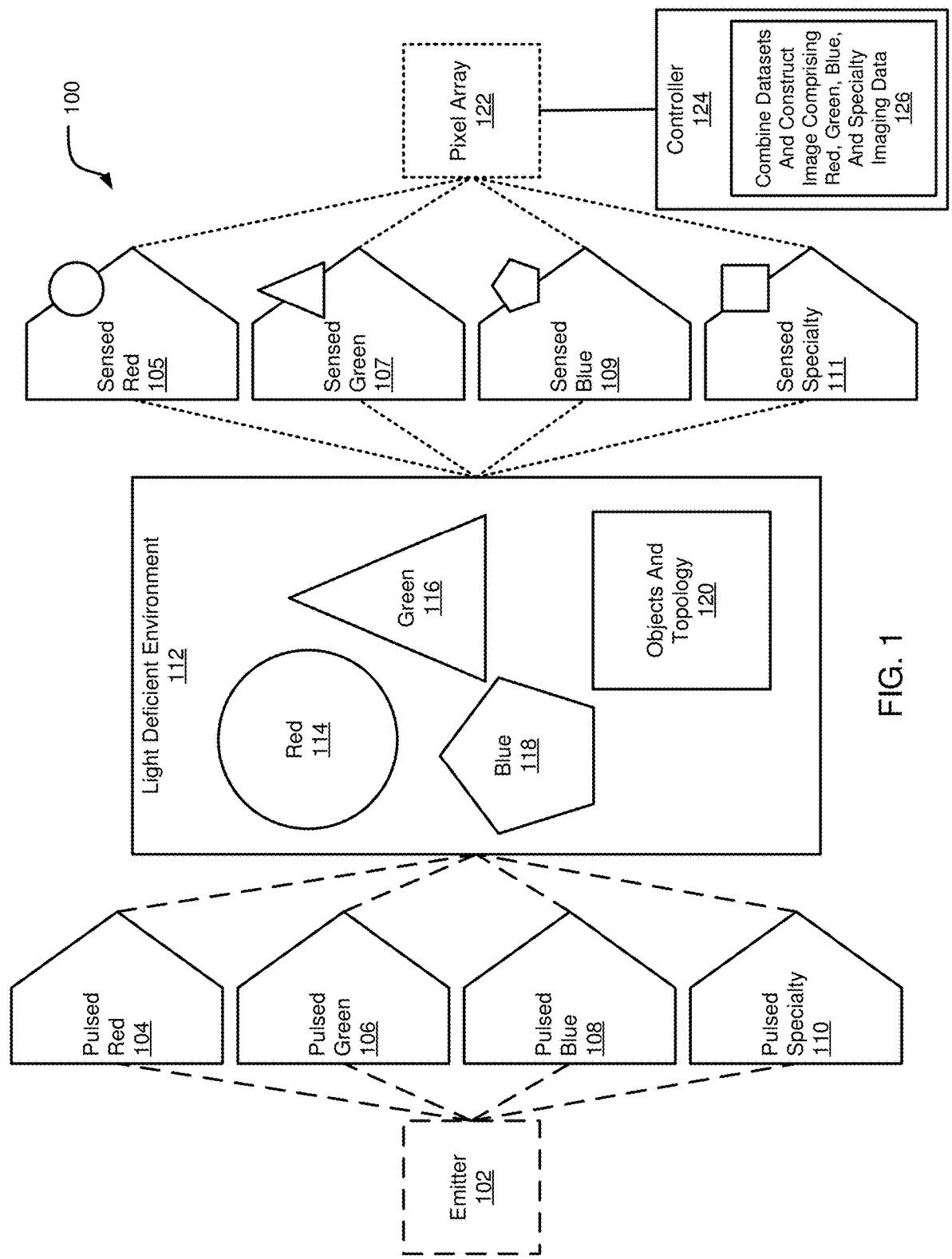
FIG. 1 is a schematic view of a system for digital imaging in a light deficient environment with a paired emitter module and pixel array.

Disclosed herein are systems, methods, and devices for digital imaging that may be primarily suited to medical applications such as medical endoscopic imaging. An embodiment of the disclosure is an endoscopic system for hyperspectral, fluorescence, laser mapping, and color imaging in a light deficient environment. Such methods, systems, and computer-based products disclosed herein provide imaging or diagnostic capabilities for use in medical robotics applications, such as the use of robotics for performing imaging procedures, surgical procedures, and the like.

An embodiment of the disclosure is an endoscopic imaging system comprising an emitter for emitting pulses of electromagnetic radiation to illuminate a scene. In an embodiment, the emitter is an emitter module comprising one or more individual emitters for pulsing the electromagnetic radiation. In an embodiment, the emitter module comprises multiple emitters that can operate independently of one another and emit different wavelengths of electromagnetic radiation. Each of the multiple emitters may include a bundle of lasers for emitting electromagnetic radiation. The multiple emitters making up the emitter module may each be configured to pulse electromagnetic radiation at different partitions or wavelengths of the electromagnetic spectrum. The pulses of electromagnetic radiation may be pulsed to a waveguide, and the waveguide may then carry the pulsed electromagnetic radiation to a distal end of an endoscope to illuminate the scene. The waveguide may include a single optical fiber or an optical fiber bundle comprising a plurality of optical fibers. The waveguide may include plastic and/or glass optical fibers for communicating electromagnetic radiation from the emitter module to the distal end of the endoscope.

In an embodiment, the waveguide terminates at the distal end of the endoscope to emanate a light cone of electromagnetic radiation. The light cone defines an area that is illuminated by the pulses of electromagnetic radiation. In some instances, the area of the light cone resulting from a single optical fiber or a bundle of optical fibers is insufficient for effective imaging. In some instances, the resulting light cone has an area smaller than the visibility region of the image sensor. Therefore, there is a desire to increase the area of the resulting light cone of electromagnetic radiation that emanates from the waveguide. In light of the foregoing, disclosed herein are multiple embodiments of a waveguide for increasing the resulting light cone of illumination at the distal end of the endoscope.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within the highly space-constrained environment in the distal end of the endoscope itself. This provides greater optical simplicity when compared with implementations known in the art. However, an acceptable solution to this approach is by no means trivial and introduces its own set of engineering challenges.

There can be a noticeable loss to image quality when the overall size of an image sensor is minimized such that the image sensor can fit within the distal tip of an endoscope. The area of the pixel array of the image sensor can be reduced by reducing the number of pixels and/or the sensing area of each individual pixel. Each of these modifications impacts the resolution, sensitivity, and dynamic range of the resultant images. Traditional endoscopic imaging systems are geared toward sensing steady broadband illumination and providing color information by virtue of segmented pixel arrays such as the Bayer pattern array. In light of the deficiencies associated with segmented pixel arrays, disclosed herein are alternative systems and methods that use a monochromatic (may be referred to as "color agnostic") pixel array that does not include individual pixel filters. In the embodiments disclosed herein, the color information is provided by pulsing an emitter with different wavelengths of electromagnetic radiation. The pulsed imaging system disclosed herein can generate color images with hyperspectral, fluorescence, and/or laser mapping imaging data overlaid thereon.

In an embodiment, the color information is determined by capturing independent exposure frames in response to pulses of different wavelengths of electromagnetic radiation. The alternative pulses may include red, green, and blue wavelengths for generating an RGB image frame consisting of a red exposure frame, a green exposure frame, and a blue exposure frame. In an alternative implementation, the alternative pulses may include luminance ("Y"), red chrominance ("Cr"), and blue chrominance "(Cb") pulses of light for generating a YCbCr image frame consisting of luminance data, red chrominance data, and blue chrominance data. The color image frame may further include data from a hyperspectral exposure frame, a fluorescence exposure frame, and/or a laser mapping exposure frame overlaid on the RGB or YCbCr image frame. A hyperspectral pulse may be an emission of electromagnetic radiation have eliciting a spectral response from an object. The hyperspectral exposure frame may include an indication of a location of the object that emitted the spectral response. A fluorescence pulse may be a fluorescence excitation wavelength of electromagnetic radiation for fluorescing a reagent. The fluorescence exposure frame may include an indication of the fluorescence reagent within the scene. The laser mapping pulse may include one or more pulses for measuring distances or dimensions within a scene, tracking the presence and location of tools in the scene, generating a three-dimensional topographical map of the scene, and so forth. Alternating the wavelengths of the pulsed electromagnetic radiation allows the full pixel array to be exploited and avoids the artifacts introduced by Bayer pattern pixel arrays.

In some instances, it is desirable to generate endoscopic imaging with multiple data types or multiple images overlaid on one another. For example, it may be desirable to generate a color (RGB or YCbCr) image that further includes hyperspectral, fluorescence, and/or laser mapping imaging data overlaid on the color image. An overlaid image of this nature may enable a medical practitioner or computer program to identify highly accurate dimensions and three-dimensional topologies of critical body structures and further identify distances between tools and other structures within the light deficient environment based on the laser mapping data. Historically, this would require the use of multiple sensor systems including an image sensor for color imaging and one or more additional image sensors for hyperspectral, fluorescence, or laser mapping imaging. In such systems, the multiple image sensors would have multiple types of pixel sensors that are each sensitive to distinct ranges of electromagnetic radiation. In systems known in the art, this includes the three separate types of pixel sensors for generating a color image along with additional sensors and systems for generating the hyperspectral, fluorescence, and laser mapping data. These multiple different sensors consume a prohibitively large physical space and cannot be located at a distal tip of the endoscope. In systems known in the art, the camera or cameras are not placed at the distal tip of the endoscope and are instead placed in an endoscope handpiece or robotic unit. This introduces numerous disadvantages and causes the endoscope to be very delicate. The delicate endoscope may be damaged and image quality may be degraded when the endoscope is bumped or impacted during use. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

The fluorescence imaging techniques discussed herein can be used in combination with one or more fluorescent reagents or dyes. The location of a reagent can be identified by emitting an excitation wavelength of electromagnetic radiation that causes the reagent to fluoresce. The relaxation wavelength emitted by the reagent can be read by an image sensor to identify the location of the reagent within a scene. Depending on the type of reagent that is used, the location of the reagent may further indicate the location of critical structures such as certain types of tissue, cancerous cells versus non-cancerous cells, and so forth.

The hyperspectral imaging techniques discussed herein can be used to "see through" layers of tissue in the foreground of a scene to identify specific types of tissue and/or specific biological or chemical processes. Hyperspectral imaging can be used in the medical context to quantitatively track the process of a disease and to determine tissue pathology. Additionally, hyperspectral imaging can be used to identify critical structures such as nervous tissue, muscle tissue, cancerous cells, and so forth. In an embodiment, partitions of electromagnetic radiation are pulsed, and data is gathered regarding the spectral responses of different types of tissue in response to the partitions of electromagnetic radiation. A datastore of spectral responses can be generated and analyzed to assess a scene and predict which tissues are present within the scene based on the sensed spectral responses.

The laser mapping imaging techniques discussed herein can be assessed to generate a three-dimensional landscape map of a scene and to calculate distances between objects within the scene. The laser mapping data can be used in conjunction with fluorescence imaging and/or hyperspectral imaging to calculate the precise location and dimensions of critical structures. For example, the location and boundaries of a critical structure may be identified with the fluorescence and/or hyperspectral imaging. The precise measurements for the location of the critical structure, the dimensions of the critical structure, and the distance from the critical structure to other objects can then be calculated based on the laser mapping data.

Hyperspectral Imaging

In an embodiment, the systems, methods, and devices disclosed herein provide means for generating hyperspectral imaging data in a light deficient environment. Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any wavelength bands in the electromagnetic spectrum, including infrared wavelengths, the visible spectrum, the ultraviolet spectrum, x-ray wavelengths, or any suitable combination of various wavelength bands.

Hyperspectral imaging was originally developed for applications in mining and geology. Unlike a normal camera image that provides limited information to the human eye, hyperspectral imaging can identify specific minerals based on the spectral signatures of the different minerals. Hyperspectral imaging can be useful even when captured in aerial images and can provide information about, for example, oil or gas leakages from pipelines or natural wells and their effects on nearby vegetation. This information is collected based on the spectral signatures of certain materials, objects, or processes that may be identified by hyperspectral imaging.

Hyperspectral imaging includes spectroscopy and digital photography. In an embodiment of hyperspectral imaging, a complete spectrum or some spectral information is collected at every pixel in an image plane. The goal of hyperspectral imaging may vary for different applications. In one application, the goal of hyperspectral imaging is to obtain the entire electromagnetic spectrum of each pixel in an image scene. This may enable certain objects to be found that might otherwise not be identifiable under the visible light wavelength bands. This may enable certain materials or tissues to be identified with precision when those materials or tissues might not be identifiable under the visible light wavelength bands. Further, this may enable certain processes to be detected by capturing an image across all wavelengths of the electromagnetic spectrum.

In an embodiment of the disclosure, an endoscope system illuminates a source and pulses electromagnetic radiation for spectral or hyperspectral imaging. Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any wavelength bands in the electromagnetic spectrum, including infrared wavelengths, the visible spectrum, the ultraviolet spectrum, x-ray wavelengths, or any suitable combination of various wavelength bands. Spectral imaging may overlay imaging generated based on non-visible bands (e.g., infrared) on top of imaging based on visible bands (e.g. a standard RGB image) to provide additional information that is easily discernable by a person or computer algorithm.

Hyperspectral imaging enables numerous advantages over conventional imaging. The information obtained by hyperspectral imaging enables medical practitioners and/or computer-implemented programs to precisely identify certain tissues or conditions that may not be possible to identify with RGB imaging. Additionally, hyperspectral imaging may be used during medical procedures to provide image-guided surgery that enables a medical practitioner to, for example, view tissues located behind certain tissues or fluids, identify atypical cancerous cells in contrast with typical healthy cells, identify certain tissues or conditions, identify critical structures, and so forth. Hyperspectral imaging provides specialized diagnostic information about tissue physiology, morphology, and composition that cannot be generated with conventional imaging.

Hyperspectral imaging may provide particular advantages over conventional imaging in medical applications. The information obtained by hyperspectral imaging can enable medical practitioners and/or computer-implemented programs to precisely identify certain tissues or conditions that may lead to diagnoses that may not be possible or may be less accurate if using conventional imaging such as RGB imaging. Additionally, hyperspectral imaging may be used during medical procedures to provide image-guided surgery that may enable a medical practitioner to, for example, view tissues located behind certain tissues or fluids, identify atypical cancerous cells in contrast with typical healthy cells, identify certain tissues or conditions, identify critical structures and so forth. Hyperspectral imaging may provide specialized diagnostic information about tissue physiology, morphology, and composition that cannot be generated with conventional imaging.

Endoscopic hyperspectral imaging may present advantages over conventional imaging in various applications and implementations of the disclosure. In medical implementations, endoscopic hyperspectral imaging may permit a practitioner or computer-implemented program to discern, for example, nervous tissue, muscle tissue, various vessels, the direction of blood flow, and so forth. Hyperspectral imaging may enable atypical cancerous tissue to be precisely differentiated from typical healthy tissue and may therefore enable a practitioner or computer-implemented program to discern the boundary of a cancerous tumor during an operation or investigative imaging. Additionally, hyperspectral imaging in a light deficient environment as disclosed herein may be combined with the use of a reagent or dye to enable further differentiation between certain tissues or substances. In such an embodiment, a reagent or dye may be fluoresced by a specific wavelength band in the electromagnetic spectrum and therefore provide information specific to the purpose of that reagent or dye. The systems, methods, and devices disclosed herein may enable any number of wavelength bands to be pulsed such that one or more reagents or dyes may be fluoresced at different times, and further so that one or more partitions of electromagnetic radiation may be pulsed for hyperspectral imaging in the same imaging session. In certain implementations, this enables the identification or investigation of a number of medical conditions during a single imaging procedure.

Fluorescence Imaging

The systems, methods, and devices disclosed herein provide means for generating fluorescence imaging data in a light deficient environment. The fluorescence imaging data may be used to identify certain materials, tissues, components, or processes within a body cavity or other light deficient environment. In certain embodiments, fluorescence imaging is provided to a medical practitioner or computer-implemented program to enable the identification of certain structures or tissues within a body. Such fluorescence imaging data may be overlaid on black-and-white or RGB images to provide additional information and context.

Fluorescence is the emission of light by a substance that has absorbed light or other electromagnetic radiation. Certain fluorescent materials may "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance. However, when the absorbed electromagnetic radiation is intense, it is possible for one electron to absorb two photons. This two-photon absorption can lead to emission of radiation having a shorter wavelength, and therefore higher energy, than the absorbed radiation. Additionally, the emitted radiation may also be the same wavelength as the absorbed radiation.

Fluorescence imaging has numerous practical applications, including mineralogy, gemology, medicine, spectroscopy for chemical sensors, detecting biological processes or signals, and so forth. Fluorescence may particularly be used in biochemistry and medicine as a non-destructive means for tracking or analyzing biological molecules. The biological molecules, including certain tissues or structures, may be tracked by analyzing the fluorescent emission of the biological molecules after being excited by a certain wavelength of electromagnetic radiation. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of electromagnetic radiation. Different reagents or dyes may include different molecules, proteins, and/or quantum dots that will fluoresce at particular wavelengths of electromagnetic radiation. Thus, it may be necessary to excite the reagent or dye with a specialized band of electromagnetic radiation to achieve fluorescence and identify the desired tissue, structure, or process in the body.

Fluorescence imaging may provide valuable information in the medical field that may be used for diagnostic purposes and/or may be visualized in real-time during a medical procedure. Specialized reagents or dyes may be administered to a body to fluoresce certain tissues, structures, chemical processes, or biological processes. The fluorescence of the reagent or dye may highlight body structures such as blood vessels, nerves, particular organs, and so forth. Additionally, the fluorescence of the reagent or dye may highlight conditions or diseases such as cancerous cells or cells experiencing a certain biological or chemical process that may be associated with a condition or disease. The fluorescence imaging may be used in real-time by a medical practitioner or computer program for differentiating between, for example, cancerous and non-cancerous cells during a surgical tumor extraction. The fluorescence imaging may further be used as a non-destructive means for tracking and visualizing over time a condition in the body that would otherwise not be visible by the human eye or distinguishable in an RGB image.

The systems, methods, and devices for generating fluorescence imaging data may be used in coordination with reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The endoscopic imaging system disclosed herein is used to excite and fluoresce the reagent or dye. The fluorescence of the reagent or dye is captured by the endoscopic imaging system to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the endoscopic imaging system emits each of the applicable wavelengths to fluoresce each of the applicable reagents or dyes. This may negate the need to perform individual imaging procedures for each of the plurality of reagents or dyes.

Imaging reagents can enhance imaging capabilities in pharmaceutical, medical, biotechnology, diagnostic, and medical procedure industries. Many imaging techniques such as X-ray, computer tomography (CT), ultrasound, magnetic resonance imaging (MRI), and nuclear medicine, mainly analyze anatomy and morphology and are unable to detect changes at the molecular level. Fluorescent reagents, dyes, and probes, including quantum dot nanoparticles and fluorescent proteins, assist medical imaging technologies by providing additional information about certain tissues, structures, chemical processes, and/or biological processes that are present within the imaging region. Imaging using fluorescent reagents enables cell tracking and/or the tracking of certain molecular biomarkers. Fluorescent reagents may be applied for imaging cancer, infection, inflammation, stem cell biology, and others. Numerous fluorescent reagents and dyes are being developed and applied for visualizing and tracking biological processes in a non-destructive manner. Such fluorescent reagents may be excited by a certain wavelength or band of wavelengths of electromagnetic radiation. Similarly, those fluorescent reagents may emit relaxation energy at a certain wavelength or band of wavelengths when fluorescing, and the emitted relaxation energy may be read by a sensor to determine the location and/or boundaries of the reagent or dye.

In an embodiment of the disclosure, an endoscopic imaging system pulses electromagnetic radiation for exciting an electron in a fluorescent reagent or dye. The endoscopic imaging system may pulse multiple different wavelengths of electromagnetic radiation for fluorescing multiple different reagents or dyes during a single imaging session. The endoscope includes an image sensor that is sensitive to the relaxation wavelength(s) of the one or more reagents or dyes. The imaging data generated by the image sensor can be used to identify a location and boundary of the one or more reagents or dyes. The endoscope system may further pulse electromagnetic radiation in red, green, and blue bands of visible light such that the fluorescence imaging can be overlaid on an RGB video stream.

Laser Mapping Imaging

In an embodiment, the systems, methods, and devices disclosed herein provide means for generating laser mapping data with an endoscopic imaging system. Laser mapping data can be used to determine precise measurements and topographical outlines of a scene. In one implementation, laser mapping data is used to determine precise measurements between, for example, structures or organs in a body cavity, devices or tools in the body cavity, and/or critical structures in the body cavity. As discussed herein, the term "laser mapping" may encompass technologies referred to as laser mapping, laser scanning, topographical scanning, three-dimensional scanning, laser tracking, tool tracking, and others. A laser mapping exposure frame as discussed herein may include topographical data for a scene, dimensions between objects or structures within a scene, dimensions or distances for tools or objects within a scene, and so forth.

Laser mapping generally includes the controlled deflection of laser beams. Within the field of three-dimensional object scanning, laser mapping combines controlled steering of laser beams with a laser rangefinder. By taking a distance measurement at every direction, the laser rangefinder can rapidly capture the surface shape of objects, tools, and landscapes. Construction of a full three-dimensional topology may include combining multiple surface models that are obtained from different viewing angles. Various measurement systems and methods exist in the art for applications in archaeology, geography, atmospheric physics, autonomous vehicles, and others. One such system includes light detection and ranging (LIDAR), which is a three-dimensional laser mapping system. LIDAR has been applied in navigation systems such as airplanes or satellites to determine position and orientation of a sensor in combination with other systems and sensors. LIDAR uses active sensors to illuminate an object and detect energy that is reflected off the object and back to a sensor.

As discussed herein, the term "laser mapping" includes laser tracking. Laser tracking, or the use of lasers for tool tracking, measures objects by determining the positions of optical targets held against those objects. Laser trackers can be accurate to the order of 0.025 mm over a distance of several meters. In an embodiment, an endoscopic imaging system pulses light for use in conjunction with a laser tracking system such that the position or tools within a scene can be tracked and measured. In such an embodiment, the endoscopic imaging system may pulse a laser tracking pattern on a tool, object, or other structure within a scene being imaged by the endoscopic imaging system. A target may be placed on the tool, object, or other structure within the scene. Measurements between the endoscopic imaging system and the target can be triggered and taken at selected points such that the position of the target (and the tool, object, or other structure to which the target is affixed) can be tracked by the endoscopic imaging system.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral image. The pixels may be color agnostic such that each pixel generates data for each pulse of electromagnetic radiation, including pulses for red, green, and blue visible light wavelengths along with other wavelengths used for hyperspectral imaging.

A system of the disclosure is an endoscopic imaging system for use in a light deficient environment. The system includes an endoscope comprising an image sensor, wherein the image sensor is configured to sense reflected electromagnetic radiation for generating a plurality of exposure frames that can be combined to generate an RGB image frame with hyperspectral data overlaid thereon. The system includes an emitter for emitting pulses of electromagnetic radiation. The system includes a controller (may alternatively be referred to as a "control circuit" in electronic communication with the image sensor and the emitter. The controller controls a duty cycle of the emitter in response to signals corresponding to a duty cycle of the emitter. The image sensor includes bidirectional pads that can send and receive information. The bidirectional pads of the image sensor operate in a frame period divided into three defined states, including a rolling readout state, a service line state, and a configuration state. The system includes an oscillator disposed in the controller and a frequency detector connected to the controller. The frequency detector controls a clock frequency of the image sensor in response to signals from the controller that correspond to the frequency of the oscillator. The system is such that clock signal data is transmitted from the bidirectional pads of the image sensor to the controller during the service line phase and the configuration phase. The system is such that exposure frames are synchronized without the use of an input clock or a data transmission clock.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary some-what. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert. An emitter may comprise an emitter module comprising one or more electromagnetic sources for pulsing electromagnetic radiation.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with specialty data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in image data sensed by the pixel array 122.

The emitter 102 may include one or more emitters for pulsing electromagnetic radiation. Each of the one or more emitters may include one or more lasers for pulsing a partition of wavelengths of electromagnetic radiation. The emitter 102 may be capable of pulsing different partitions of the electromagnetic spectrum by way of multiple independent emitters. As discussed herein, including in the appended claims, the term "emitter" may refer to a single emitter or laser for pulsing electromagnetic radiation, a collection of emitters or lasers for pulsing electromagnetic radiation, and an "emitter module" as discussed herein. Therefore, the term "emitter" as used herein should not be seen as limiting and may refer to one or more emitters for pulsing electromagnetic radiation and may also refer to the collection of emitters found within an emitter module.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108 wavelengths, and a specialty 110 emission. The specialty 110 emission may include an excitation wavelength for fluorescing a reagent, a hyperspectral partition of electromagnetic radiation, and/or a laser mapping pattern. The specialty 110 emission may include multiple separate emissions that are separate and independent from one another. The specialty 110 emission may include a combination of an excitation wavelength for fluorescing a reagent and a laser mapping pattern, wherein the emissions are separate and independent from one another. The data resulting from the separate emissions can be analyzed in tandem to identify a critical structure within a scene based on the fluorescence imaging data, and further to identify the dimensions or positioning of the critical structure based on the laser mapping data in combination with the fluorescence imaging data. The specialty 110 emission may include a combination of a hyperspectral band of electromagnetic radiation and a laser mapping pattern, wherein the emissions are separate and independent from one another. The data resulting from the separate emissions can be analyzed in tandem to identify a critical structure within a scene based on the hyperspectral imaging data, and further to identify the dimensions or positioning of the critical structure based on the laser mapping data in combination with the hyperspectral imaging data. In an embodiment, the specialty 110 emission includes any desirable combination of emissions that may be combined with the data resulting from the pulsed red 104, pulsed green 106, and pulsed blue 108 emissions. The specialty 110 emissions may be dispersed within a pulsing pattern such that the different types of specialty 110 emissions are not pulsed as frequently as the pulsed red 104, pulsed green 106, and pulsed blue 108 emissions.

In an alternative embodiment not illustrated in FIG. 1, the pulsed emissions of light include a luminance ("Y") emission, a red chrominance ("Cr") emission, and a blue chrominance ("Cb") emission in place of the pulsed red 104, pulsed green 106, and pulsed blue 108 emissions. In an embodiment, the controller or the emitter 102 modulates the pulses of electromagnetic radiation to provide luminance and/or chrominance information according to color transformation coefficients that convert light energy from red, green, and blue light energy spaces to luminance, red chrominance, and blue chrominance light energy space. The pulsed emissions of light may further include modulated blue chrominance ("λY+Cb") pulses and/or modulated red chrominance ("δY+Cr") pulses.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting a specialty 110 emission for mapping the topology 120 of a scene within the light deficient environment 112. The emitter 102 is capable of emitting the pulsed red 104, pulsed green 106, pulsed blue 108, and pulsed specialty 110 emissions in any desired sequence.

The pixel array 122 senses reflected electromagnetic radiation. Each of the sensed red 105, the sensed green 107, the sensed blue 109, and the sensed specialty 111 data can be referred to as an "exposure frame." The sensed specialty 111 may result in multiple separate exposure frames that are separate and independent from one another. For example, the sensed specialty 111 may result in a fluorescence exposure frame, a hyperspectral exposure frame, and/or a laser mapping exposure frame comprising laser mapping data. Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed specialty 111 exposure frame identifying the topology 120 and corresponding in time with the specialty 110 emission.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, the laser mapping data, fluorescence imaging data, and/or hyperspectral imaging data.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes a topology 120 that can be sensed and mapped into a three-dimensional rendering. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

Figure 2:
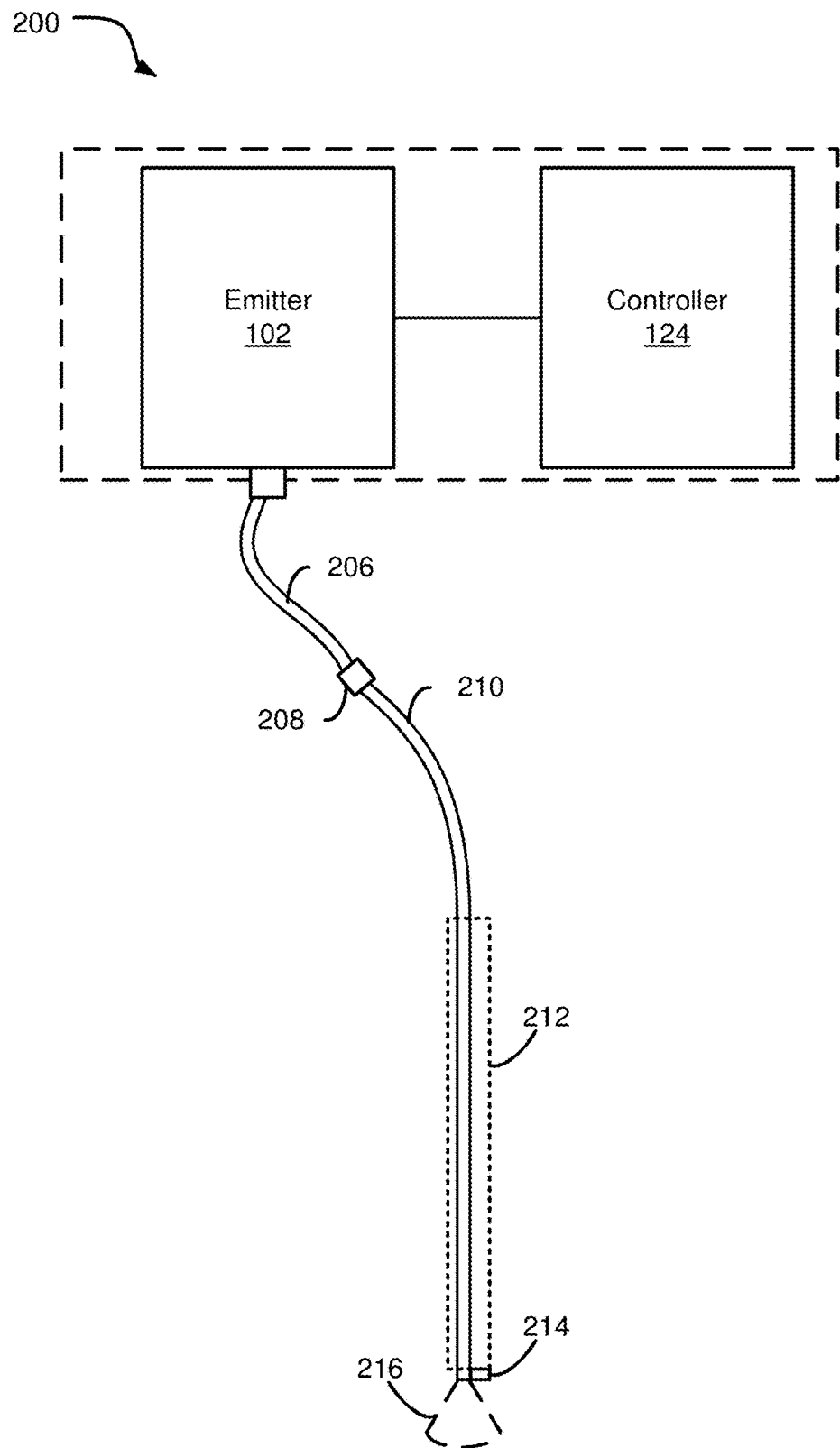
FIG. 2 illustrates a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 102, a controller 124, a jumper waveguide 206, a waveguide connector 208, a lumen waveguide 210, an endoscope 212, and an image sensor 214 with accompanying optical components (such as a lens). The emitter 102 (may be generically referred to as a "light source") generates light that travels through the jumper waveguide 206 and the lumen waveguide 210 to illuminate a scene at a distal end of the endoscope 212. The emitter 102 may be used to emit any wavelength of electromagnetic energy including visible wavelengths, infrared, ultraviolet, hyperspectral, fluorescence excitation, laser mapping pulsing schemes, or other wavelengths. The endoscope 212 may be inserted into a patient's body for imaging, such as during a procedure or examination. The electromagnetic radiation is output in a light cone 216 formation as illustrated by dashed lines. A scene illuminated by the light may be captured using the image sensor 214 and displayed for a doctor or some other medical personnel. The controller 124 may provide control signals to the emitter 102 to control when illumination is provided to a scene. In one embodiment, the emitter 102 and controller 124 are located within a camera controller unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 102. For example, a jumper waveguide 206 may receive light from an emitter within the emitter 102 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to an emitter module without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
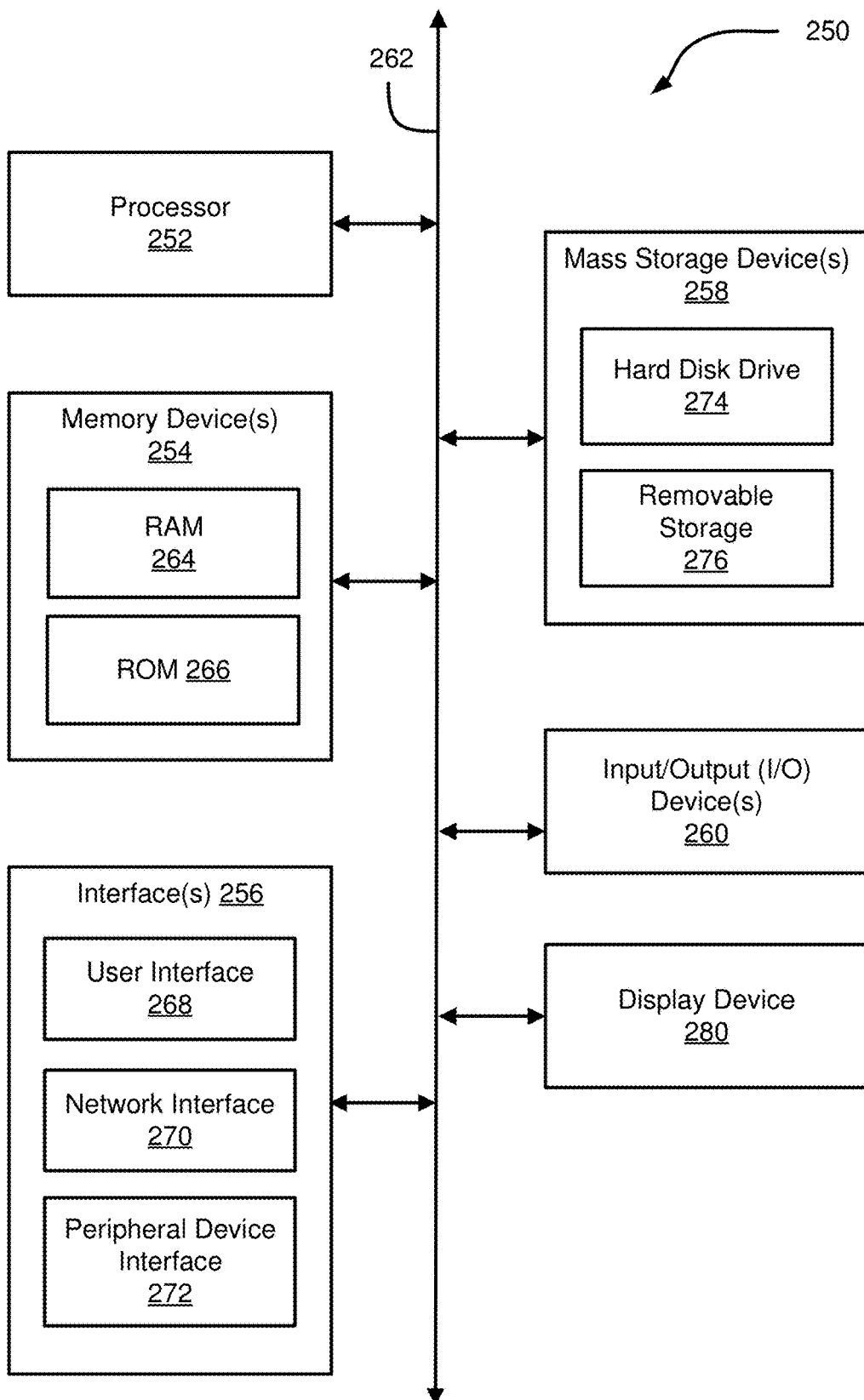
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera controller may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, controllers, camera controllers, handheld devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera controller, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
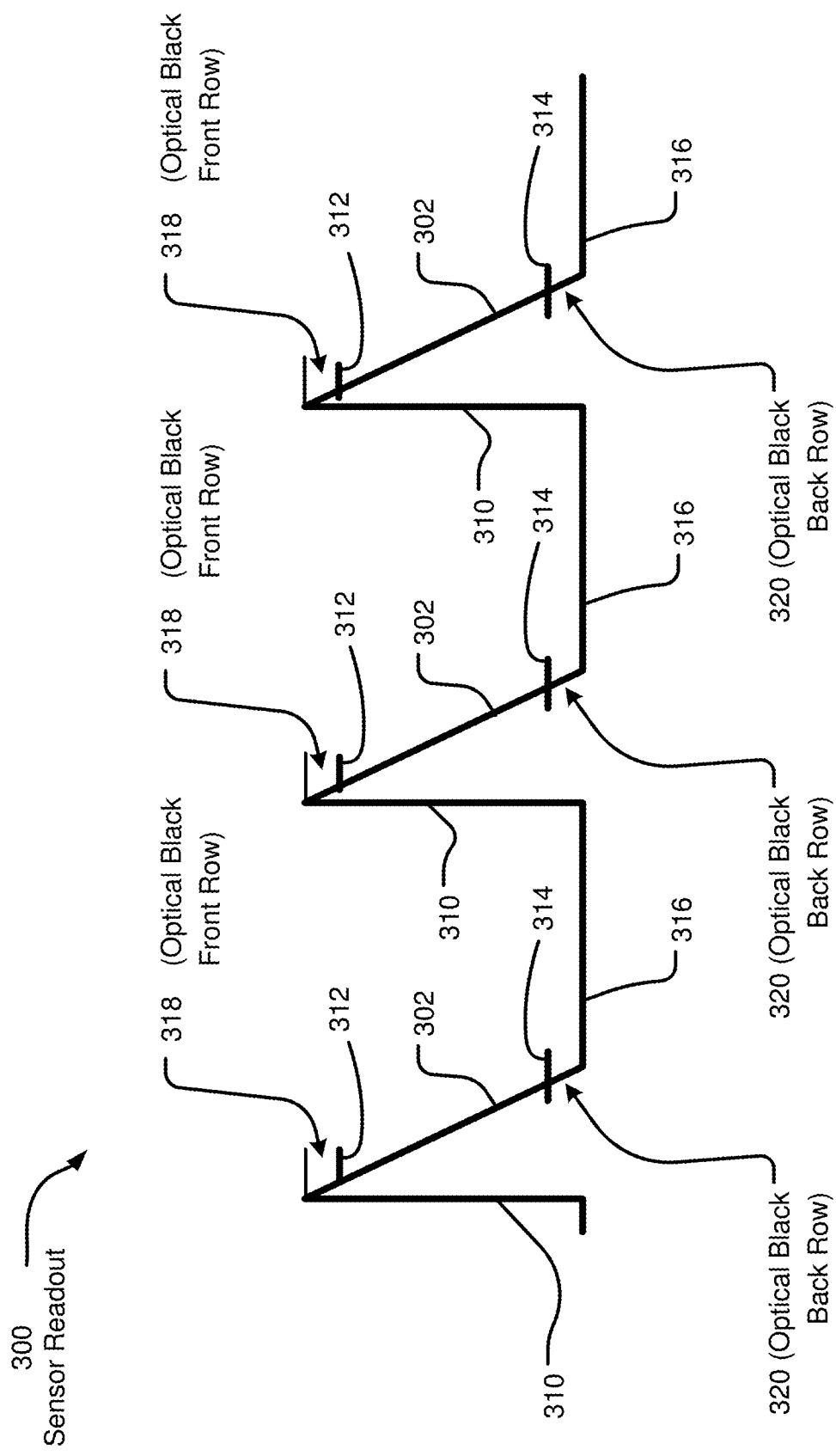

FIG. 3A illustrates the operational cycles of a sensor used in rolling readout mode or during the sensor readout 300. The frame readout may start at and may be represented by vertical line 310. The read-out period is represented by the diagonal or slanted line 302. The active pixels of the pixel array of the image sensor may be read out on a row by row basis, the top of the downwards slanted edge being the sensor top row 312 and the bottom of the downwards slanted edge being the sensor bottom row 314. The time between the last row readout and the next readout cycle may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout phase. The position of the electronic shutter 322 can be moved between two readout cycles 302 to control the pixel saturation for a given amount of light. It should be noted that this technique allows for a constant integration time between two different lines but introduces a delay when moving from top to bottom rows.

FIG. 3C illustrates the case where the electronic shutter 322 has been removed. In this configuration, the integration of the incoming light may start during readout 302 and may end at the next readout cycle 302, which also defines the start of the next integration.

Figure 3D:
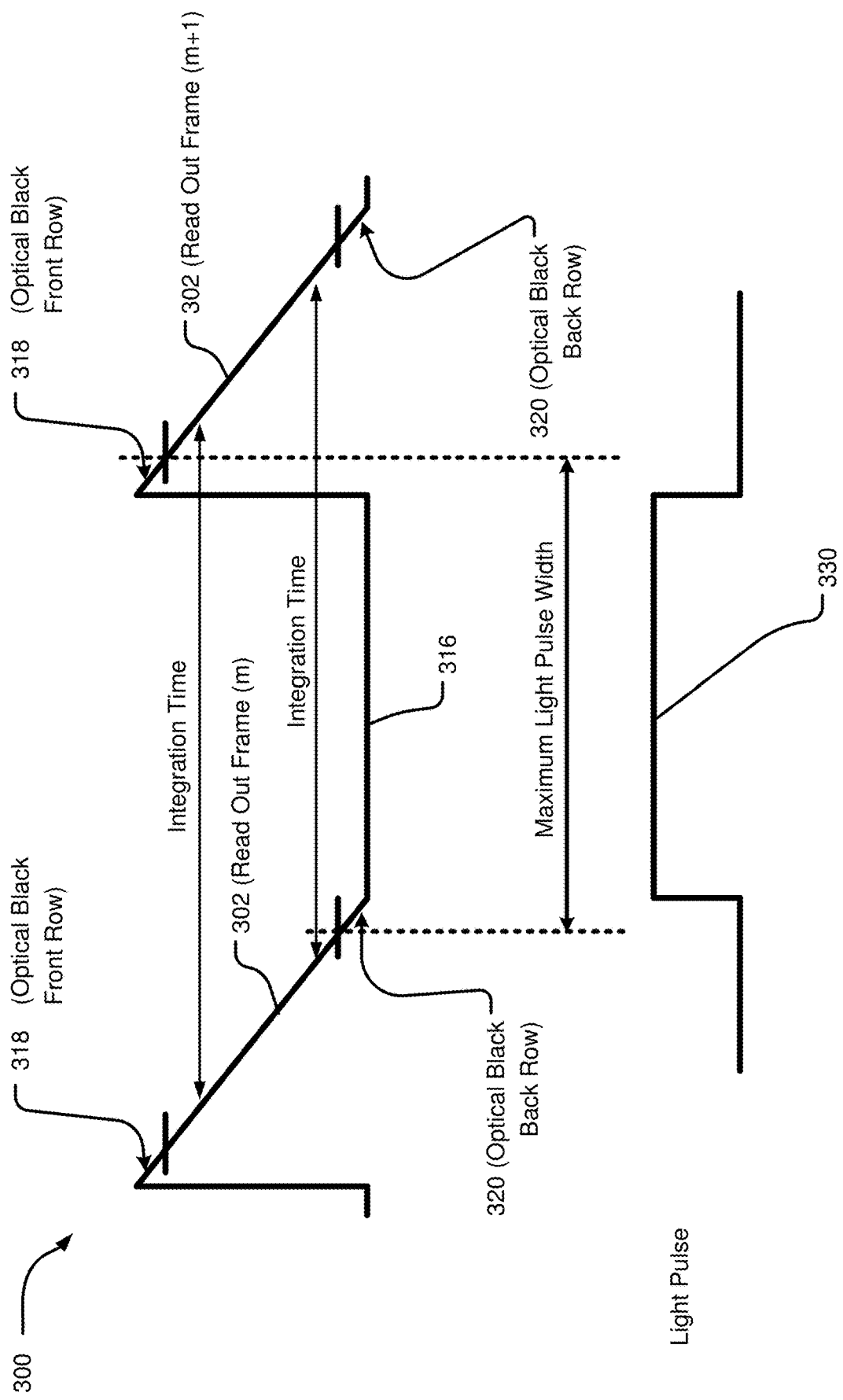

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
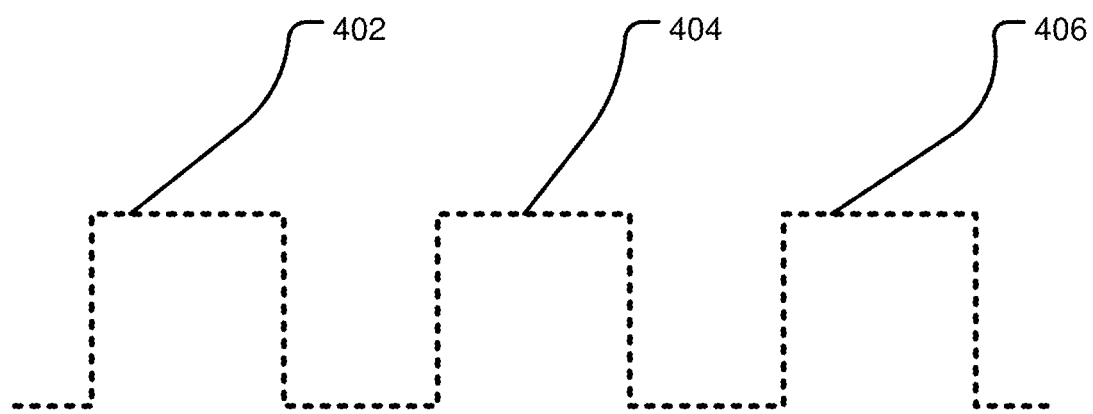
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking portion 316 of the sensor operation cycle. In an embodiment, the emitter may pulse for a duration that is during portions of two or more sensor operational cycles. In an embodiment, the emitter may begin a pulse during the blanking portion 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
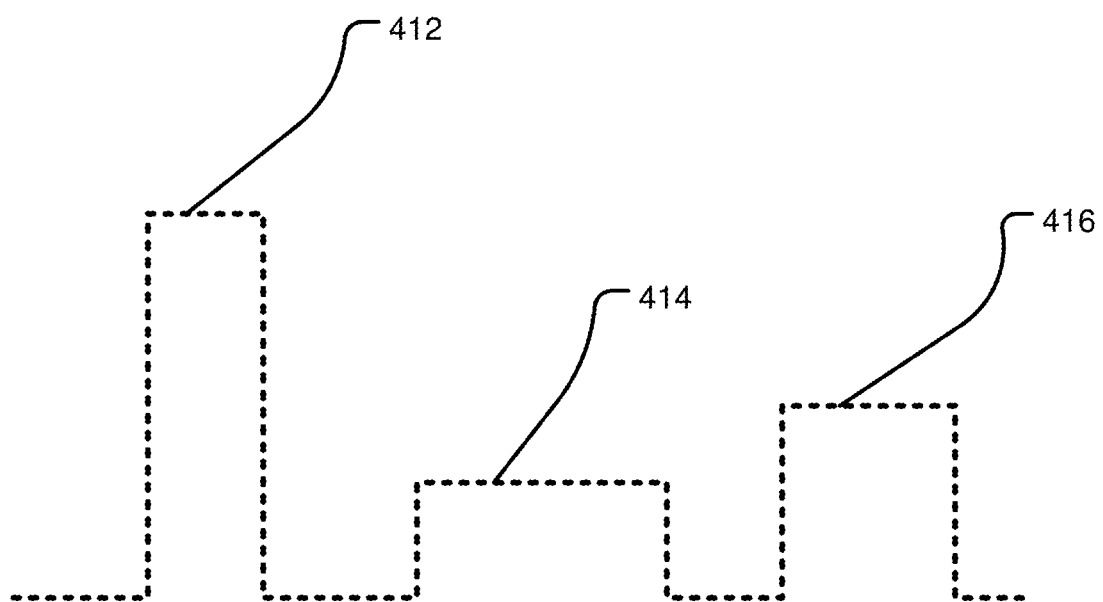
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
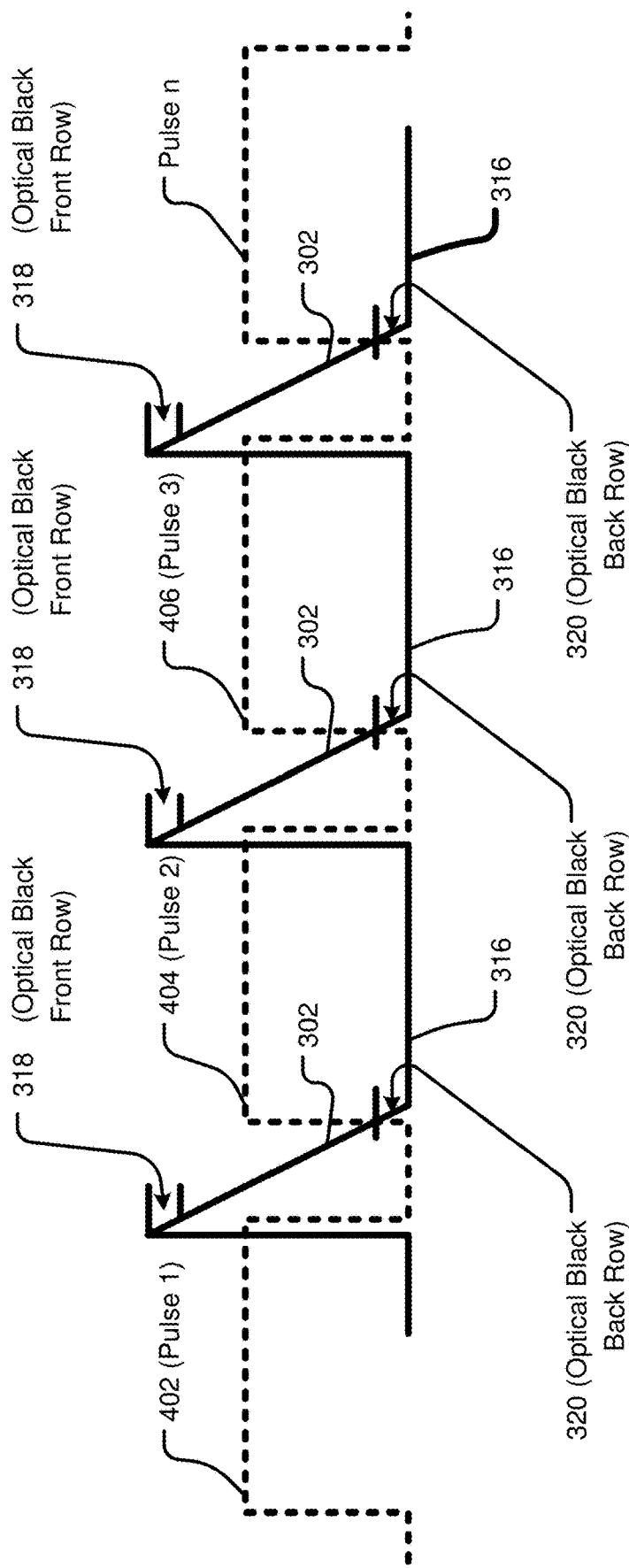
FIG. 5 is a graphical representation of an embodiment of the disclosure combining the operational cycles of a sensor, the electromagnetic emitter, and the emitted electromagnetic pulses of FIGS. 3A-4B, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an RGB image frame is generated based on three exposure frames, including a red exposure frame generated by the image sensor subsequent to a red emission, a green exposure frame generated by the image sensor subsequent to a green emission, and a blue exposure frame generated by the image sensor subsequent to a blue emission. Fluorescence imaging data may be overlaid on the RGB image frame. The fluorescence imaging data may be drawn from one or more fluorescence exposure frames. A fluorescence exposure frame includes data generated by the image sensor during the readout period 302 subsequent to emission of an excitation wavelength of electromagnetic radiation for exciting a fluorescent reagent. The data sensed by the pixel array subsequent to the excitation of the fluorescent reagent may be the relaxation wavelength emitted by the fluorescent reagent. The fluorescence exposure frame may include multiple fluorescence exposure frames that are each generated by the image sensor subsequent to a different type of fluorescence excitation emission. In an embodiment, the fluorescence exposure frame includes multiple fluorescence exposure frames, including a first fluorescence exposure frame generated by the image sensor subsequent to an emission of electromagnetic radiation with a wavelength from about 770 nm to about 790 and a second fluorescence exposure frame generated by the image sensor subsequent to an emission of electromagnetic radiation with a wavelength from about 795 nm to about 815 nm. The fluorescence exposure frame may include further additional fluorescence exposure frames that are generated by the image sensor subsequent to other fluorescence excitation emissions of light as needed based on the imaging application.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 316. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a specialty 624 emission and sensing reflected electromagnetic energy 626 subsequent to each of the one or more emissions of the specialty 624 emission. The specialty emission may include one or more separate emissions such as an excitation wavelength of a fluorescent reagent, a hyperspectral emission, and/or a laser mapping emission. Each of the separate multiple specialty emissions may be independently sensed by the image sensor to generate separate and independent exposure frames. The image is processed and displayed at 628 based on each of the sensed reflected electromagnetic energy instances 614, 618, 622, and 626.

The process illustrated in FIG. 6B provides a higher resolution image and provides a means for generating an RGB image that further includes specialty data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An example embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Laser mapping pulsing scheme;
  viii. Fluorescence excitation pulse;
  ix. Hyperspectral pulse;
  x. (Repeat)

A further example embodiment may comprise a pulse cycle pattern as follows:
  i. Green pulse;
  ii. Red pulse;
  iii. Blue pulse;
  iv. Fluorescence excitation pulse;
  v. Hyperspectral pulse;
  vi. Green pulse;
  vii. Red pulse;
  viii. Blue pulse;
  ix. Fluorescence excitation pulse;
  x. Hyperspectral pulse;
  xi. Laser mapping pulsing scheme;
  xii. (Repeat)

An embodiment may comprise a pulse cycle pattern as follows:
  i. Luminance pulse;
  ii. Red chrominance pulse;
  iii. Luminance pulse;
  iv. Blue chrominance pulse;
  v. Hyperspectral pulse;
  vi. Fluorescence excitation pulse;
  vii. Laser mapping pulse;
  viii. (Repeat)

An embodiment may comprise a pulse cycle pattern as follows:
  i. Luminance pulse;
  ii. Red chrominance pulse;
  iii. Luminance pulse;
  iv. Blue chrominance pulse;
  v. Luminance pulse;
  vi. Red chrominance pulse;
  vii. Luminance pulse;
  viii. Blue chrominance pulse;
  ix. Hyperspectral pulse;
  x. Fluorescence excitation pulse;
  xi. Laser mapping pulse;
  xii. (Repeat)

The pulsing pattern may be altered to suit the imaging objectives for a specific implementation. An example imaging objective is to obtain hyperspectral imaging data and fluorescence imaging data, and further to obtain laser mapping and/or tool tracking data that is based on analysis of the hyperspectral and/or fluorescence imaging data. In such an example, the laser mapping and/or tool tracking data may be analyzed for certain areas of a scene that have been highlighted by the hyperspectral and/or fluorescence imaging data. A further example imaging objective is to obtain hyperspectral imaging data or fluorescence imaging data, and further to obtain laser mapping and/or tool tracking data. A further example imaging objective is to obtain laser mapping and/or tool tracking data. A further example imaging objective is to obtain hyperspectral imaging data. A further example imaging objective is to obtain fluorescence imaging data. It should be appreciated that the imaging objective may be specialized depending on the reason for deploying the imaging system. Additionally, the imaging objective may change during a single imaging session, and the pulsing pattern may be altered to match the changing imaging objectives.

As can be seen in the example, a laser mapping partition may be pulsed at a rate differing from the rates of the other partition pulses. This may be done to emphasize a certain aspect of the scene, with the laser mapping data simply being overlaid with the other data in the video output to make the desired emphasis. It should be noted that the addition of a laser mapping partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (laser mapping in the above example), would result in an increase of less than 20% of the cycling speed of the sensor to accommodate the irregular partition sampling.

In various embodiments, the pulse cycle pattern may further include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
  i. 770±20 nm;
  ii. 770±10 nm;
  iii. 770±5 nm;
  iv. 790±20 nm;
  v. 790±10 nm;
  vi. 790±5 nm;
  vii. 795±20 nm;
  viii. 795±10 nm;
  ix. 795±5 nm;
  x. 815±20 nm;
  xi. 815±10 nm;
  xii. 815±5 nm;
  xiii. 770 nm to 790 nm; and/or
  xiv. 795 nm to 815 nm.

In various embodiments, the pulse cycle may further include any of the following wavelengths in any suitable order. Such wavelengths may be particularly suited for generating hyperspectral imaging data:
  i. 513 nm to 545 nm;
  ii. 565 nm to 585 nm;
  iii. 900 nm to 1000 nm;
  iv. 513±5 nm;
  v. 513±10 nm;
  vi. 513±20 nm;
  vii. 513±30 nm;
  viii. 513±35 nm;
  ix. 545±5 nm;
  x. 545±10 nm;
  xi. 545±20 nm;
  xii. 545±30 nm;
  xiii. 545±35 nm;
  xiv. 565±5 nm;
  xv. 565±10 nm;
  xvi. 565±20 nm;
  xvii. 565±30 nm;
  xviii. 565±35 nm;
  xix. 585±5 nm;
  xx. 585±10 nm;
  xxi. 585±20 nm;
  xxii. 585±30 nm;
  xxiii. 585±35 nm;
  xxiv. 900±5 nm;
  xxv. 900±10 nm;
  xxvi. 900±20 nm;
  xxvii. 900±30 nm;
  xxviii. 900±35 nm;
  xxix. 1000±5 nm;
  xxx. 1000±10 nm;
  xxxi. 1000±20 nm;
  xxxii. 1000±30 nm; or
  xxxiii. 1000±35 nm.

Figure 7A:
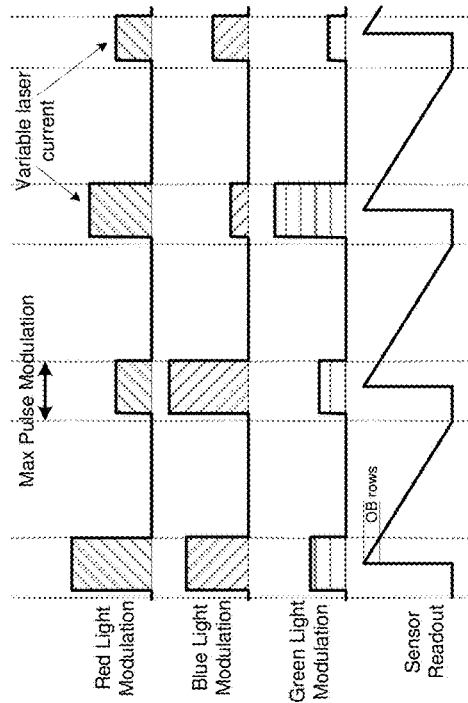
FIGS. 7A-7E illustrate schematic views of the processes over an interval of time for recording a frame of video for both full spectrum light and partitioned spectrum light.
Figure 7B:
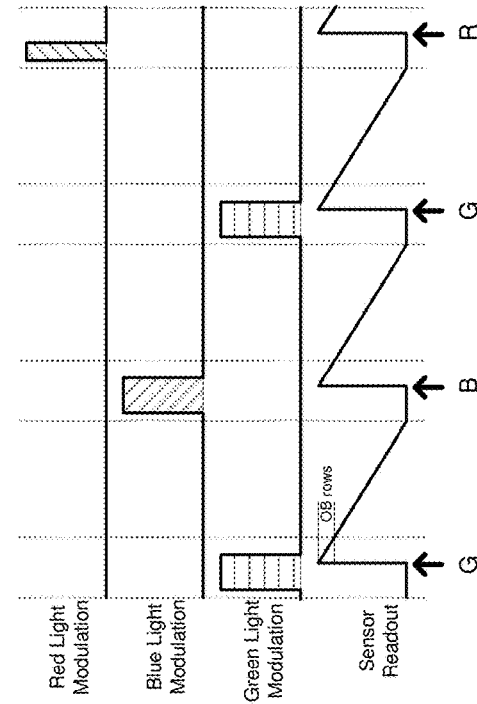
Figure 7C:
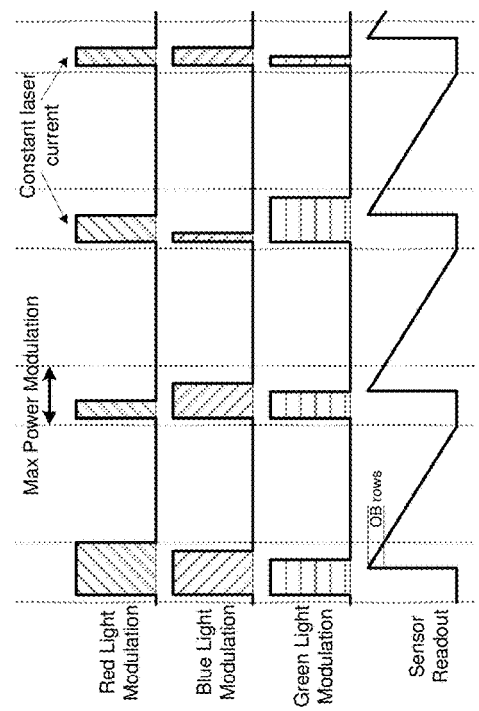

The partition cycles may be divided so as to accommodate or approximate various imaging and video standards. In an embodiment, the partition cycles may comprise pulses of electromagnetic energy in the Red, Green, and Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

In an embodiment, the emitter emits one or more hyperspectral emissions for eliciting a spectral response. The hyperspectral emissions include one or more of electromagnetic radiation having a wavelength from about 513-545 nm, from about 565-585 nm, and/or from about 900-1000 nm. In such an embodiment, the coherent light source 802 includes at least one laser emitter for the 513-545 nm partition, at least one laser emitter for the 565-585 partition, and at least one laser emitter for the 900-1000 nm partition. It should be appreciated that additional hyperspectral emissions for eliciting a spectral response can be emitted without departing from the scope of the disclosure.

In an embodiment, the emitter emits one or more fluorescence excitation emissions for fluorescing a reagent. The fluorescence excitation emissions include one or more of electromagnetic radiation having a wavelength from about 460-470 nm, 529-537 nm. 633-643 nm, 775-785 nm, 800-810 nm, 970-980 nm, 575-579 nm, 519-527 nm, 770-790 nm, and/or 795-815 nm. In such an embodiment, the coherent light source 802 may include at least one laser emitter for each of the aforementioned partitions of electromagnetic radiation. It should be appreciated that additional fluorescence excitation emissions for fluorescing a reagent can be emitted without departing from the scope of the disclosure.

Figure 7D:
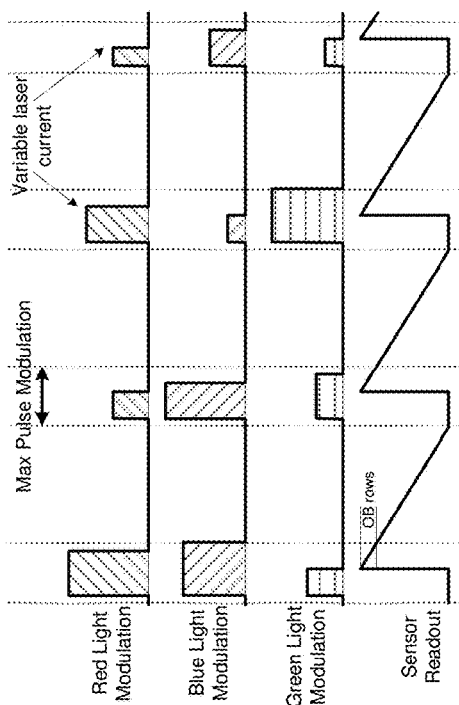

In an embodiment using color spaces Green-Blue-Green-Red (as seen in FIG. 7D) it may be desirous to pulse the luminance components more often than the chrominance components because users are generally more sensitive to light magnitude differences than to light color differences.

This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
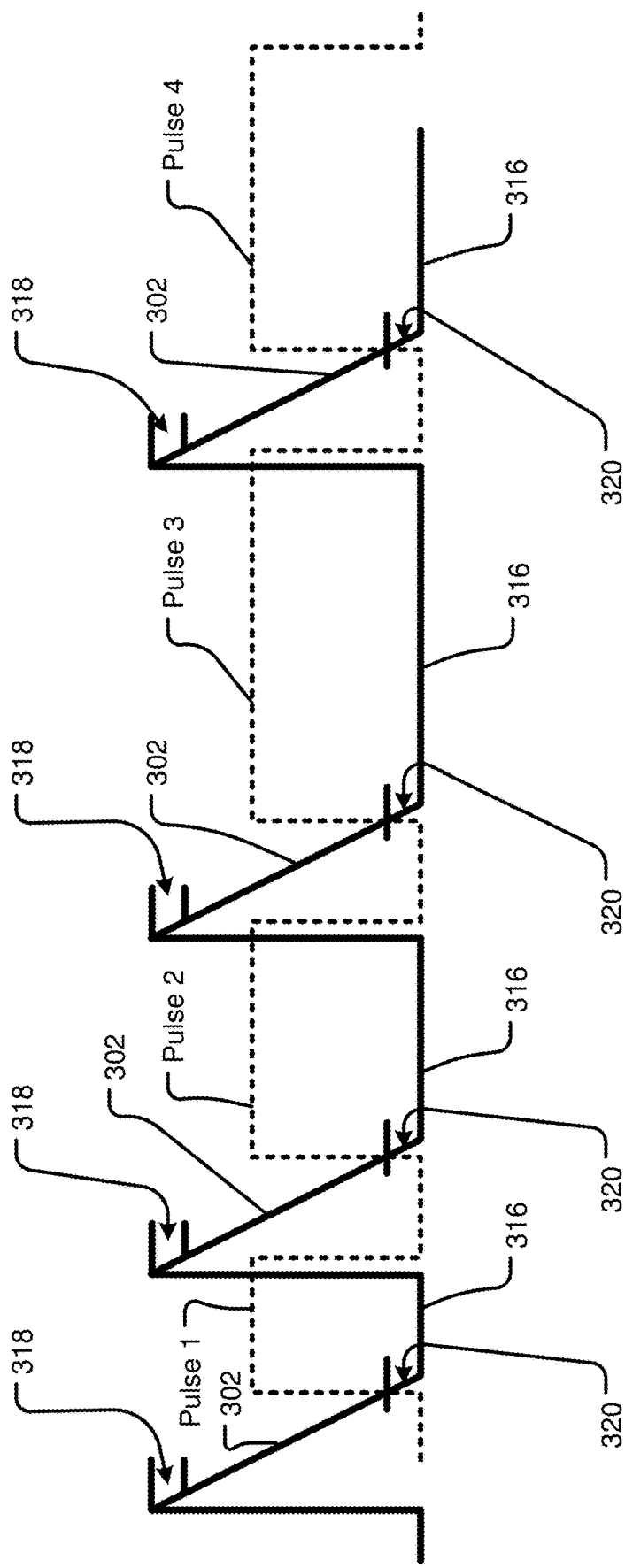

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking periods with a repeating pattern of two or three or four or n frames.

In FIG. 7E, four different light pulses are illustrated, and Pulse 1 may repeat for example after Pulse 4 and may have a pattern of four frames with different blanking periods. This technique can be used to place the most powerful partition on the smallest blanking period and therefore allow the weakest partition to have wider pulse on one of the next frames without the need of increasing the readout speed. The reconstructed frame can still have a regular pattern from frame to frame as it is constituted of many pulsed frames.

Figure 8:
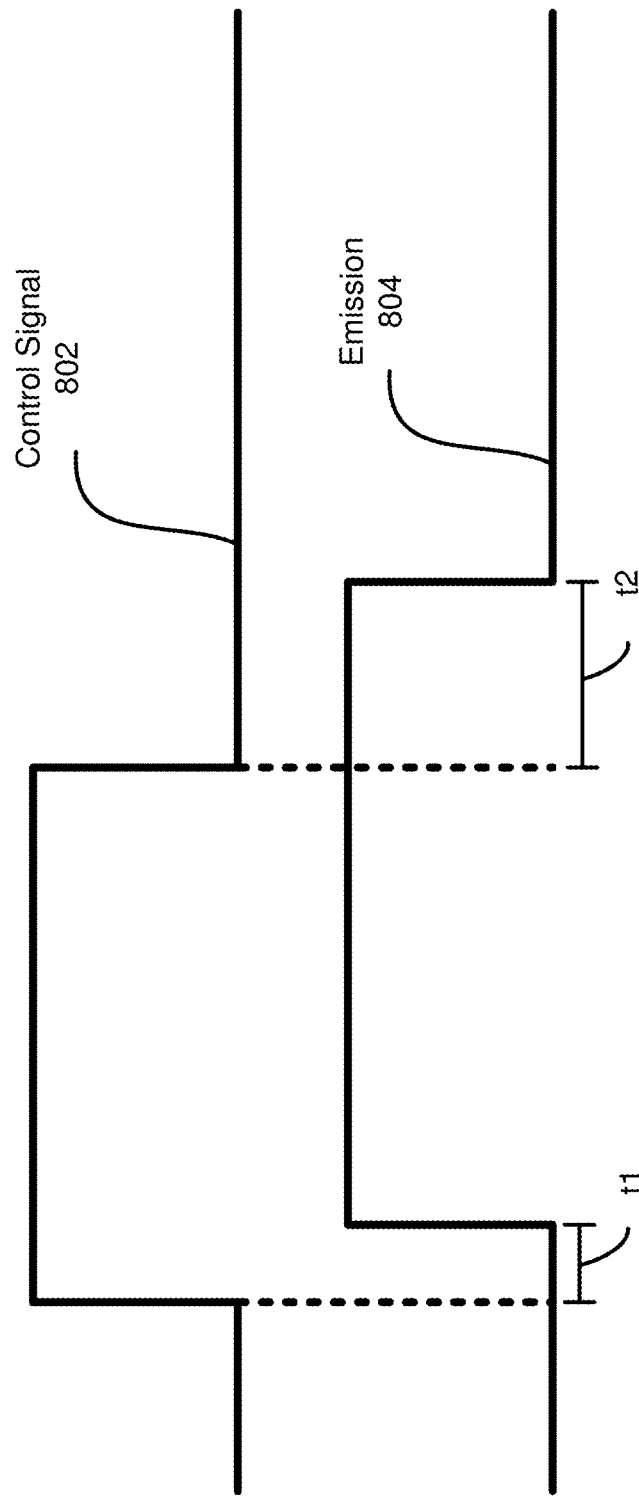
FIG. 8 is a graphical display of the delay or jitter between a control signal and an emission of electromagnetic radiation by an emitter.

FIG. 8 is a graphical display of the delay or jitter between a control signal 802 and an emission 804 of electromagnetic radiation. In an embodiment, the control signal 802 represents a signal provided to the driver of an emitter. The driver is configured to cause an emitter 102 to emit a pulse of electromagnetic radiation. In an embodiment, the driver is a component of a controller 124 or may be independent of the controller 124 and in communication with the controller 124. In an embodiment, the driver is the controller 124. In an embodiment, the driver is a component of the emitter 102 or is in communication with the emitter 102. As illustrated, there is a delay of duration t1 between the control signal 802 reaching its peak (i.e. turning on) and the emission 804 of electromagnetic radiation by an emitter 102. There is a delay of duration t2 between the control signal 802 going low (i.e. turning off) and the end of the emission 804 of electromagnetic radiation.

The delays t1 and t2 may include some constant delay as well as some non-constant variation resulting from jitter in the driver of the emitter. For example, there may be a constant delay from when the control signal 802 is transmitted to the driver and when an emission 804 of electromagnetic radiation is actually emitted by the emitter 102. This delay may be very short and may be based on the time required for electrical communications to occur between the driver and the emitter. Non-constant variation in the delay may be a result of jitter in the driver of the emitter, in the controller 124, and or in the emitter itself.

The jitter experienced by a system or a component of a system (such as the driver of the emitter) may be described by a value referred to as the jitter specification. The jitter specification is a numerical value that describes the amount of jitter, or a duration of jitter, experienced by a system. In the example illustrated in FIG. 8, the delay t1 has a shorter duration than the delay t2. In the example, the delay t1 may represent the constant delay experienced after the control signal 802 is initiated and an emission 804 of electromagnetic radiation is emitted by the emitter. The difference between t2 and t1 may represent the jitter experienced by the system. This value may be referred to as the jitter specification.

In an embodiment, the jitter specification is a numerical value that represents the amount of variation in the constant or predictable delay for initiating or discontinuing an emission of a pulse of electromagnetic radiation. In such an embodiment, the system experiences a constant, predictable delay between a driver signaling to the emitter to emit a pulse of electromagnetic radiation and when the emitter actually initiates the pulse of electromagnetic radiation. Similarly, there may be a constant, predictable delay between when the emitter should discontinue the pulse of electromagnetic radiation and when the emitter actually discontinues the pulse of electromagnetic radiation. This constant, predictable delay does not represent the jitter specification. Instead, the jitter specification is the variation in this constant, predictable delay. In the example illustrated in FIG. 8, the difference between times t2 and t1 represents the variation in the constant, predictable delay.

Jitter is not under control by a user of the system. The jitter specification represents the amount of unpredictable and non-constant time variation present in the system. If the jitter specification is too large with respect to a pulse of electromagnetic radiation, significant reductions in image quality or image brightness variations can occur in the resulting exposure frames. For example, in a video endoscopic system as discussed herein, a long jitter specification can cause different lines of exposure frames within a video stream to have different brightness. This leads to flickering and overall reduced quality in the video stream. A long jitter specification may result in light being emitted during a readout period 302 of the image sensor. If electromagnetic radiation is pulsed during the readout period 302, significant variations between pixels and rows of pixels in the pixel readout will occur and this will reduce image quality in the resultant video stream.

In an example implementation, the controller 124 has a jitter specification of 10% of the duration of a pulse of electromagnetic radiation. In the example, the pulse may vary from 90% of its desired duration to 110% of its desired duration. This can lead to brightness variations between exposure frames or lines within an image frame of a video of up to one-third.

In an embodiment, if the jitter specification has a duration longer than a threshold amount, then the pulses of electromagnetic radiation are limited in duration to avoid overlapping into a readout period 302. Limits on the pulse duration may require a reduction in frame rate by increasing the time between captured exposure frames and/or increasing the duration of the blanking period 316. This may result in a reduction to image brightness, and this may further reduce the ability of the image sensor to capture detailed images.

In an embodiment, if the jitter specification has a duration shorter than a threshold amount, then the pulsing sequence of the emitter 102 and the readout sequence 204 of the image sensor remain unchanged. In an embodiment, the threshold indicates that the jitter specification must be 1 microsecond or less. In an embodiment, the threshold indicates that the jitter specification must be 50 nanoseconds or less. In an embodiment, the threshold indicates that the jitter specification must be less than the time it takes for the image sensor to read out one line of the pixel array. In an embodiment, the threshold indicates that the jitter specification must be less than the time it takes for the image sensor to read out a single pixel of the pixel array. In an embodiment, the threshold indicates that the jitter specification may be less than or equal to 10% to 25% of the readout period 302 of the image sensor, or the time it takes the image sensor to read out all active pixels in the pixel array. For example, in such an embodiment, if the pixel array comprises 400 lines, then the jitter specification must be less than or equal to the time required to read out 40-100 lines of the 400 lines in the pixel array. Thus, the amount of variation in the light captured by the pixel array may be low enough to reduce image flicked and provide as much light as possible between readout periods 302.

In an embodiment, the jitter specification is reduced (shortened) by implementing a higher clock rate or a more accurate clock in the controller 124 or the driver of the emitter 102. The reduced jitter specification and tolerance of the driver of the emitter 102 may solve the problem of non-tolerated driving causing artifacts in the resultant video stream.

In an embodiment, a camera control unit (CCU) provides signals to a controller 124 or an emitter 102 to avoid overlapping a pulse of electromagnetic radiation with the readout period 302 of the image sensor. The CCU may determine a timing for sending a signal to the controller 124 and/or the emitter 102 to avoid overlapping into the readout of active (i.e., not optical black) pixels of the pixel array. The CCU may maximize the duration of time electromagnetic radiation is emitted by the emitter 102 without overlapping a readout period 302 of the image sensor.

Figure 9:
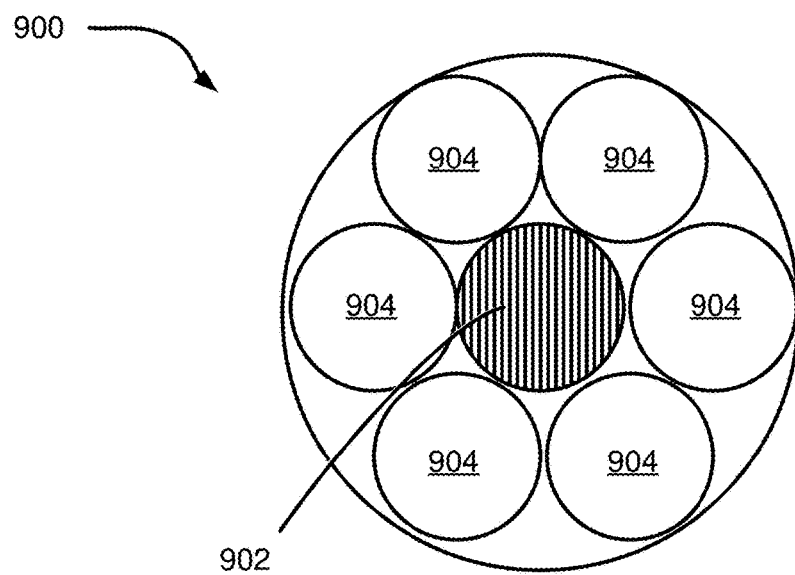
FIG. 9 is a cross-sectional view of an optical fiber bundle comprising a center fiber and a plurality of surrounding fibers.

FIG. 9 illustrates a cross section of an optical fiber bundle 900 for carrying electromagnetic radiation from an emitter 102 to a light deficient environment for illuminating a scene. In the example embodiment illustrated in FIG. 9, the optical fiber bundle 900 includes seven fibers, but it should be appreciated that the number of fibers is illustrative only and any suitable number of fibers may be used with departing from the scope of the disclosure. The fiber bundle includes a center fiber 902 and multiple surrounding fibers 904.

In an embodiment, the total number of fibers is limited to reduce the cross-sectional area of the optical fiber bundle 900. The optical fiber bundle 900 may include a suitable number of fibers for providing sufficient light dispersion while allowing for a small cross-sectional area. This may be desirable because the cross-sectional rea of the lumen of an endoscopic is of critical importance in some applications where a small endoscope is necessary. In an embodiment, the optical fiber bundle 900 includes from two to 150 fibers. A smaller number of fibers may reduce expense and the cross-sectional area needed to carry the optical fiber bundle 900. However, a greater number of fibers improves redundancy. In an embodiment, the optical fiber bundle 900 includes 5-100 fibers, or 5-50 fibers, or 7-15 fibers. In an embodiment, the optical fiber bundle includes seven fibers as illustrated in FIG. 9.

When the optical fiber bundle 900 has a smaller number of fibers, it may be desirable that each fiber receives the same amount of electromagnetic radiation and the same amount of a specific wavelength of electromagnetic radiation. For example, if electromagnetic radiation is primarily transmitted through the center fiber 902, then the center fiber 902 will receive a majority of the electromagnetic radiation and the scene will be unevenly illuminated by color or brightness. Additionally, if more light enters into one fiber than another, the overall amount of electromagnetic radiation (power) that can be carried in the optical fiber bundle 900 may be reduced. For example, a fiber may have a burnout limit that may result in the fiber melting or otherwise becoming inoperative if electromagnetic radiation above a certain energy level or intensity is provided to the fiber. Thus, if electromagnetic radiation is more evenly distributed across the fibers, then an increase in power and illumination of the scene may be possible.

In an embodiment, an emitter 102 mixes two or more wavelengths of electromagnetic radiation before providing the electromagnetic radiation to the optical fiber bundle 900. This may be accomplished when the emitter 102 includes two or more independent emitters for emitting different wavelengths of electromagnetic radiation. The emitter 102 may include, for example, a first emitter for emitting a first wavelength and a second emitter for emitting a second wavelength. The emitter 102 may mix the electromagnetic radiation such that light from the first emitter and the second emitter enter the jumper waveguide (or another waveguide) at the same or substantially same angle. A same or substantially same angle may be achieved by positioning the emitters at the same angle relative to one another. In an embodiment, a dichroic mirror allows for a same or substantially same angle by reflecting electromagnetic radiation of one wavelength while being transparent to another wavelength. In an embodiment, the emitter 102 includes a diffuser, mixing rod, lens, or other optical element to mix light before entry into the optical fiber bundle 900.

In an embodiment, the emitter 102 provides an evenly distributed light intensity to a waveguide. The peak intensity of light within a region where light is collected for the waveguide may be substantially the same or close to the average intensity of light over the region. The light provided to a collection region may have a top hat profile such that each fiber collects and/or receives the same or similar intensity of light. The emitter 102 may provide or approximate a top hat profile by providing laser light at an angle to a surface of a collection region. For example, the emitter 102 may include a Gaussian or other non-constant intensity profile. By angling the emitters in relation to the collection region, the Gaussian profile is flattened into a more constant or top hat profile. The top hat profile may be generated using lenses, diffusers, mixing rods, and the like.

Figure 10:
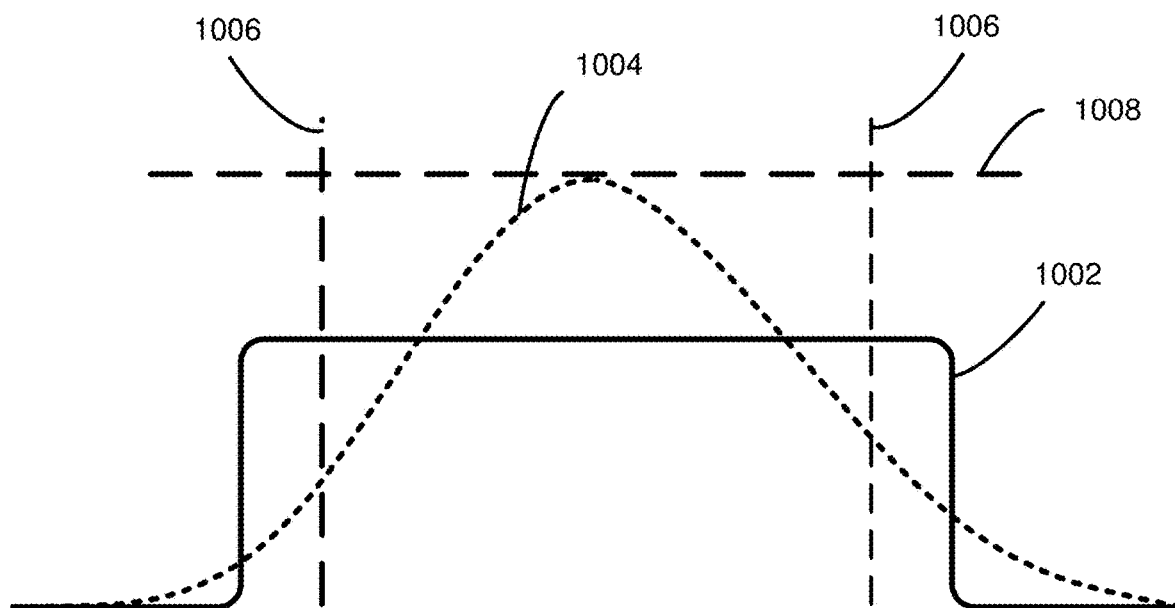
FIG. 10 is a graphical display of a top hat profile and a Gaussian profile for sending electromagnetic radiation to an optical fiber bundle.

FIG. 10 graphically illustrates a top hat profile 1002 and a Gaussian profile 1004. The horizontal axis represents horizontal distance and the vertical axis represents light intensity. The lines labeled with callout 1006 represent the boundaries or width of a collection region 1006 of the optical fiber bundle 900. The line labeled with the callout 1008 represents a burnout level 1008 for a fiber or other waveguide.

With the Gaussian profile 1004, a majority of the electromagnetic radiation is sent to the center fiber 902. When the majority of the energy is in the center fiber 902, the remaining surrounding fibers 904 may be far below the burnout level 1008. For example, with the Gaussian profile 1004, an increase in the total amount of energy could lead to a center fiber 902 significantly exceeding the burnout level 1008 with the multiple surround fibers 904 far below the burnout level 1008.

With the top hat profile 1002, all fibers carry the same energy level. This energy level may be near the burnout level 1008 or below the burnout level 1008. For example, with the top hat profile 1002, the total energy carried by the optical fiber bundle 900 may be significantly increased because the optical fiber bundle 900 may collectively be pushed near the burnout level 1008 without risking burnout of any individual fiber.

FIG. 10 illustrates that more energy can be provided before any of the individual fibers reach the burnout level 1008 by implementing the top hat profile 1002. In some instances, in traditional systems, the output light cone is smaller than the field of view (FOV) of the image sensor. The area of the output light cone is typically limited by the numerical aperture of the optical fiber of the waveguide. In these traditional systems, the distribution of light intensity within the output light cone has an approximately Gaussian profile 1004. When the light output has a Gaussian profile 1004, the center of the image sensor's field of view will be too bright and the edges of the image sensor's field of view will be too dark. Therefore, it is desirable to provide even light distribution such that the entire field of view of the image sensor is uniform or nearly uniform.

The Gaussian profile 1004 and the top hat profile 1002 may provide the same amount of wattage to the optical fiber bundle 900, while the top hat profile 1002 can still be increased significantly before reaching the burnout level 1008. Thus, a significant improvement in the total amount of energy delivered using plastic fibers can be achieved. In some cases, a 50% or greater increase of wattage carried by an optical fiber bundle 900 may be achieved by implementing the top hat profile 1002. In an embodiment, the plastic fibers may have a burnout energy level for light/electromagnetic energy emitted by the one or more emitters above which damage to the plastic fibers may occur, wherein the light energy is spread out across the plurality of plastic fibers to allow a greater amount of energy to be carried by the optical fiber bundle 900 including the plastic fibers without reaching the burnout level 1008 in any of the fibers.

In an embodiment, the top hat profile 1002 and the Gaussian profile 1004 are combined by an emitter 102 for use with plastic optical fiber bundles 900. The emitter 102 and/or the jumper waveguide may not include plastic waveguides. However, the emitter 102 may mix the top hat profile 1002 with the Gaussian profile 1004 to allow for use with a plastic optical fiber bundle 900 at the lumen waveguide. In an embodiment, mixing the top hat profile 1002 allows for greater power delivery in view of losses that may be incurred when moving the electromagnetic radiation between different materials, e.g. from a diffuser to a glass fiber, to a plastic fiber, and/or back to a glass fiber or diffuser. The greater power delivery may offset losses in previous or subsequent transitions so that sufficient light can still be delivered to illuminate a scene.

Figure 11:
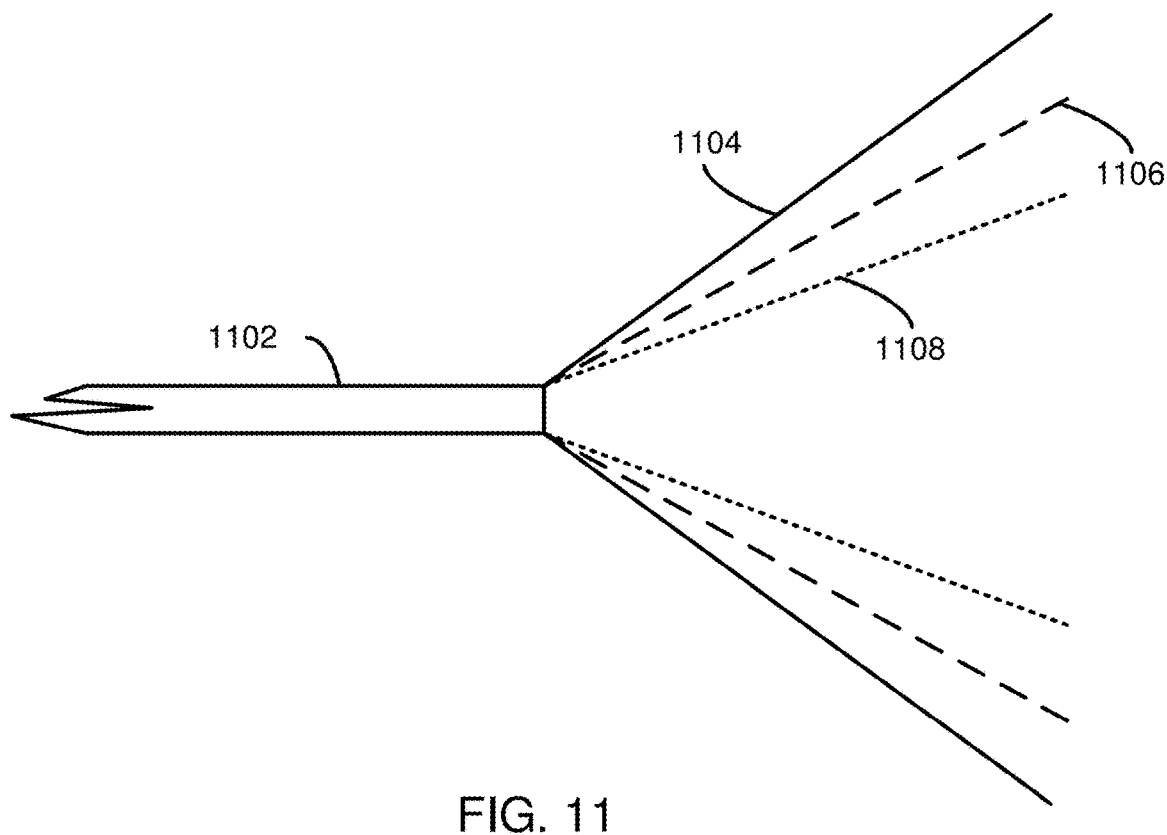
FIG. 11 is a side view illustrating the output of electromagnetic radiation (light) from an optical fiber bundle in comparison to the field of view of a camera.

FIG. 11 is a side view illustrating output from a waveguide 1102 in comparison to a camera field of view. In an embodiment, a plastic fiber has a numerical aperture of 0.63 with a field of view of 100 degrees as indicated by dashed line 1106. A glass fiber has a numerical aperture of 0.87 with a field of view of 120 degrees as indicated by solid line 1104. However, light emitted within the field of view has an approximate Gaussian profile within a light cone that is less than the field of view. For example, nearly all the light for a plastic fiber may be within a cone of 80 degrees as indicated by dotted line 1108. Thus, a center region of an exposure frame may be too bright while the edges are too dark.

Figure 12:
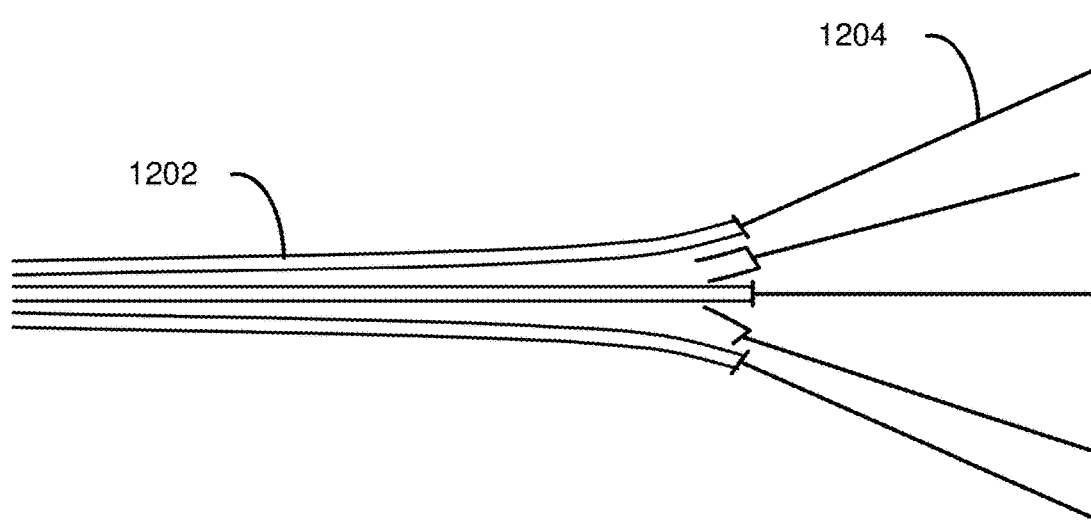
FIG. 12 is a side view illustrating the output of electromagnetic radiation from an optical fiber bundle wherein the ends of individual fibers are aimed to provide more uniform distribution of the electromagnetic radiation.

FIG. 12 is a side view illustrating output from a waveguide comprising an optical fiber bundle 1202 having a more uniform distribution of light relative to the output illustrated in FIG. 11. In the embodiment illustrated in FIG. 12, a uniform distribution of light is achieved by aiming the ends of fibers where light exits the optical fiber bundle 1202. Aiming the fibers away from center broadens the cone in a field of view with no light loss at the output. The end of each fiber may be held in a desired position to distribute light where the combination of light cones from the fibers provides even illumination. The optical fiber bundle 1202 includes a plurality of fibers and lines 1204 that indicate the orientation of cones output by the individual fibers. In an embodiment, a fixture such as a physical mold or a sheet with holes holds the ends of the fibers in the desired orientations. The fibers may be oriented in an optimal orientation for even illumination of a scene. The tips of the fibers in the optical fiber bundle 1202 may be located near a distal tip of an endoscope and may be pointed to spread light around a region centered on the focal point or camera lens axis.

Figure 13:
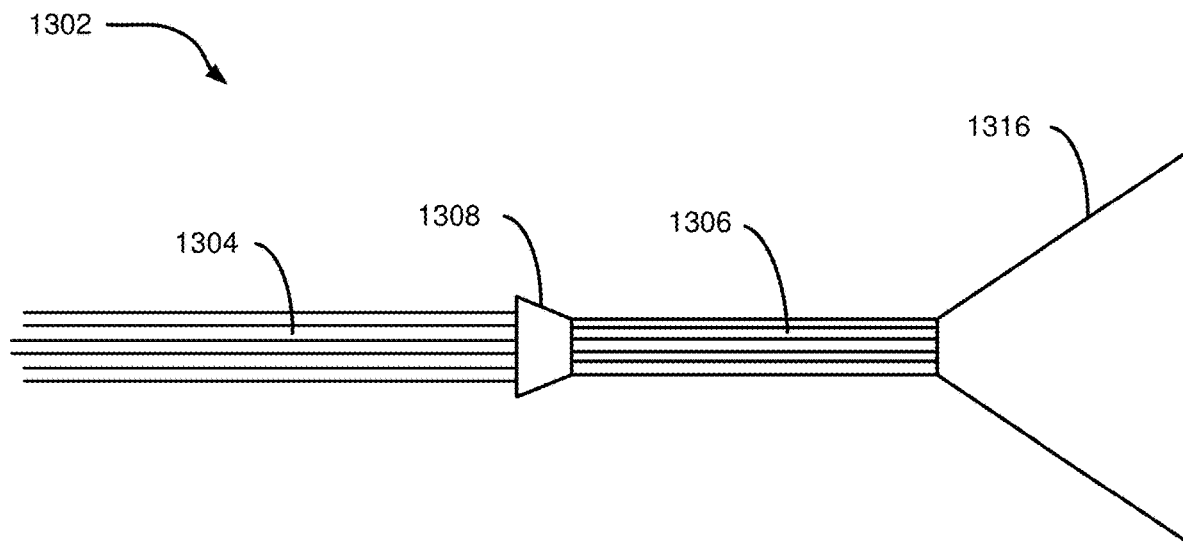
FIG. 13 is a side view illustrating the output of electromagnetic radiation from an optical fiber bundle, wherein the optical fiber bundle comprises plastic fibers and glass fibers coupled near the output.

FIG. 13 is a side view illustrating output from a waveguide comprising an optical fiber bundle 1302 that transitions from plastic fibers 1304 to glass fibers 1306 at a connector 1308. In the embodiment, a lumen waveguide includes plastic fibers 1304 and then transitions to glass fibers 1306 at or near an output. The glass fibers 1306 generally have a higher numerical aperture and a wider field of view than the plastic fibers 1304. Thus, a wider and more even distribution of light energy is achieved as illustrated by the light cone 1316. The light traveling through the plastic fibers 1304 is guided to the glass fibers 1306 by way of the connector 1308. This coupling may occur within a handpiece unit of an endoscope or a lumen of the endoscope. The connector 1308 may be positioned in the handpiece unit or in the lumen to limit the amount of glass fibers 1306 used. Moving from plastic fibers 1304 through a taper in the handpiece or the lumen to glass fibers 1306 may result in the same field of view as a conventional endoscope. However, light loss may be significant, such as about 25% compared to the aiming embodiment, which experiences no light loss at the output.

Figure 14:
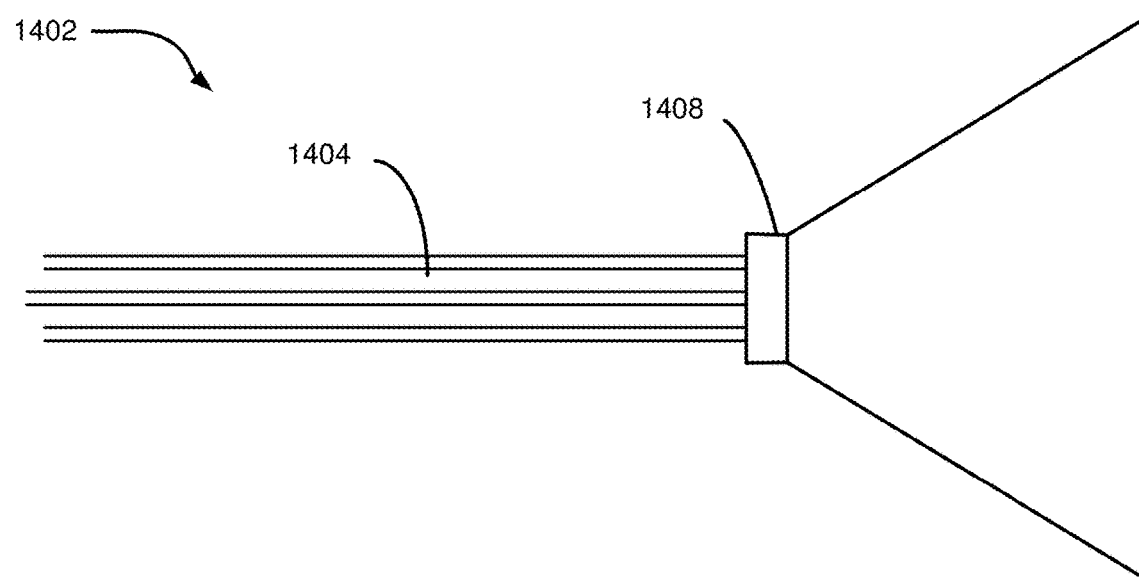
FIG. 14 is a side view illustrating the output of electromagnetic radiation from an optical fiber bundle comprising a diffuser located near the output.

FIG. 14 is a side view illustrating light output from a waveguide comprising an optical fiber bundle 1402 using a diffuser 1408. In the embodiment, a lumen waveguide includes plastic fibers 1404 and then transitions to the diffuser 1408 at or near an output. The diffuser 1408 may include any suitable optical diffuser such as a mixing rod or the like. Example diffusers include holographic diffusers. The diffuser 1408 at the output can produce a larger angle for the field of view when compared against glass fibers. However, the diffuser 1408 is less efficient, such as about 40-60% efficient versus the aiming embodiment illustrated in FIG. 12.

Plastic fibers are typically less expensive than glass fibers. The reduced price can lead to significant savings in manufacturing the illumination system. Because glass fibers may only be used for a short distance near an output, or not at all, a significant cost savings is realized.

In an embodiment, a single fiber replaces an optical fiber bundle as the waveguide. The single fiber may be larger than typical fibers making up the optical fiber bundle such that the single fiber is capable of handling a greater amount of power than a bundle of smaller fibers for the same cross-sectional area. The single fiber may extend from a console and through a lumen to provide light to an interior of a body or other light deficient environment. The single fiber may operate as a lumen waveguide that extends from the emitter 102 or jumper waveguide and through a lumen. Electromagnetic radiation may be provided by the emitter 102 directly to the single fiber with the top hat profile.

Because a plastic fiber may only have a numerical aperture of 0.63 or 0.65, most of the electromagnetic radiation may only exit the fiber at an angle of 70 or 80 degrees. At an output of the single fiber, a diffuser may be positioned to spread output light and create a more even illumination within a field of the view of the camera. In an embodiment, the type of diffuser or the presence of a diffuser may be based on the field of view used by the camera. For example, laparoscopic procedures may allow for more narrow fields of view, such as 70 degrees, while arthroscopic procedures may use broader fields of view, such as 110 degrees. Thus, a diffuser may be used for arthroscopic examinations while a diffuser is absent for laparoscopic examinations.

It should be understood that embodiments for outputting electromagnetic radiation (light) may include a combination of one or more of the embodiments illustrated in FIGS. 11-14. For example, plastic fibers may be transitioned to glass fibers and the glass fibers may be aimed to provide more uniform and improved illumination.

Figure 15:
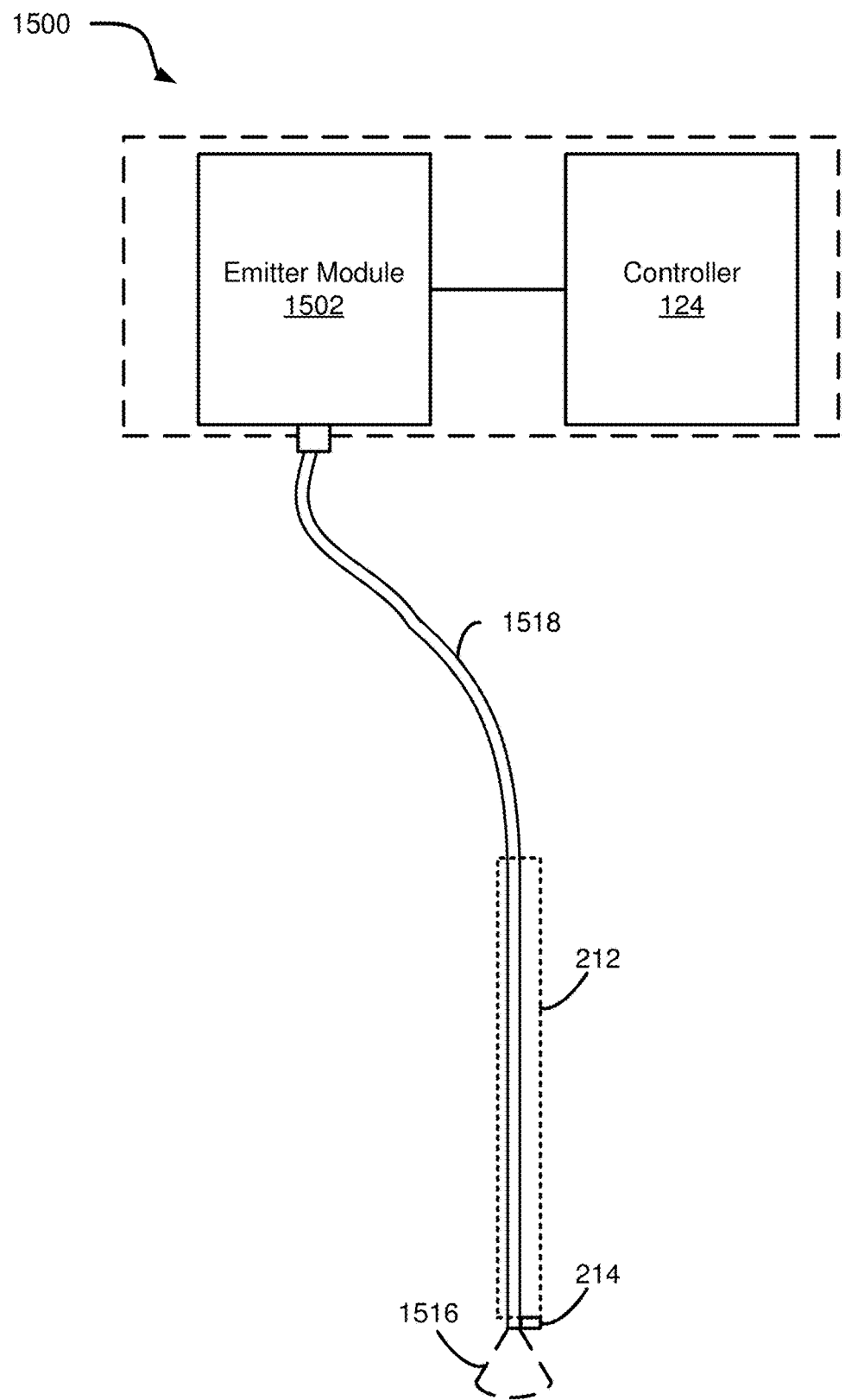
FIG. 15 is a system for providing illumination to a light deficient environment for endoscopic imaging.

FIG. 15 is a schematic diagram illustrating an example embodiment of a system 1500 for providing illumination to a light deficient environment, such as for endoscopic imaging. The system 1500 illustrates an alternative embodiment of transmitting light from the emitter module 1502 to the endoscope 212 compared with the embodiment illustrated in the system 200 of FIG. 2. The system 1500 includes an emitter module 1502, a controller 124, a waveguide 1518, an endoscope 212, and an image sensor 214 with accompanying optical components. In one embodiment, the emitter module 1502 and/or the controller 124 may be located in a console or camera control unit to which the endoscope 212 may be attached. The waveguide 1518 communicates electromagnetic radiation from the emitter module 1502 to the emitter 212 and may further communicate electromagnetic radiation to the distal end of the endoscope 212 where the image sensor 214 is located.

Emissions of electromagnetic radiation exit the emitter module 1502 and these emissions are provided into the waveguide 1518. The electromagnetic radiation travels through the waveguide 1518 to illuminate a scene at a distal end of the endoscope 212. The endoscope 212 may be inserted into a patient's body for imaging, such as during a procedure or examination. The electromagnetic radiation is output in a light cone 1516 formation as illustrated by dashed lines. A scene illuminated by the electromagnetic radiation may be captured using the image sensor 214 and displayed for a doctor or some other medical personnel.

The emitter module 1502 generates and pulses electromagnetic radiation. The emitter module 1502 may include one or more emitters. In an embodiment, the emitter module 1502 includes a plurality of emitters such that the plurality of emitters may collectively pulse a range of wavelengths of electromagnetic radiation. In an embodiment, each emitter within the emitter module 1502 is capable of pulsing one partition of the electromagnetic radiation and the emitter module 1502 includes a plurality of emitters for pulsing a plurality of wavelengths of electromagnetic radiation. As discussed herein, the term "emitter" may refer to any of the independent emitters within the emitter module 1502 or may collectively refer to the emitter module 1502 itself. Therefore, the term "emitter" as used herein may refer to one or more individual laser emitter units, a collection of a plurality of laser emitter units, and an emitter module 1502.

One or more emitters within the emitter module 1502 pulse electromagnetic radiation. The electromagnetic radiation exits the emitter module 1502 and is provided into the waveguide 1518. In an embodiment, an optical fiber is attached to each of the independent emitters within the emitter module 1502, and these optical fibers are fed into the waveguide 1518. The waveguide 1518 may include one or more optical fibers for carrying electromagnetic radiation from the emitter module 1502. The waveguide 1518 may include one or more of the embodiments included herein, such as the embodiments illustrated in FIGS. 11-14. As discussed herein, the term "waveguide" may refer collectively to the jumper waveguide 206 and the lumen waveguide 210 illustrated in FIG. 2. The term "waveguide" may refer to either of the jumper waveguide 206 or the lumen waveguide 210 illustrated in FIG. 2. The term "waveguide" as used herein describes a component for carrying or transmitting light from one point to another point. As discussed with respect to FIG. 15, the waveguide 1518 transmits electromagnetic radiation from the emitter module 1502 to the endoscope 212 and/or the light deficient environment being illuminated by the distal end of the endoscope 212.

In an embodiment, the waveguide 1518 is a single optical fiber extending from the emitter module 1502, to the endoscope 212, through a lumen of the endoscope 212, and to the light deficient environment that is being captured by the image sensor 214. In such an embodiment of the waveguide 1518, the waveguide 1518 may be a single optical fiber with no interruptions extending from the emitter module 1502 to the distal end of the endoscope 212. In an embodiment where the waveguide 1518 is a single optical fiber rather than an optical fiber bundle (for example, the optical fiber bundle 900 illustrated in FIG. 9), the waveguide 1518 may have a diameter of about 500 microns. The waveguide 1518 may be a single plastic or glass optical fiber having a diameter of from about 400 microns to about 600 microns. The waveguide 1518 may be a single plastic or glass optical fiber having a diameter from about 450 microns to about 550 microns.

In an embodiment, the waveguide 1518 is a single optical fiber connected to the emitter module 1502 and then transitions to an optical fiber bundle at some point between the emitter module 1502 and the distal end of the endoscope 212. For example, the waveguide 1518 may be a single optical fiber at the connection point to the emitter module 1502, and then may transition to an optical fiber bundle at a waveguide connector (such as the waveguide connector 208 illustrated in FIG. 2), at a proximal end of the endoscope 212, at some point within the endoscope 212, or at a distal end of the endoscope 212. For example, the waveguide 1518 may transition from a single optical fiber to an optical fiber bundle at some point before the waveguide 1518 reaches the endoscope 212. For example, the waveguide 1518 may transition from a single optical fiber to an optical fiber bundle at some point within the endoscope 212, for example within the lumen of the endoscope 212. In an embodiment, the lumen includes a hollow rod that is disposed within a body for imaging the body, and the waveguide 1518 is disposed within the lumen along with other electrical components for supporting, for example, the image sensor 214 and other optical components of the system. For example, the waveguide 1518 may transition from a single optical fiber to an optical fiber bundle at a distal end of the endoscope 212 near the image sensor 214.

In an embodiment, the reverse of the preceding paragraph is true such that the waveguide 1518 is an optical fiber bundle connected to the emitter module 1502 and then transitions to a single optical fiber at some point between the emitter module 1502 and the distal end of the endoscope 212. It should be appreciated that the optical fiber bundle may transition to a single optical fiber at any suitable point between the emitter module 1502 and the distal end of the endoscope 212.

In some implementations, it may be desirable for the waveguide 1518 to consist of a single optical fiber rather than an optical fiber bundle. This may be the case where the emitter is pulsing high-energy pulses of electromagnetic radiation. A single optical fiber with a certain diameter may withstand a greater degree of energy than an optical fiber bundle that collectively has the same certain diameter. This is because of the individual optical fibers within the optical fiber bundle will have a smaller diameter and will therefore be more prone to failure when transmitting high-energy pulses of electromagnetic radiation. Particularly when optical fibers are constructed of plastic, optical fibers may be exceedingly fragile and may fail or melt when exposed to high degrees of energy.

In some implementations, it may be desirable for the waveguide 1518 to consist of an optical fiber bundle rather than a single optical fiber. An optical fiber bundle may have more longevity than a single optical fiber because the optical fiber bundle includes a plurality of backup optical fibers that can transmit electromagnetic radiation if one or more of the optical fibers fails or breaks. Optical fibers can be exceedingly fragile, and it can be beneficial to transmit electromagnetic radiation with more that one optical fiber at a time.

In some implementations, it may be desirable for the waveguide 1518 to include plastic optical fibers. In some alternate implementations, it may be desirable for the waveguide 1518 to include glass optical fibers. Glass optical fibers may emit electromagnetic radiation in a wider light cone 1516, and this may be beneficial when illuminating a light deficient environment such as an interior cavity of a body. The diameter of the light cone 1516 will also determine the size of the visible region within the light deficient environment. However, glass optical fibers are exceedingly fragile and are much more expensive than plastic optical fibers. In an embodiment, the waveguide 1518 includes one or more plastic optical fibers and a diffuser disposed at the end of the waveguide 1518. The diffuser may serve to widen the light cone 1516 of electromagnetic radiation exiting the waveguide 1518. In an embodiment, a waveguide 1518 consisting of one or more plastic optical fibers, in combination with a diffuser, may result in a wider light cone 1516 compared with glass optical fibers without a diffuser.

In one embodiment, the waveguide 1518 includes a single plastic optical fiber of about 500 microns. The plastic fiber may be low cost, but the width may allow the optical fiber to carry a sufficient amount of electromagnetic radiation to a scene, with coupling, diffuser, or other losses. In an embodiment, the waveguide 1518 includes a plurality of optical fibers. The waveguide 1518 may receive light directly from a connection to the emitter module 1502 or via a jumper waveguide (e.g., see the jumper waveguide 206 of FIG. 2). A diffuser may be used to broaden the light cone 1516 for a desired field of view of the image sensor 214 or other optical components.

Figure 16:
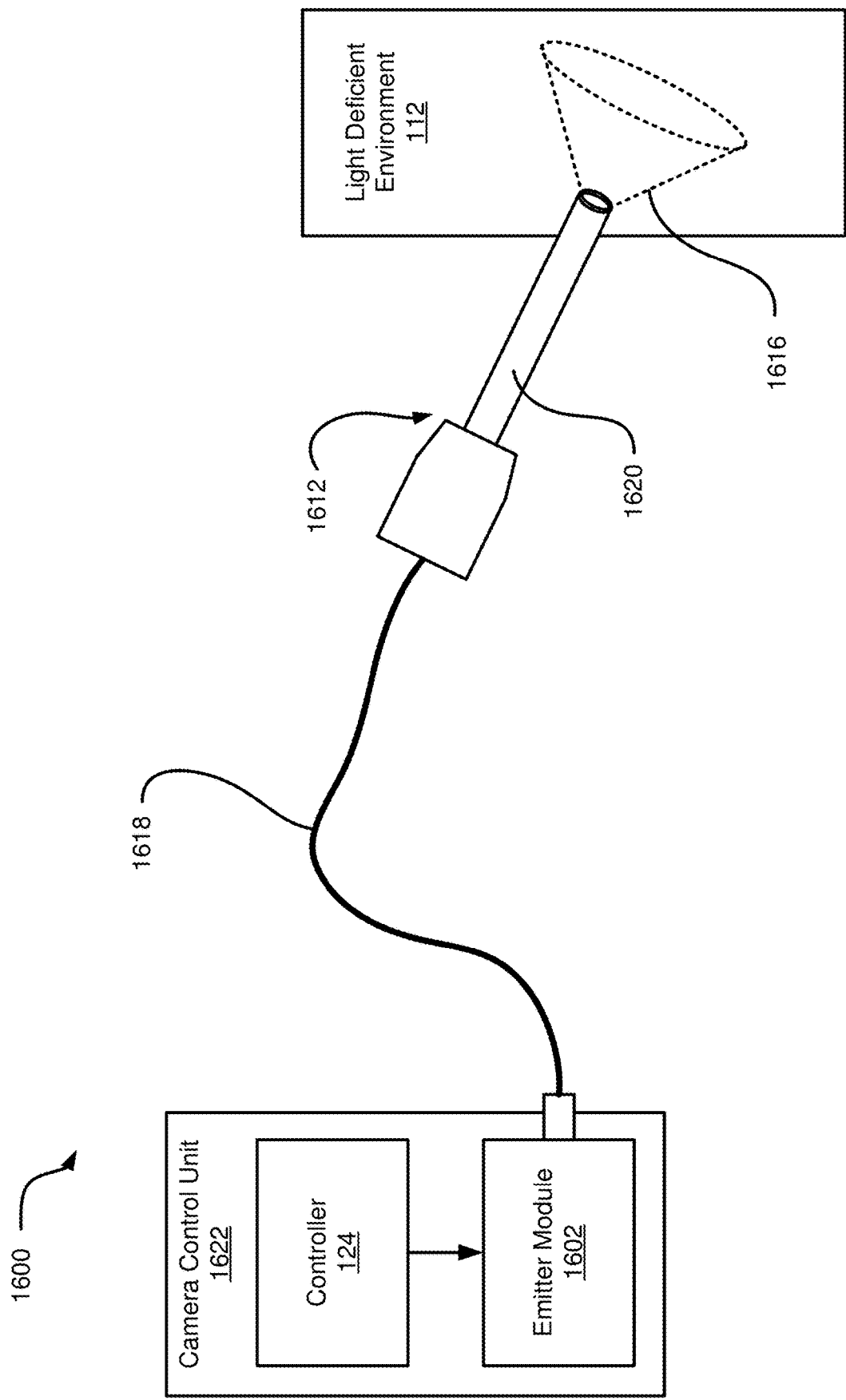
FIG. 16 is a system for providing illumination to a light deficient environment for endoscopic imaging.

FIG. 16 illustrates a system 1600 for providing electromagnetic radiation to a light deficient environment for endoscopic imaging. The system 1600 includes a camera control unit 1622 connected to an endoscope 1612. The camera control unit 1622 includes a controller 124 and an emitter module 1602. The emitter module 1602 includes one or more emitters for pulsing emissions of electromagnetic radiation. Emissions of electromagnetic radiation exit the emitter module 1602 and are provided to a waveguide 1618. The waveguide 1618 carries the emissions of electromagnetic radiation at least to the hand unit of the endoscope 1612 and may further carry the emissions of electromagnetic radiation to the distal end of the endoscope lumen 1620 for illuminating the light deficient environment 112.

The waveguide 1618 may consist of a continuous optical fiber or optical fiber bundle. The waveguide 1618 may include two or more sections of optical fiber(s) coupled together. The waveguide 1618 may include any of the embodiments disclosed herein, including those embodiments illustrated in FIGS. 11-14. In an embodiment, the waveguide 1618 is a continuous single optical fiber extending from the emitter module 1602 to the distal end of the endoscope lumen 1620. In an embodiment, the waveguide 1618 includes two or more sections of optical fiber(s) that are coupled together at some point between the emitter module 1602 and the distal end of the endoscope lumen 1620. In an embodiment, the waveguide 1618 includes a first portion extending from the emitter module 1602 to the endoscope 1612 (for example, the handpiece portion of the endoscope 1612). The first portion of the waveguide 1618 may then be coupled to a second portion beginning at the endoscope 1612 and terminating at the distal end of the endoscope lumen 1620.

The endoscope lumen 1620 is a component of the endoscope 1612. The distal end of the endoscope lumen 1620 may be inserted into the light deficient environment 112 for illuminating a scene. In an implementation, the distal end of the endoscope lumen 1620 is inserted into a body cavity by way of a small incision. In an embodiment, the image sensor is disposed at the distal end of the endoscope lumen 1620. Additionally, one or more optical fibers may terminate at the distal end of the endoscope lumen 1620 for illuminating the light deficient environment 112. The emissions of electromagnetic radiation exiting the optical fibers at the distal end of the endoscope lumen 1620 create a light cone 1616 of illumination for visualizing a scene within the light deficient environment 112.

In an embodiment, the waveguide 1618 constitutes a single optical fiber for carrying emissions of electromagnetic radiation from the emitter module 1602 to the distal end of the endoscope lumen 1620, which may be disposed within the light deficient environment 112. In an alternative embodiment, the waveguide 1618 includes an optical fiber bundle with a plurality of optical fibers. The waveguide 1618 may be protected by and inserted within a tube that extends from the exit point of the emitter module 1602 to a handpiece portion or other component of the endoscope 1612. The waveguide 1618 may be disposed within a flexible tubing, such as one constructed of plastic, rubber, silicone, or some other suitable material. The waveguide 1618 may extend from the emitter module 1602 to the distal end of the endoscope lumen 1620.

In an embodiment, the endoscope lumen 1620 includes a rigid tube with a cavity therein. The cavity within the endoscope lumen 1620 may be sized appropriately for housing electrical components for the image sensor, including components for communications between the image sensor and the camera control unit 1622. The cavity within the endoscope lumen 1620 may additionally include sufficient space for housing the waveguide 1618. In an embodiment, the waveguide 1618 is disposed within a peripheral cavity that surrounds an inner cavity, and the electrical components for the image sensor are disposed within the inner cavity, as illustrated in FIGS. 17A-17B.

Figure 17A:
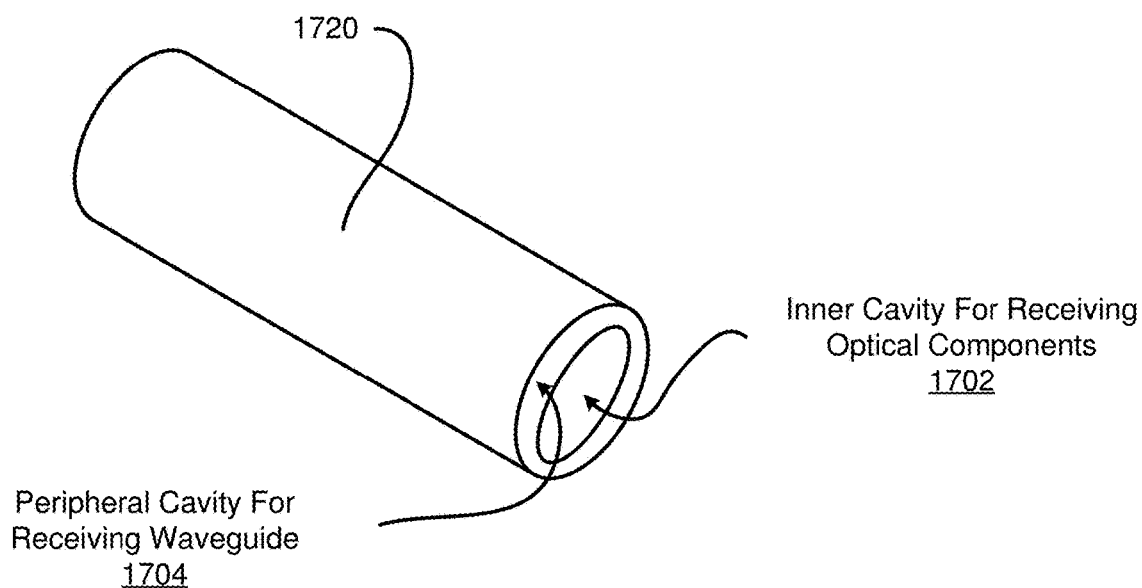
FIG. 17A is a perspective view of a portion of an endoscope lumen comprising an inner cavity for receiving optical components and a peripheral cavity for receiving a waveguide.
Figure 17B:
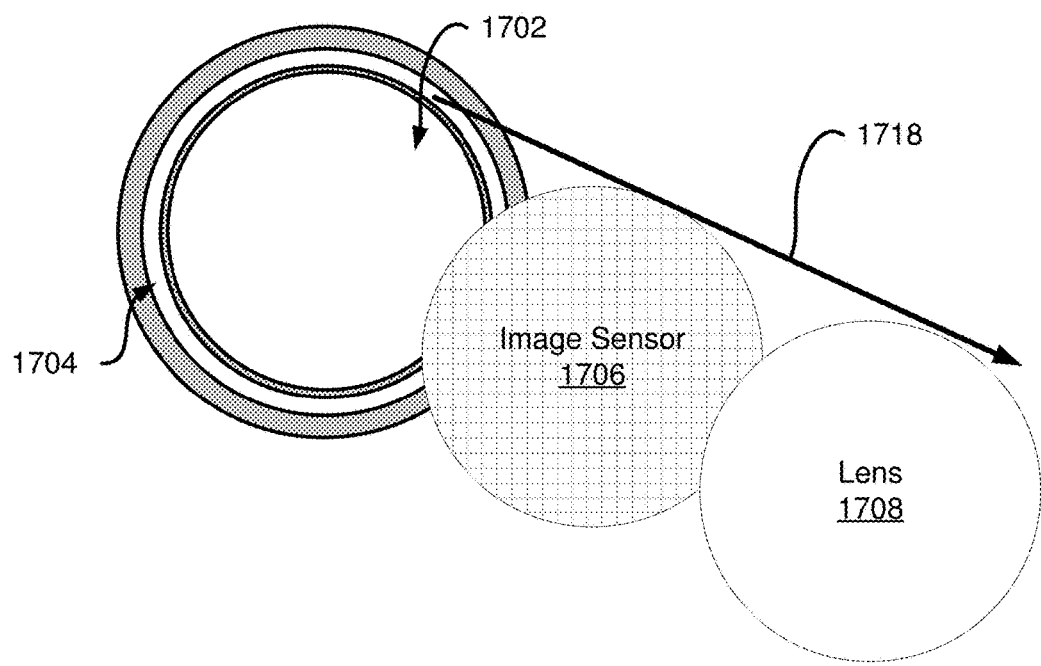
FIG. 17B is a straight-on view of a portion of an endoscope lumen comprising an inner cavity for receiving optical components including an image sensor and a peripheral cavity for receiving a waveguide.

FIGS. 17A and 17B illustrate an exemplary embodiment for disposing optical components and a waveguide within the endoscope lumen 1720. In an embodiment, the endoscope lumen 1720 is a rigid, flexible, or semi-flexible tube that may be inserted into the light deficient environment 112. The endoscope lumen 1720 may include an inner cavity 1702 wherein optical components may be located. The optical components may include wiring and other electrical connections for communications between the image sensor and/or the pixel array of the image sensor, and the controller 124 and/or camera control unit 1622. The endoscope lumen 1720 may additionally include a peripheral cavity 1704 for receiving the waveguide 1618. In an embodiment, the waveguide 1618 is a single optical fiber that may be disposed within the peripheral cavity 1704 along the length of the endoscope lumen 1720. In an embodiment, the waveguide 1618 is an optical fiber bundle comprising a plurality of optical fibers, and each of the plurality of optical fibers is disposed within the peripheral cavity 1704 along the length of the endoscope lumen 1720.

FIG. 17B illustrates a straight-on exploded view of the distal end of the endoscope lumen 1720 and the components disposed within or attached to the endoscope lumen 1720. In an embodiment, the image sensor 1706 is located at the distal end of the endoscope lumen 1720. The system may further include a lens 1708 located in front of the image sensor 1706 with respect to the scene being imaged by the image sensor 1706, such that the lens 1708 is the distal-most point of the endoscope lumen 1720. The waveguide 1718 may be disposed within the peripheral cavity 1704 and may terminate at the distal end of the endoscope lumen 1720 to illuminate a scene with pulses of electromagnetic radiation. The supporting electrical components for the image sensor 1706 may be stored within the inner cavity 1702 of the endoscope lumen 1720. In an embodiment, the waveguide 1718 extends past the distal-most point of the endoscope lumen 1720 to ensure proper illumination of the scene.

Figure 18:
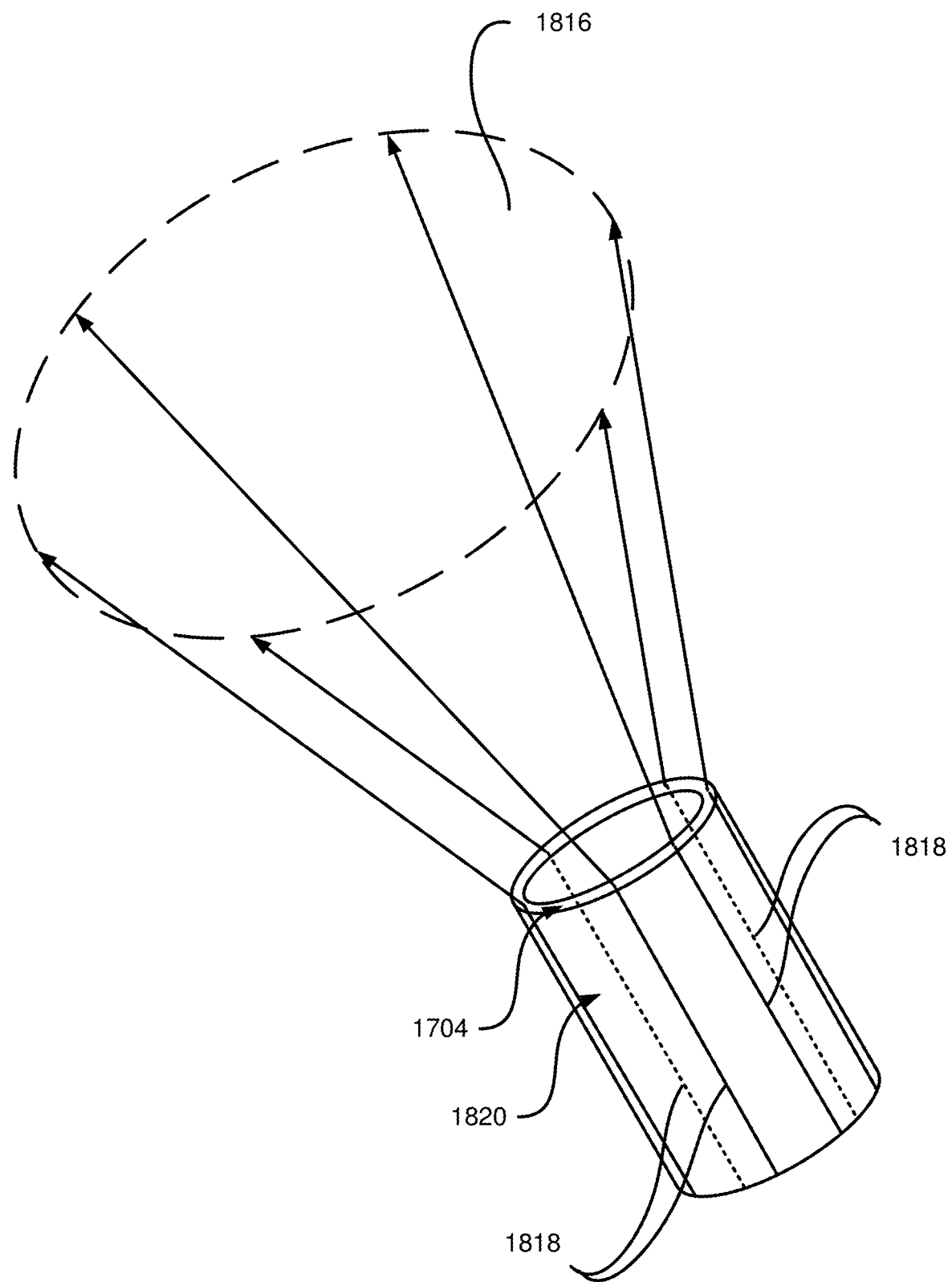
FIG. 18 is a perspective view of a portion of an endoscope lumen with a plurality of optical fibers disposed within the peripheral cavity and terminating at a distal end of the endoscope lumen.

FIG. 18 illustrates an embodiment of an endoscope lumen 1820 and the light cone 1816 of electromagnetic radiation exiting the endoscope lumen 1820. In an embodiment, the waveguide 1818 is an optical fiber bundle comprising a plurality of optical fibers. In such an embodiment, the plurality of optical fibers of the waveguide 1818 may be disposed within the peripheral cavity 1704 of the endoscope lumen 1820. In the example illustrated in FIG. 18, there are a plurality of optical fibers disposed within the peripheral cavity 1704 of the endoscope lumen 1820 such that optical fibers on the near side of the figure are illustrated with solid lines and optical fibers on the far side of the figure are illustrated with dotted lines. The solid lines extending from the endoscope lumen 1820 illustrate the beams of electromagnetic radiation emanating from the plurality of optical fibers of the waveguide 1818. These beams of electromagnetic radiation form a light cone 1816 of illumination.

Figure 19A:
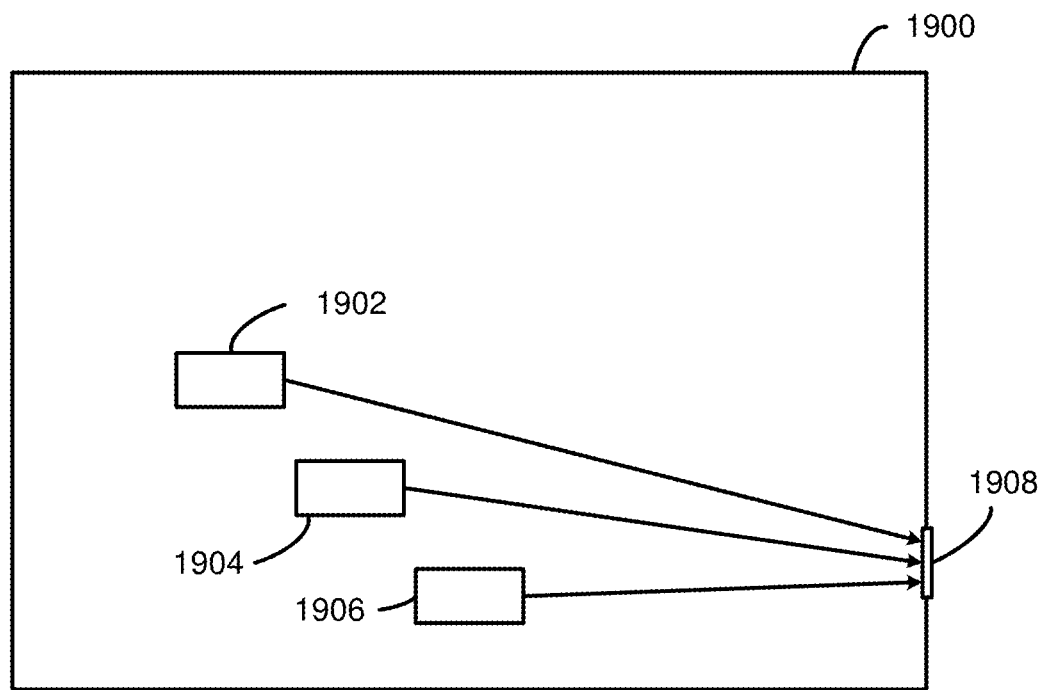
FIGS. 19A-19C illustrate an emitter module having a plurality of emitters.
Figure 19B:
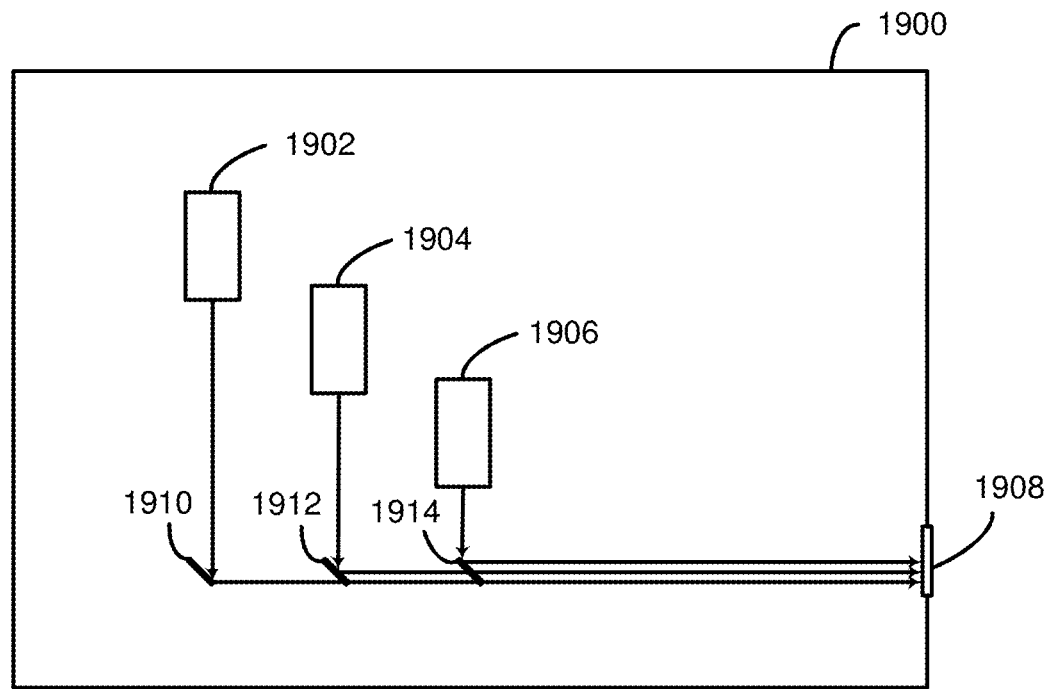
Figure 19C:
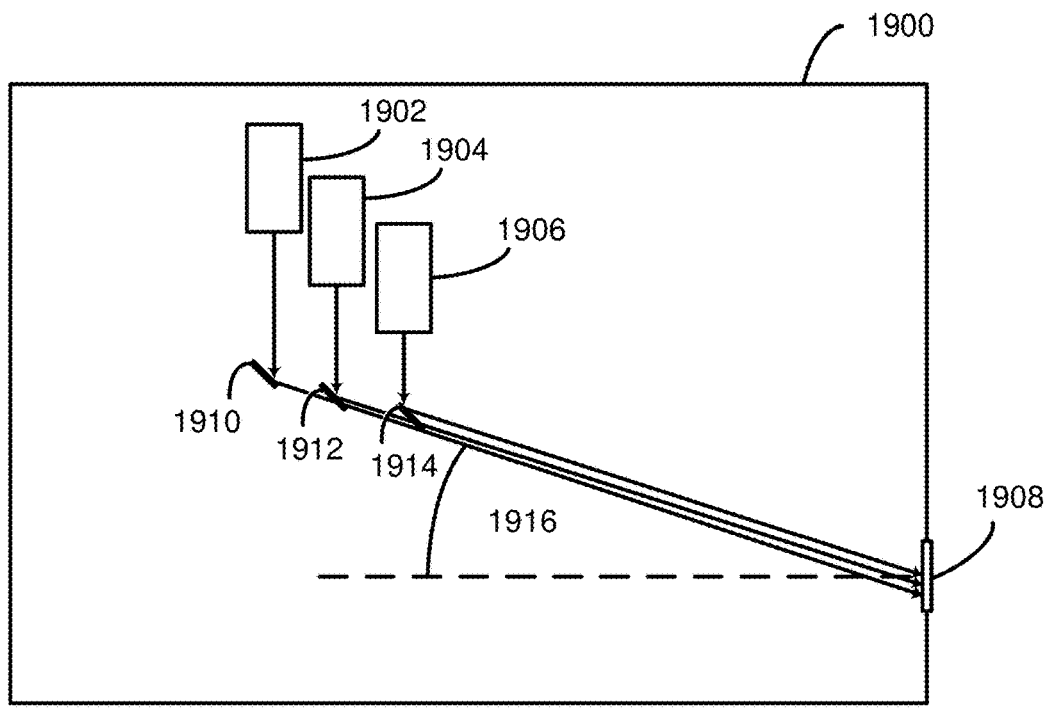

FIGS. 19A-19C each illustrate an emitter 102 having a plurality of emitters. The plurality of emitters may alternatively be referred to as "laser bundles," wherein each emitter/laser bundle can operate independently of the others and/or pulse different partitions or wavelengths of the electromagnetic spectrum. The emitter module 1900 can collectively be referred to as an "emitter" herein. Therefore, the term "emitter" as used herein and in the appended claims should not be seen as limiting, and may refer to one or more emitters or lasers for pulsing electromagnetic radiation, may refer to the collection of emitters within the emitter module 1900, and may refer to the emitter module 1900 itself.

The plurality of emitters within the emitter module 1900 include a first emitter 1902, a second emitter 1904, and a third emitter 1906. Additional emitters may be included, as discussed further below. The emitters 1902, 1904, and 1906 may include one or more laser emitters that emit light having different wavelengths. In an embodiment, one or more of the emitters 1902, 1904, 1906 includes a bundle of lasers for pulsing a partition of the electromagnetic spectrum. For example, the first emitter 1902 may emit a wavelength that is consistent with a blue laser, the second emitter 1904 may emit a wavelength that is consistent with a green laser, and the third emitter 1906 may emit a wavelength that is consistent with a red laser. For example, the first emitter 1902 may include one or more blue lasers, the second emitter 1904 may include one or more green lasers, and the third emitter 1906 may include one or more red lasers. The emitters 1902, 1904, 1906 emit laser beams toward a collection region 1908, which may be the location of a waveguide, lens, or other optical component for collecting and/or providing light to a waveguide, such as the jumper waveguide 206 or lumen waveguide 210 of FIG. 2.

In an embodiment, the emitter module 1900 includes one or more emitters 1902, 1904, 1906 for emitting hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an embodiment, the emitter module 1900 includes one or more emitters 1902, 1904, 1906 for emitting fluorescence excitation wavelengths of electromagnetic radiation. In some implementations, a fluorescent reagent or dye may be administered to a patient, and the known fluorescence excitation wavelength for fluorescing the reagent is pulsed. The fluorescence relaxation wavelength of the reagent may be sensed by the system to generate a fluorescence exposure frame. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitter module 1900 includes one or more emitters 1902, 1904, and 1906 for emitting a laser mapping pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 1902, 1904, and 1906 may emit a laser mapping pattern such that a laser mapping pattern is projected on to each tool individually. In such an embodiment, the laser mapping data for each of the tools can be analyzed to identify distances between the tools and other objects in the scene.

In the embodiment of FIG. 19B, the emitters 1902, 1904, 1906 each deliver laser light to the collection region 1908 at different angles. The variation in angle can lead to variations where electromagnetic energy is located in an output waveguide. For example, if the light passes immediately into a fiber bundle (glass or plastic) at the collection region 1908, the varying angles may cause different amounts of light to enter different fibers. For example, the angle may result in intensity variations across the collection region 1908. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 1902, 1904, 1906 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 1908 is represented as a physical component in FIG. 19A, the collection region 1908 may simply be a region where light from the emitters 1902, 1904, and 1906 is delivered. In some cases, the collection region 1908 may include an optical component such as a diffuser, mixing rod, lens, or any other intervening optical component between the emitters 1902, 1904, 1906 and an output waveguide.

FIG. 19C illustrates an embodiment of an emitter module 1900 with emitters 1902, 1904, 1906 that provide light to the collection region 1908 at the same or substantially same angle. The light is provided at an angle substantially perpendicular to the collection region 1908. The emitter module 1900 includes a plurality of dichroic mirrors including a first dichroic mirror 1910, a second dichroic mirror 1912, and a third dichroic mirror 1914. The dichroic mirrors 1910, 1912, 1914 include mirrors that reflect a first wavelength of light but transmit (or are transparent to) a second wavelength of light. For example, the third dichroic mirror 1914 may reflect blue laser light provided by the third emitter, while being transparent to the red and green light provided by the first emitter 1902 and the second emitter 1904, respectively. The second dichroic mirror 1912 may be transparent to red light from the first emitter 1902, but reflective to green light from the second emitter 1904. If other colors or wavelengths are included dichroic mirrors may be selected to reflect light corresponding to at least one emitter and be transparent to other emitters. For example, the third dichroic mirror 1914 reflect the light form the third emitter 1906 but is to emitters "behind" it, such as the first emitter 1902 and the second emitter 1904. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 1908 at a substantially same angle.

Because the dichroic mirrors allow other wavelengths to transmit or pass through, each of the wavelengths may arrive at the collection region 1908 from a same angle and/or with the same center or focal point. Providing light from the same angle and/or same focal/center point can significantly improve reception and color mixing at the collection region 1908. For example, a specific fiber may receive the different colors in the same proportions they were transmitted/reflected by the emitters 1902, 1904, 1906 and mirrors 1910, 1912, 1914. Light mixing may be significantly improved at the collection region compared to the embodiment of FIG. 19B. In one embodiment, any optical components discussed herein may be used at the collection region 1908 to collect light prior to providing it to a fiber or fiber bundle.

FIG. 19C illustrates an embodiment of an emitter module 1900 with emitters 1902, 1904, 1906 that also provide light to the collection region 1908 at the same or substantially same angle. However, the light incident on the collection region 1908 is offset from being perpendicular. Angle 1916 indicates the angle offset from perpendicular. In one embodiment, the laser emitters 1902, 1904, 1906 may have cross sectional intensity profiles that are Gaussian. As discussed previously, improved distribution of light energy between fibers may be accomplished by creating a more flat or top hat shaped intensity profile. In one embodiment, as the angle 1916 is increased, the intensity across the collection region 1908 approaches a top hat profile. For example, a top hat profile may be approximated even with a non-flat output beam by increasing the angle 1916 until the profile is sufficiently flat. The top hat profile may also be accomplished using one or more lenses, diffusers, mixing rods, or any other intervening optical component between the emitters 1902, 1904, 1906 and an output waveguide, fiber, or optical fiber bundle.

Figure 20:
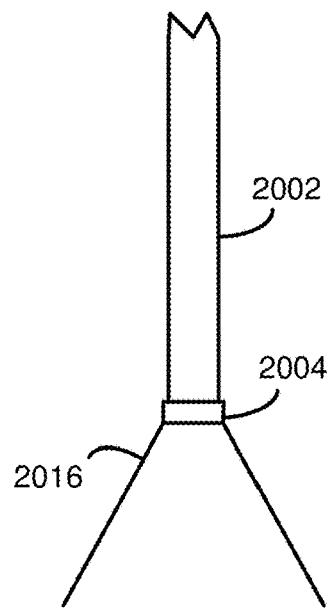
FIG. 20 illustrates a single optical fiber outputting via a diffuser at an output to illuminate a scene in a light deficient environment.

FIG. 20 is a schematic diagram illustrating a single optical fiber 2002 outputting via a diffuser 2004 at an output. In one embodiment, the optical fiber 2002 has a diameter of 500 microns, a numerical aperture of 0.65, and emits a light cone 2016 of about 70 or 80 degrees without a diffuser 2004. With the diffuser 2004, the light cone 2016 may have an angle of about 110 or 120 degrees. The light cone 2016 may be a majority of where all light goes and is evenly distributed. The diffuser 2004 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the emitter module or via a jumper waveguide. A diffuser may be used to broaden the light output 206 for a desired field of view of the image sensor 214 or other optical components.

Although three emitters are shown in FIGS. 19A-19C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 21:
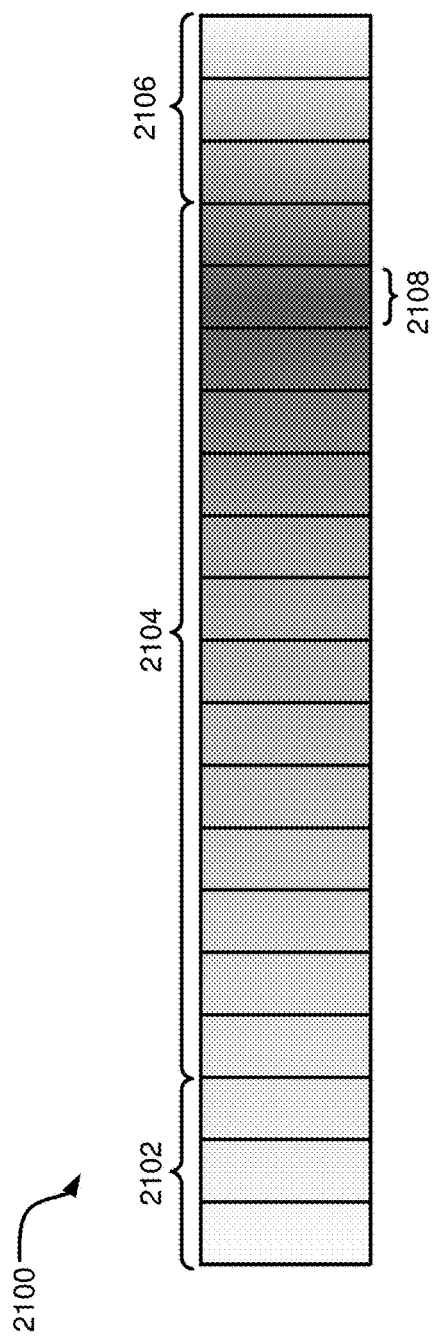
FIG. 21 illustrates a portion of the electromagnetic spectrum divided into a plurality of different sub-spectrums which may be emitted by emitters of an emitter module in accordance with the principles and teachings of the disclosure.

FIG. 21 illustrates a portion of the electromagnetic spectrum 2100 divided into twenty different sub-spectrums. The number of sub-spectrums is illustrative only. In at least one embodiment, the spectrum 2100 may be divided into hundreds of sub-spectrums, each with a small waveband. The spectrum may extend from the infrared spectrum 2102, through the visible spectrum 2104, and into the ultraviolet spectrum 2106. The sub-spectrums each have a waveband 2108 that covers a portion of the spectrum 2100. Each waveband may be defined by an upper wavelength and a lower wavelength.

Hyperspectral imaging includes imaging information from across the electromagnetic spectrum 2100. A hyperspectral pulse of electromagnetic radiation may include a plurality of sub-pulses spanning one or more portions of the electromagnetic spectrum 2100 or the entirety of the electromagnetic spectrum 2100. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 2100 and may include multiple exposure frames for multiple partitions of the electromagnetic spectrum 2100. In an embodiment, a hyperspectral exposure frame includes multiple hyperspectral exposure frames such that the combined hyperspectral exposure frame comprises data for the entirety of the electromagnetic spectrum 2100.

In one embodiment, at least one emitter (such as a laser emitter) is included in an emitter module (such as the emitter modules 212, 102) for each sub-spectrum to provide complete and contiguous coverage of the whole spectrum 2100. For example, an emitter module for providing coverage of the illustrated sub-spectrums may include at least 21 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 22:
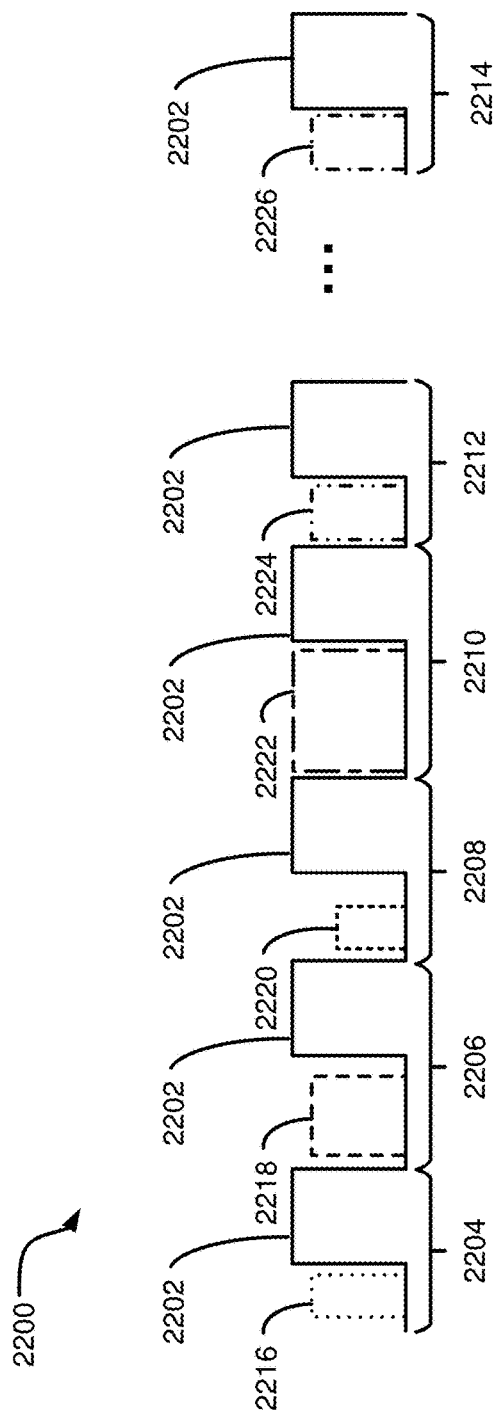
FIG. 22 is a schematic diagram illustrating a timing sequence for emission and readout for generating an image frame comprising a plurality of exposure frames resulting from differing partitions of pulsed light.

FIG. 22 is a schematic diagram illustrating a timing diagram 2200 for emission and readout for generating an image. The solid line represents readout (peaks 2202) and blanking periods (valleys) for capturing a series of exposure frames 2204-2214. The series of exposure frames 2204-2214 may include a repeating series of exposure frames which may be used for generating laser mapping, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser mapping data. The multiple exposure frames are combined to produce the single image frame. The single image frame is an RGB image with hyperspectral imaging data. The series of exposure frames include a first exposure frame 2204, a second exposure frame 2206, a third exposure frame 2208, a fourth exposure frame 2210, a fifth exposure frame 2212, and an Nth exposure frame 2226.

Additionally, the hyperspectral image data, the fluorescence image data, and the laser mapping data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser mapping data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser mapping data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (2202). Thus, each blanking period and readout results in an exposure frame for a specific spectrum of electromagnetic energy. For example, the first exposure frame 2204 may be generated based on a spectrum of a first one or more pulses 2216, a second exposure frame 2206 may be generated based on a spectrum of a second one or more pulses 2218, a third exposure frame 2208 may be generated based on a spectrum of a third one or more pulses 2220, a fourth exposure frame 2210 may be generated based on a spectrum of a fourth one or more pulses 2222, a fifth exposure frame 2212 may be generated based on a spectrum of a fifth one or more pulses, and an Nth exposure frame 2226 may be generated based on a spectrum of an Nth one or more pulses 2226.

The pulses 2216-2226 may include energy from a single emitter or from a combination of two or more emitters. For example, the spectrum included in a single readout period or within the plurality of exposure frames 2204-2214 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 2216 may include red light, pulse 2218 may include blue light, and pulse 2220 may include green light while the remaining pulses 2222-2226 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 2204-2214 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene.

The endoscopic imaging system may further emit a laser mapping pulsing scheme for generating a topology of the scene and calculating dimensions for objects within the scene. The location of the cancerous cells (as identified by the fluorescence imaging data) may be combined with the topology and dimensions information calculated based on the laser mapping data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser mapping pulsing scheme for generating a topology of the scene and calculating dimensions of objects within the scene. The location of the diseased tissue (as identified by the hyperspectral imaging data) may be combined with the topology and dimensions information that is calculated with the laser mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 23:
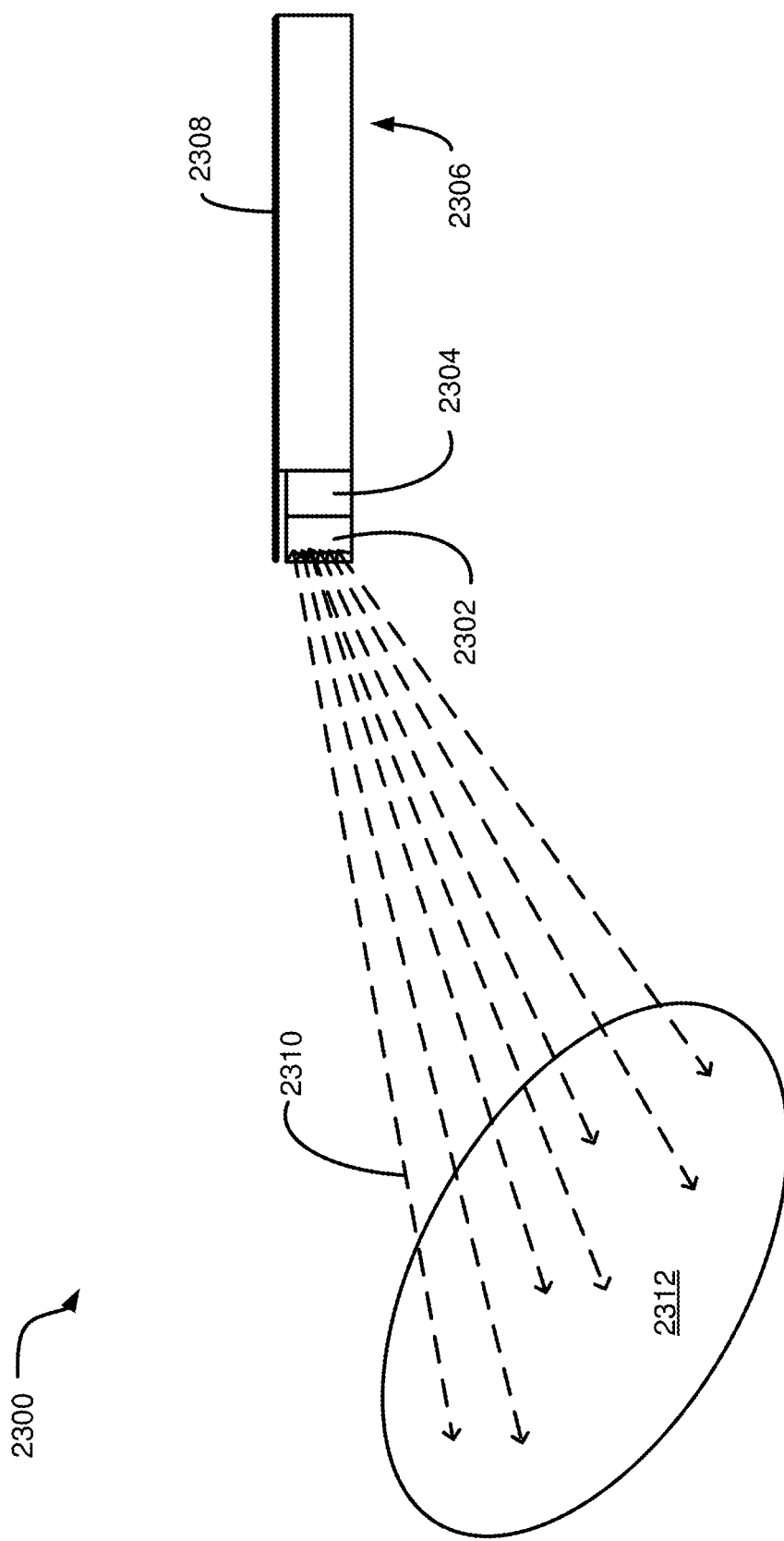
FIG. 23 illustrates an imaging system including a single cut filter for filtering wavelengths of electromagnetic radiation.

FIG. 23 is a schematic diagram of an imaging system 2300 having a single cut filter. The system 2300 includes an endoscope 2306 or other suitable imaging device having a light source 2308 for use in a light deficient environment. The endoscope 2306 includes an image sensor 2304 and a filter 2302 for filtering out unwanted wavelengths of light or other electromagnetic radiation before reaching the image sensor 2304. The light source 2308 transmits light that may illuminate the surface 2312 in a light deficient environment such as a body cavity. The light 2310 is reflected off the surface 2312 and passes through the filter 2302 before hitting the image sensor 2304.

The filter 2302 may be used in an implementation where a fluorescent reagent or dye has been administered. In such an embodiment, the light source 2308 emits the excitation wavelength for fluorescing the fluorescent reagent or dye. Commonly, the relaxation wavelength emitted by the fluorescent reagent or dye will be of a different wavelength than the excitation wavelength. The filter 2302 may be selected to filter out the excitation wavelength and permit only the relaxation wavelength to pass through the filter and be sensed by the image sensor 2304.

In one embodiment, the filter 2302 is configured to filter out an excitation wavelength of electromagnetic radiation that causes a reagent or dye to fluoresce such that only the expected relaxation wavelength of the fluoresced reagent or dye is permitted to pass through the filter 2302 and reach the image sensor 2304. In an embodiment, the filter 2302 filters out at least a fluorescent reagent excitation wavelength between 770 nm and 790 nm. In an embodiment, the filter 2302 filters out at least a fluorescent reagent excitation wavelength between 795 nm and 815 nm. In an embodiment, the filter 2302 filters out at least a fluorescent reagent excitation wavelength between 770 nm and 790 nm and between 795 nm and 815 nm. In these embodiments, the filter 2302 filters out the excitation wavelength of the reagent and permits only the relaxation wavelength of the fluoresced reagent to be read by the image sensor 2304. The image sensor 2304 may be a wavelength-agnostic image sensor and the filter 2302 may be configured to permit the image sensor 2304 to only receive the relaxation wavelength of the fluoresced reagent and not receive the emitted excitation wavelength for the reagent. The data determined by the image sensor 2304 may then indicate a presence of a critical body structure, tissue, biological process, or chemical process as determined by a location of the reagent or dye.

The filter 2302 may further be used in an implementation where a fluorescent reagent or dye has not been administered. The filter 2302 may be selected to permit wavelengths corresponding to a desired spectral response to pass through and be read by the image sensor 2304. The image sensor 2304 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 2304, may indicate the presence of a certain body tissue or structure, a certain condition, a certain chemical process, and so forth.

Figure 24:
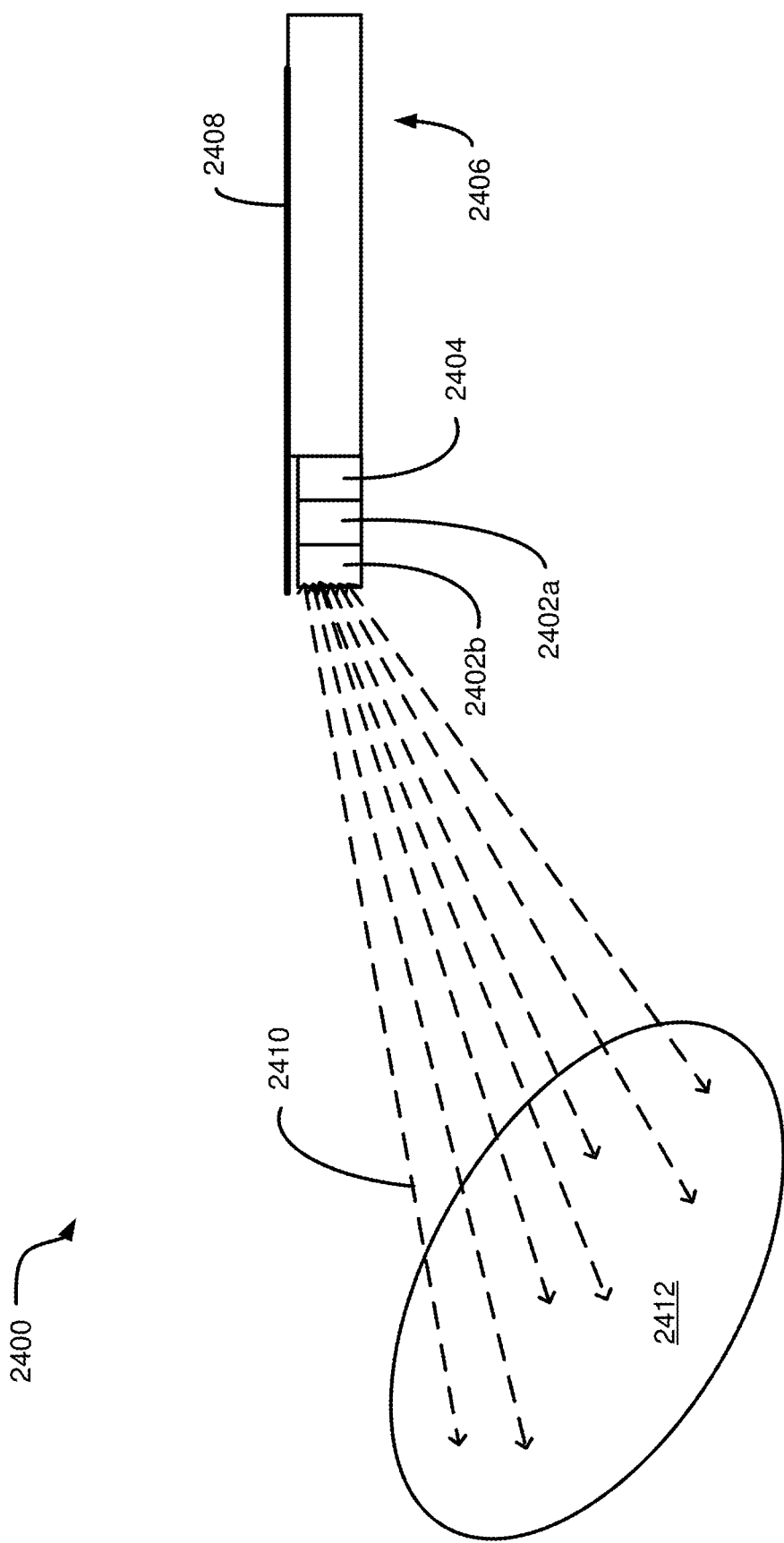
FIG. 24 illustrates an imaging system comprising a multiple cut filter for filtering wavelengths of electromagnetic radiation.

FIG. 24 is a schematic diagram of an imaging system 2400 having multiple cut filters. The system 2400 includes an endoscope 2406 or other suitable imaging device having a light source 2408 for use in a light deficient environment. The endoscope 2406 includes an image sensor 2404 and two filters 2402*a*, 2402*b*. It should be appreciated that in alternative embodiments, the system 2400 may include any number of filters, and the number of filters and the type of filters may be selected for a certain purpose e.g., for gathering imaging information of a particular body tissue, body condition, chemical process, and so forth. The filters 2402*a*, 2402*b* are configured for preventing unwanted wavelengths of light or other electromagnetic radiation from being sensed by the image sensor 2404. The filters 2402*a*, 2402*b* may be configured to filter out unwanted wavelengths from white light or other electromagnetic radiation that may be emitted by the light source 2408.

Further to the disclosure with respect to FIG. 23, the filters 2402*a*, 2402*b* may be used in an implementation where a fluorescent reagent or dye has been administered. The filters 2402*a*, 2402*b* may be configured for blocking an emitted excitation wavelength for the reagent or dye and permitting the image sensor 2404 to only read the relaxation wavelength of the reagent or dye. Further, the filters 2402*a*, 2402*b* may be used in an implementation where a fluorescent reagent or dye has not been administered. In such an implementation, the filters 2402*a*, 2402*b* may be selected to permit wavelengths corresponding to a desired spectral response to pass through and be read by the image sensor 2404.

The multiple filters 2402*a*, 2402*b* may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 2404.

In an embodiment, the filters 2402*a*, 2402*b* are customized such that electromagnetic radiation between 513 nm and 545 nm contacts the image sensor 2404. In an embodiment, the filters 2402*a*, 2402*b* are customized such that electromagnetic radiation between 565 nm and 585 nm contacts the image sensor 2404. In an embodiment, the filters 2402*a*, 2402*b* are customized such that electromagnetic radiation between 900 nm and 1000 nm contacts the image sensor 2404. In an embodiment, the filters 2402*a*, 2402*b* are customized such that electromagnetic radiation between 423 nm and 475 nm contacts the image sensor 2404. In an embodiment, the filters 2402*a*, 2402*b* are customized such that electromagnetic radiation between 520 nm and 545 nm contacts the image sensor 2404. In an embodiment, the filters 2402*a*, 2402*b* are customized such that electromagnetic radiation between 617 nm and 645 nm contacts the image sensor 2404. In an embodiment, the filters 2402*a*, 2402*b* are customized such that electromagnetic radiation between 760 nm and 795 nm contacts the image sensor 2404. In an embodiment, the filters 2402*a*, 2402*b* are customized such that electromagnetic radiation between 795 nm and 815 nm contacts the image sensor 2404. In an embodiment, the filters 2402*a*, 2402*b* are customized such that electromagnetic radiation between 370 nm and 420 nm contacts the image sensor 2404. In an embodiment, the filters 2402*a*, 2402*b* are customized such that electromagnetic radiation between 600 nm and 670 nm contacts the image sensor 2404. In an embodiment, the filters 2402*a*, 2402*b* are configured for permitting only a certain fluorescence relaxation emission to pass through the filters 2402*a*, 2402*b* and contact the image sensor 2404. In an embodiment, a first filter blocks electromagnetic radiation having a wavelength from about 770 nm to about 790 nm, and a second filter blocks electromagnetic radiation having a wavelength from about 795 nm to about 815 nm.

In an embodiment, the system 2400 includes multiple image sensors 2404 and may particularly include two image sensors for use in generating a three-dimensional image. The image sensor(s) 2404 may be color/wavelength agnostic and configured for reading any wavelength of electromagnetic radiation that is reflected off the surface 2412. In an embodiment, the image sensors 2404 are each color dependent or wavelength dependent and configured for reading electromagnetic radiation of a particular wavelength that is reflected off the surface 2412 and back to the image sensors 2404. Alternatively, the image sensor 2404 may include a single image sensor with a plurality of different pixel sensors configured for reading different wavelengths or colors of light, such as a Bayer filter color filter array. Alternatively, the image sensor 2404 may include one or more color agnostic image sensors that may be configured for reading different wavelengths of electromagnetic radiation according to a pulsing schedule such as those illustrated in FIGS. 5-7E, for example.

Figure 25:
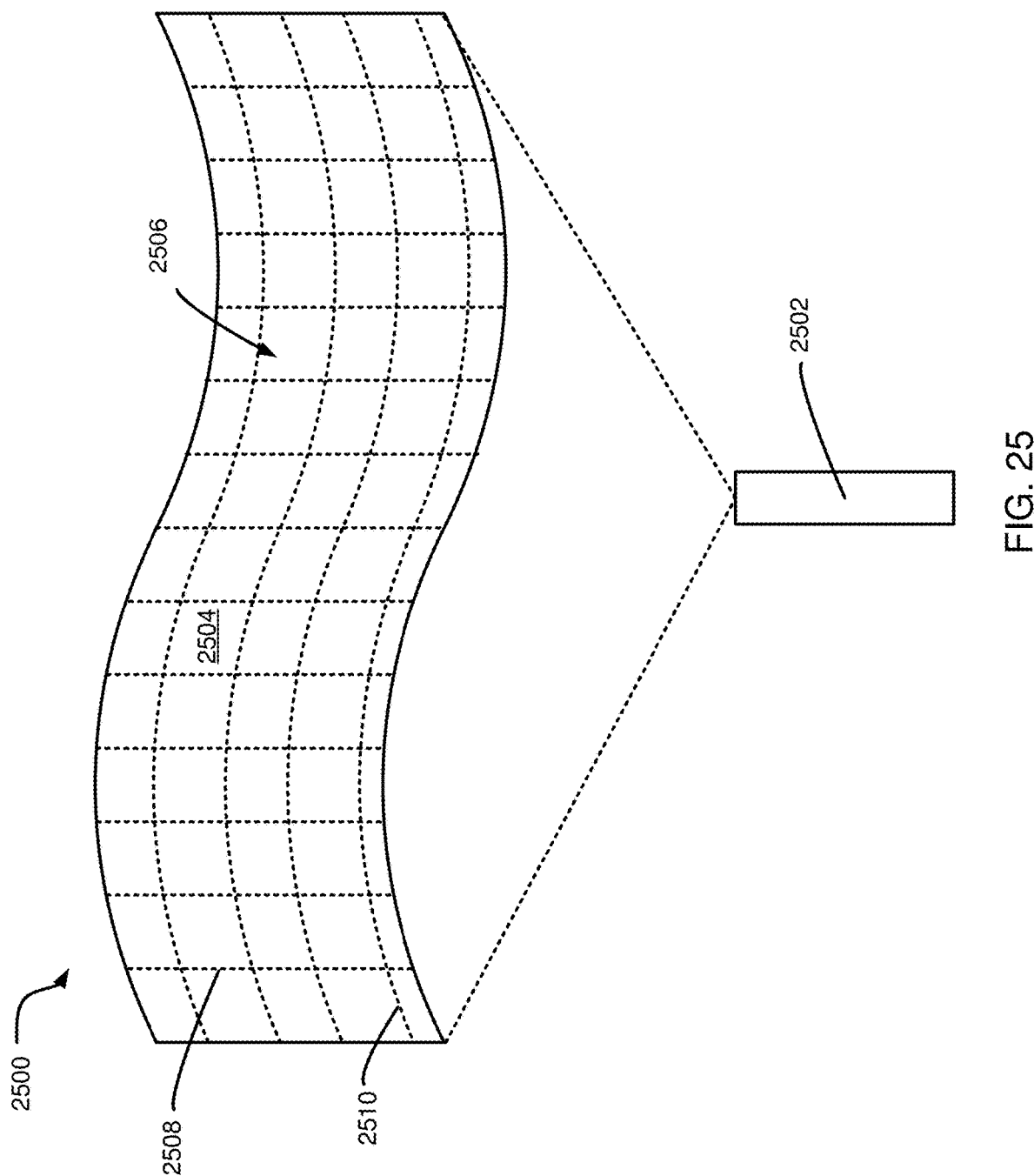
FIG. 25 illustrates an example laser mapping pattern that may be pulsed by an imaging system.

FIG. 25 is a schematic diagram illustrating a system 2500 for mapping a surface and/or tracking an object in a light deficient environment through laser mapping imaging. In an embodiment, an endoscope 2506 in a light deficient environment pulses a grid array 2506 (may be referred to as a laser map pattern) on a surface 2504. The grid array 2506 includes vertical hashing 2508 and horizontal hashing 2510 in one embodiment as illustrated in FIG. 25. It should be appreciated the grid array 2506 may include any suitable array for mapping a surface 2504, including, for example, a raster grid of discrete points, an occupancy grid map, a dot array, and so forth. Additionally, the endoscope 2506 may pulse multiple grid arrays 2506 and may, for example, pulse one or more individual grid arrays on each of a plurality of objects or structures within the light deficient environment.

In an embodiment, the system 2500 pulses a grid array 2506 that may be used for mapping a three-dimensional topology of a surface and/or tracking a location of an object such as a tool or another device in a light deficient environment. In an embodiment, the system 2500 provides data to a third-party system or computer algorithm for determining surface dimensions and configurations by way of light detection and ranging (LIDAR) mapping. The system 2500 may pulse any suitable wavelength of light or electromagnetic radiation in the grid array 2506, including, for example, ultraviolet light, visible, light, and/or infrared or near infrared light. The surface 2504 and/or objects within the environment may be mapped and tracked at very high resolution and with very high accuracy and precision.

In an embodiment, the system 2500 includes an imaging device having a tube, one or more image sensors, and a lens assembly having an optical element corresponding to the one or more image sensors. The system 2500 may include a light engine having an emitter generating one or more pulses of electromagnetic radiation and a lumen transmitting the one or more pulses of electromagnetic radiation to a distal tip of an endoscope within a light deficient environment such as a body cavity. In an embodiment, at least a portion of the one or more pulses of electromagnetic radiation includes a laser map pattern that is emitted onto a surface within the light deficient environment, such as a surface of body tissue and/or a surface of tools or other devices within the body cavity. The endoscope 2506 may include a two-dimensional, three-dimensional, or n-dimensional camera for mapping and/or tracking the surface, dimensions, and configurations within the light deficient environment.

In an embodiment, the system 2500 includes a processor for determining a distance of an endoscope or tool from an object such as the surface 2504. The processor may further determine an angle between the endoscope or tool and the object. The processor may further determine surface area information about the object, including for example, the size of surgical tools, the size of structures, the size of anatomical structures, location information, and other positional data and metrics. The system 2500 may include one or more image sensors that provide image data that is output to a control system for determining a distance of an endoscope or tool to an object such as the surface 2504. The image sensors may output information to a control system for determining an angle between the endoscope or tool to the object. Additionally, the image sensors may output information to a control system for determining surface area information about the object, the size of surgical tools, size of structures, size of anatomical structures, location information, and other positional data and metrics.

In an embodiment, the grid array 2506 is pulsed by an emitter of the endoscope 2506 at a sufficient speed such that the grid array 2506 is not visible to a user. In various implementations, it may be distracting to a user to see the grid array 2506 during an endoscopic imaging procedure and/or endoscopic surgical procedure. The grid array 2506 may be pulsed for sufficiently brief periods such that the grid array 2506 cannot be detected by a human eye. In an alternative embodiment, the endoscope 2506 pulses the grid array 2506 at a sufficient recurring frequency such that the grid array 2506 may be viewed by a user. In such an embodiment, the grid array 2506 may be overlaid on an image of the surface 2504 on a display. The grid array 2506 may be overlaid on a black-and-white or RGB image of the surface 2504 such that the grid array 2506 may be visible by a user during use of the system 2500. A user of the system 2500 may indicate whether the grid array 2506 should be overlaid on an image of the surface 2504 and/or whether the grid array 2506 should be visible to the user. The system 2500 may include a display that provides real-time measurements of a distance from the endoscope 2506 to the surface 2504 or another object within the light deficient environment. The display may further provide real-time surface area information about the surface 2504 and/or any objects, structures, or tools within the light deficient environment. The accuracy of the measurements may be accurate to less than one millimeter.

In an embodiment, the system 2500 pulses a plurality of grid arrays 2506. In an embodiment, each of the plurality of grid arrays 2506 corresponds to a tool or other device present within the light deficient environment. The precise locations and parameters of each of the tools and other devices may be tracked by pulsing and sensing the plurality of grid arrays 2506. The information generated by sensing the reflected grid arrays 2506 can be assessed to identify relative locations of the tools and other devices within the light deficient environment.

The endoscope 2506 may pulse electromagnetic radiation according to a pulsing schedule such as those illustrated herein that may further include pulsing of the grid array 2506 along with pulsing Red, Green, and Blue light for generating an RGB image and further generating a grid array 2506 that may be overlaid on the RGB image and/or used for mapping and tracking the surface 2504 and objects within the light deficient environment. The grid array 2506 may additionally be pulsed in conjunction with hyperspectral or fluorescent excitation wavelengths of electromagnetic radiation. The data from each of the RGB imaging, the laser mapping imaging, the hyperspectral imaging, and the fluorescence imaging may be combined to identify the locations, dimensions, and surface topology of critical structures in a body.

In an embodiment, the endoscope 2506 includes one or more color agnostic image sensors. In an embodiment, the endoscope 2506 includes two color agnostic image sensors for generating a three-dimensional image or map of the light deficient environment. The image sensors may generate an RGB image of the light deficient environment according to a pulsing schedule as disclosed herein. Additionally, the image sensors may determine data for mapping the light deficient environment and tracking one or more objects within the light deficient environment based on data determined when the grid array 2506 is pulsed. Additionally, the image sensors may determine spectral or hyperspectral data along with fluorescence imaging data according to a pulsing schedule that may be modified by a user to suit the particular needs of an imaging procedure. In an embodiment, a pulsing schedule includes Red, Green, and Blue pulses along with pulsing of a grid array 2506 and/or pulsing for generating hyperspectral image data and/or fluorescence image data. In various implementations, the pulsing schedule may include any suitable combination of pulses of electromagnetic radiation according to the needs of a user. The recurring frequency of the different wavelengths of electromagnetic radiation may be determined based on, for example, the energy of a certain pulse, the needs of the user, whether certain data (for example, hyperspectral data and/or fluorescence imaging data) needs to be continuously updated or may be updated less frequently, and so forth.

The pulsing schedule may be modified in any suitable manner, and certain pulses of electromagnetic radiation may be repeated at any suitable frequency, according to the needs of a user or computer-implemented program for a certain imaging procedure. For example, in an embodiment where surface tracking data generated based on the grid array 2506 is provided to a computer-implemented program for use in, for example, a robotic surgical procedure, the grid array 2506 may be pulsed more frequently than if the surface tracking data is provided to a user who is visualizing the scene during the imaging procedure. In such an embodiment where the surface tracking data is used for a robotic surgical procedure, the surface tracking data may need to be updated more frequently or may need to be exceedingly accurate such that the computer-implemented program may execute the robotic surgical procedure with precision and accuracy.

In an embodiment, the system 2500 is configured to generate an occupancy grid map comprising an array of cells divided into grids. The system 2500 is configured to store height values for each of the respective grid cells to determine a surface mapping of a three-dimensional environment in a light deficient environment.

Figure 26A:
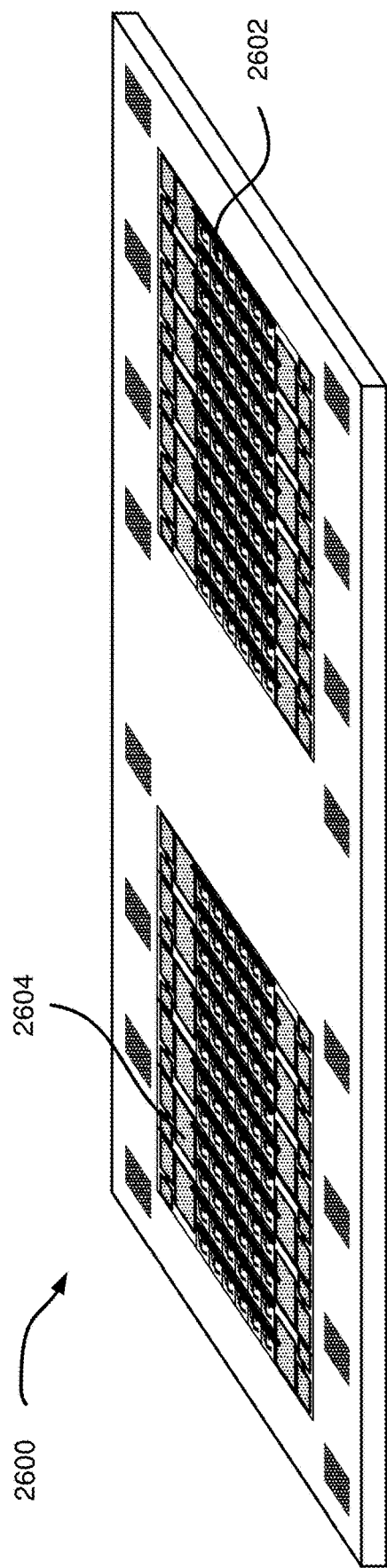
FIGS. 26A and 26B illustrate an implementation having a plurality of pixel arrays for producing a three-dimensional image in accordance with the principles and teachings of the disclosure.
Figure 26B:
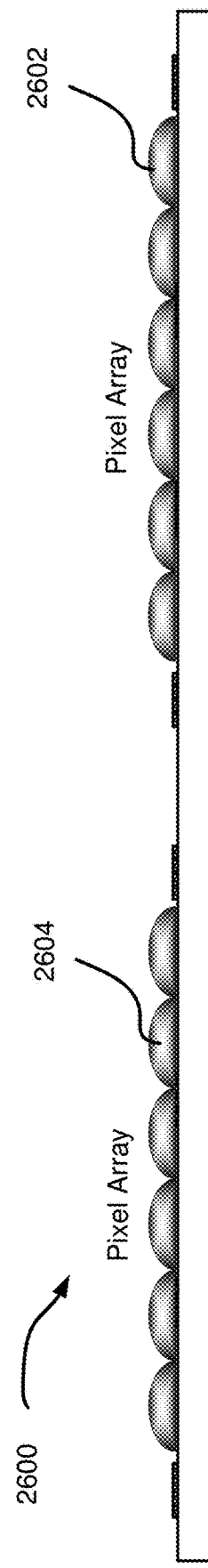

FIGS. 26A and 26B illustrate a perspective view and a side view, respectively, of an implementation of a monolithic sensor 2600 having a plurality of pixel arrays for producing a three-dimensional image in accordance with the teachings and principles of the disclosure. Such an implementation may be desirable for three-dimensional image capture, wherein the two-pixel arrays 2602 and 2604 may be offset during use. In another implementation, a first pixel array 2602 and a second pixel array 2604 may be dedicated to receiving a predetermined range of wave lengths of electromagnetic radiation, wherein the first pixel array is dedicated to a different range of wavelength electromagnetic radiation than the second pixel array.

Figure 27A:
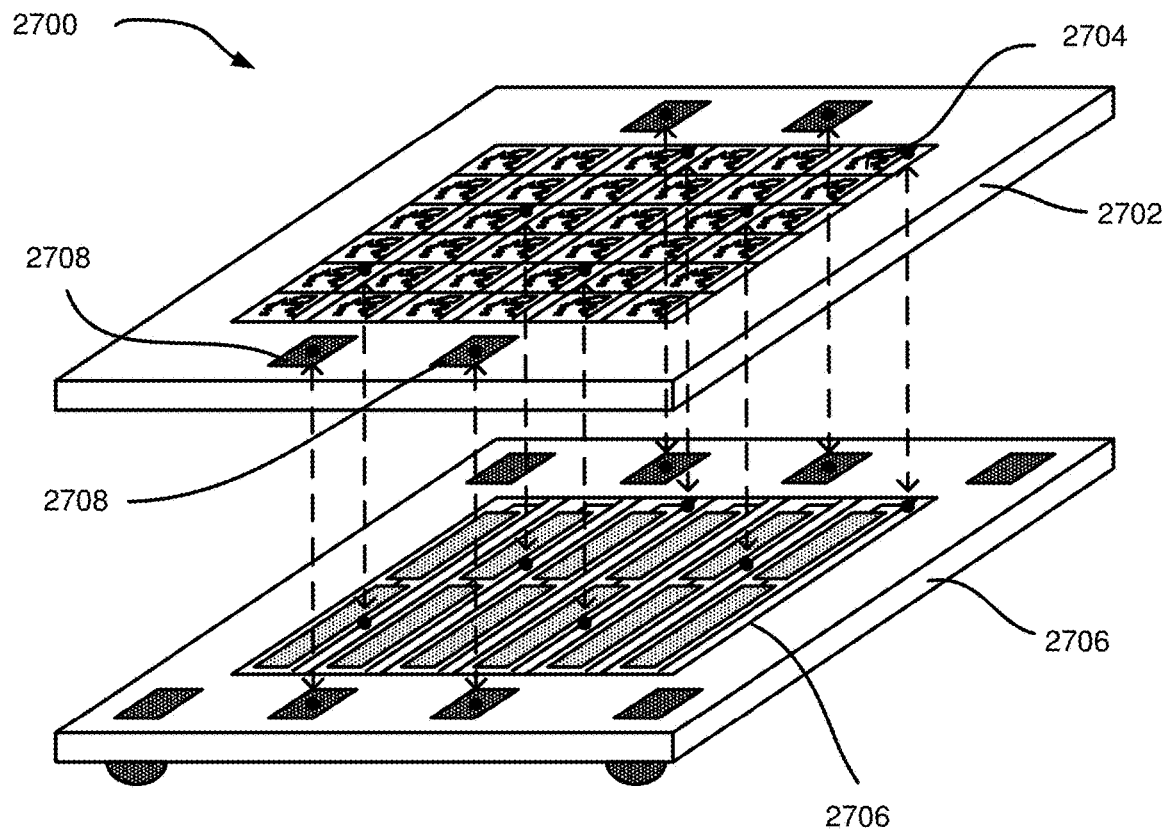
FIGS. 27A and 27B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 27B:
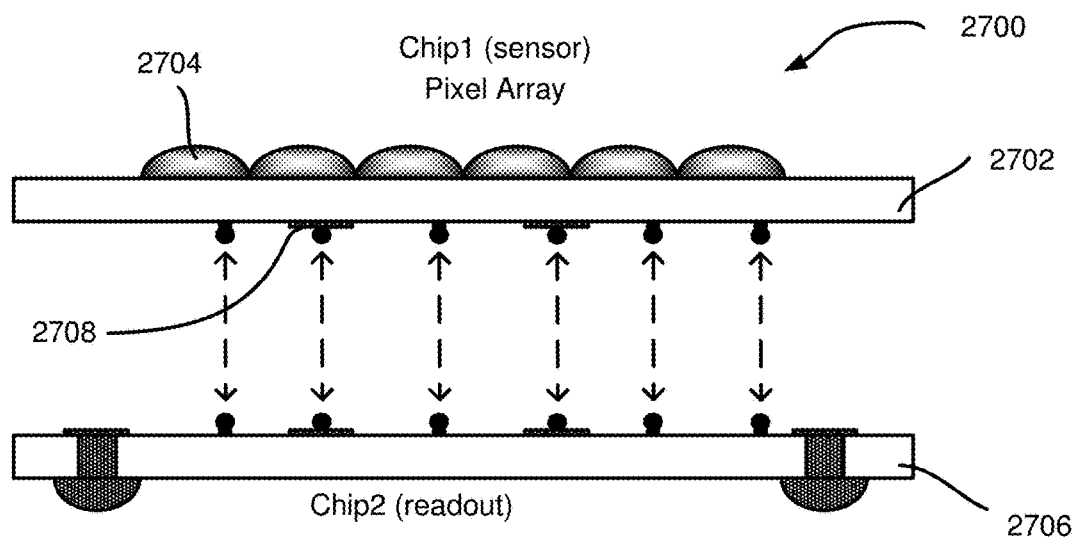

FIGS. 27A and 27B illustrate a perspective view and a side view, respectively, of an implementation of an imaging sensor 2700 built on a plurality of substrates. As illustrated, a plurality of pixel columns 2704 forming the pixel array are located on the first substrate 2702 and a plurality of circuit columns 2708 are located on a second substrate 2706. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 2702 of the two substrates/chips may be processed using an image CMOS process. The first substrate/chip 2702 may be comprised either of a pixel array exclusively or a pixel array surrounded by limited circuitry. The second or subsequent substrate/chip 2706 may be processed using any process and does not have to be from an image CMOS process. The second substrate/chip 2706 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 2702 may be stacked with the second or subsequent substrate/chip 2706 using any three-dimensional technique. The second substrate/chip 2706 may support most, or a majority, of the circuitry that would have otherwise been implemented in the first image CMOS chip 2702 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

FIGS. 28A and 28B illustrate a perspective view and a side view, respectively, of an implementation of an imaging sensor 2800 having a plurality of pixel arrays for producing a three-dimensional image. The three-dimensional image sensor may be built on a plurality of substrates and may comprise the plurality of pixel arrays and other associated circuitry, wherein a plurality of pixel columns 2802a forming the first pixel array and a plurality of pixel columns 2802b forming a second pixel array are located on respective substrates 2808a and 2808b, respectively, and a plurality of circuit columns 2806a and 2806b are located on a separate substrate 2804. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

EXAMPLES

The following examples pertain to preferred features of further embodiments:

Example 1 is a system. The system includes an emitter for emitting pulses of electromagnetic radiation. The system includes an endoscope. The endoscope comprises an image sensor, and the image sensor comprises a pixel array for sensing reflected electromagnetic radiation. The system includes a waveguide communicating the pulses of electromagnetic radiation from the emitter to the endoscope. The system includes a controller in electronic communication with the emitter and the image sensor. The system is such that at least a portion of the pulses of electromagnetic radiation emitted by the emitter comprises one or more of: electromagnetic radiation having a wavelength from about 513 nm to about 545 nm; electromagnetic radiation having a wavelength from about 565 nm to about 585 nm; electromagnetic radiation having a wavelength from about 900 nm to about 1000 nm; an excitation wavelength of electromagnetic radiation that causes a reagent to fluoresce; or a laser mapping pattern.

Example 2 is a system as in Example 1, wherein: the emitter comprises a plurality of emitters disposed within an emitter module; the image sensor is located a distal end of a lumen of the endoscope; and the waveguide communicates the pulses of electromagnetic radiation from the emitter module to the distal end of the lumen of the endoscope.

Example 3 is a system as in any of Examples 1-2, wherein the waveguide comprises one of: a single optical fiber; or an optical fiber bundle comprising a plurality of optical fibers.

Example 4 is a system as in any of Examples 1-3, further comprising a lumen of the endoscope comprising a distal end, and wherein the distal end of the lumen is configured for insertion into a light deficient environment for optical imaging, and wherein: the waveguide is an optical fiber bundle comprising a plurality of optical fibers; the plurality of optical fibers are disposed within the lumen and terminate at the distal end of the lumen; and the plurality of optical fibers are aimed in at least two different directions at the distal end of the lumen such that a light cone generated by the pulses of electromagnetic radiation exiting the plurality of optical fibers has an increased area.

Example 5 is a system as in any of Examples 1-4, wherein the waveguide comprises: a first portion comprising a plurality of plastic optical fibers; a second portion comprising a plurality of glass optical fibers; and a connector for connecting the first portion and the second portion such that electromagnetic radiation is communicated from the first portion to the second portion.

Example 6 is a system as in any of Examples 1-5, wherein the waveguide comprises an optical diffuser for increasing the area of a light cone generated by the pulses of electromagnetic radiation exiting the waveguide.

Example 7 is a system as in any of Examples 1-6, wherein: the emitter comprises a plurality of emitters in an emitter module; the waveguide comprises a single optical fiber extending from the emitter module to a distal end of a lumen of the endoscope; the single optical fiber receives the pulses of electromagnetic radiation at the emitter module; and the single optical fiber terminates at the distal end of the lumen such that the pulses of electromagnetic radiation illuminate a scene located at the distal end of the lumen.

Example 8 is a system as in any of Examples 1-7, further comprising a lumen of the endoscope, wherein the lumen comprises: an inner cavity defined by an inner cylinder for receiving optical components of the endoscope; and a peripheral cavity defined by the inner cylinder and an outer cylinder for receiving the waveguide.

Example 9 is a system as in any of Examples 1-8, wherein: the waveguide comprises an optical fiber bundle comprising a plurality of plastic optical fibers, wherein the emitter emits the pulses of electromagnetic radiation into the optical fiber bundle; the waveguide further comprises an intervening optical component, wherein the pulses of electromagnetic radiation pass through the intervening optical component before entering the optical fiber bundle; and the intervening optical component comprises a plurality of glass optical fibers.

Example 10 is a system as in any of Examples 1-9, wherein the waveguide comprises: an optical fiber bundle, wherein the emitter emits the pulses of electromagnetic radiation into the optical fiber bundle; and a diffuser disposed at a distal end of the optical fiber bundle; wherein the diffuser provides a light cone having a field of view angle between 110 degrees and 120 degrees.

Example 11 is a system as in any of Examples 1-10, wherein the waveguide comprises: a single optical fiber, wherein the emitter emits the pulses of electromagnetic radiation into the single optical fiber; and a diffuser disposed at a distal end of the single optical fiber; wherein the diffuser provides a light cone having a field of view angle between 110 degrees and 120 degrees.

Example 12 is a system as in any of Examples 1-11, wherein the pixel array of the image sensor senses reflected electromagnetic radiation to generate the plurality of exposure frames during readout periods of the pixel array, wherein the readout period comprises a duration of time when active pixels in the pixel array are read, and wherein a single exposure frame corresponds with a single readout period of the pixel array.

Example 13 is a system as in any of Examples 1-12, wherein at least a portion of the pulses of electromagnetic radiation emitted by the emitter is a hyperspectral wavelength for eliciting a spectral response, wherein the hyperspectral wavelength comprises one or more of: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 14 is a system as in any of Examples 1-13, wherein the emitter is configured to emit, during a pulse duration, a plurality of sub-pulses of electromagnetic radiation having a sub-duration shorter than the pulse duration.

Example 15 is a system as in any of Examples 1-14, wherein one or more of the pulses of electromagnetic radiation emitted by the emitter comprises electromagnetic radiation emitted at two or more wavelengths simultaneously as a single pulse or a single sub-pulse.

Example 16 is a system as in any of Examples 1-15, wherein at least a portion of the pulses of electromagnetic radiation emitted by the emitter is a hyperspectral emission that results in a hyperspectral exposure frame created by the image sensor, and wherein the controller is configured to provide the hyperspectral exposure frame to a corresponding hyperspectral system that determines a location of a critical tissue structure within a scene based on the hyperspectral exposure frame.

Example 17 is a system as in any of Examples 1-16, wherein the hyperspectral emission comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 18 is a system as in any of Examples 1-17, wherein the controller is further configured to: receive the location of the critical tissue structure from the corresponding hyperspectral system; generate an overlay frame comprising the location of the critical tissue structure; and combine the overlay frame with a color image frame depicting the scene to indicate the location of the critical tissue structure within the scene.

Example 19 is a system as in any of Examples 1-18, wherein sensing the reflected electromagnetic radiation by the pixel array comprises generating a laser mapping exposure frame by sensing reflected electromagnetic radiation resulting from the emitter pulsing the laser mapping pattern, and wherein the controller is further configured to: provide the laser mapping exposure frame to a corresponding laser mapping system that determines a topology of the scene and/or dimensions of one or more objects within the scene; provide the location of the critical tissue structure to the corresponding laser mapping system; and receive a topology and/or dimension of the critical tissue structure from the corresponding laser mapping system.

Example 20 is a system as in any of Examples 1-19, wherein the critical structure comprises one or more of a nerve, a ureter, a blood vessel, an artery, a blood flow, or a tumor.

Example 21 is a system as in any of Examples 1-20, wherein at least a portion of the pulses of electromagnetic radiation emitted by the emitter is a fluorescence excitation wavelength that results in a fluorescence exposure frame created by the image sensor, and wherein the controller is configured to provide the fluorescence exposure frame to a corresponding fluorescence system that determines a location of a critical tissue structure within a scene based on the fluorescence exposure frame.

Example 22 is a system as in any of Examples 1-21, wherein the fluorescence excitation emission comprises one or more of: electromagnetic radiation having a wavelength from about 770 nm to about 790 nm; or the electromagnetic radiation having the wavelength from about 795 nm to about 815 nm.

Example 23 is a system as in any of Examples 1-22, wherein the controller is further configured to: receive the location of the critical tissue structure from the corresponding fluorescence system; generate an overlay frame comprising the location of the critical tissue structure; and combine the overlay frame with a color image frame depicting the scene to indicate the location of the critical tissue structure within the scene.

Example 24 is a system as in any of Examples 1-23, wherein sensing the reflected electromagnetic radiation by the pixel array comprises generating a laser mapping exposure frame by sensing reflected electromagnetic radiation resulting from the emitter pulsing the laser mapping pattern, and wherein the controller is further configured to: provide the laser mapping exposure frame to a corresponding laser mapping system that determines a topology of the scene and/or dimensions of one or more objects within the scene; provide the location of the critical tissue structure to the corresponding laser mapping system; and receive a topology and/or dimension of the critical tissue structure from the corresponding laser mapping system.

Example 25 is a system as in any of Examples 1-24, wherein the critical structure comprises one or more of a nerve, a ureter, a blood vessel, an artery, a blood flow, or a tumor.

Example 26 is a system as in any of Examples 1-25, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

Example 27 is a system as in any of Examples 1-26, wherein two or more pulses of electromagnetic radiation emitted by the emitter result in two or more instances of reflected electromagnetic radiation that are sensed by the pixel array to generate two or more exposure frames that are combined to form an image frame.

Example 28 is a system as in any of Examples 1-27, wherein the image sensor comprises a first image sensor and a second image sensor such that the image sensor can generate a three-dimensional image.

Example 29 is a system as in any of Examples 1-28, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 30 is a system as in any of Examples 1-29, wherein the pulses of electromagnetic radiation are emitted in a pattern of varying wavelengths of electromagnetic radiation, and wherein the emitter repeats the pattern of varying wavelengths of electromagnetic radiation.

Example 31 is a system as in any of Examples 1-30, wherein at least a portion of the pulses of electromagnetic radiation comprise a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image frame comprising an overlay of hyperspectral imaging data, wherein the hyperspectral wavelength of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 32 is a system as in any of Examples 1-31, wherein at least a portion of the pulses of electromagnetic radiation comprise a luminance emission, a red chrominance emission, a blue chrominance emission, and a hyperspectral emission such that reflected electromagnetic radiation sensed by the pixel array corresponding to each of the luminance emission, the red chrominance emission, the blue chrominance emission, and the hyperspectral emission can be processed to generate a YCbCr image frame comprising an overlay of hyperspectral imaging data, wherein the hyperspectral emission of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 33 is a system as in any of Examples 1-32, wherein at least a portion of the pulses of electromagnetic radiation emitted by the emitter is a fluorescence excitation wavelength for fluorescing a reagent, wherein the fluorescence excitation wavelength comprises one or more of: the electromagnetic radiation having the wavelength from about 770 nm to about 790 nm; or the electromagnetic radiation having the wavelength from about 795 nm to about 815 nm.

Example 34 is a system as in any of Examples 1-33, wherein at least a portion of the pulses of electromagnetic radiation comprise a red wavelength, a green wavelength, a blue wavelength, and a fluorescence excitation wavelength such that reflected electromagnetic radiation sensed by the pixel array corresponding to each of the red wavelength, the green wavelength, the blue wavelength, and the fluorescence excitation wavelength can be processed to generate a Red-Green-Blue (RGB) image frame comprising an overlay of fluorescence imaging data, wherein the fluorescence wavelength of electromagnetic radiation comprises: electromagnetic radiation having the wavelength from about 770 nm to about 790 nm and/or electromagnetic radiation having the wavelength from about 795 nm to about 815 nm.

Example 35 is a system as in any of Examples 1-34, wherein at least a portion of the pulses of electromagnetic radiation comprise a luminance emission, a red chrominance emission, a blue chrominance emission, and a fluorescence excitation emission such that reflected electromagnetic radiation sensed by the pixel array corresponding to each of the luminance emission, the red chrominance emission, the blue chrominance emission, and the fluorescence excitation emission can be processed to generate a YCbCr image frame comprising an overlay of fluorescence imaging data, wherein the fluorescence wavelength of electromagnetic radiation comprises: electromagnetic radiation having the wavelength from about 770 nm to about 790 nm and/or electromagnetic radiation having the wavelength from about 795 nm to about 815 nm.

Example 36 is a system as in any of Examples 1-35, wherein the waveguide comprises a single optical fiber, wherein the emitter emits the pulses of electromagnetic radiation into the single optical fiber.

Example 37 is a system as in any of Examples 1-36, wherein the pixel array is a two-dimensional array of independent pixels each capable of detecting any wavelength of electromagnetic radiation.

Example 38 is a system as in any of Examples 1-37, further comprising a filter that filters electromagnetic radiation having a wavelength from about 770 nm to about 790 nm.

Example 39 is a system as in any of Examples 1-38, further comprising a filter that filters electromagnetic radiation having a wavelength from about 795 nm to about 815 nm.

Example 40 is a system as in any of Examples 1-39, wherein the image sensor is CMOS image sensor.

Example 41 is a system as in any of Examples 1-40, wherein sensing reflected electromagnetic radiation by the pixel array comprises generating a laser mapping exposure frame by sensing reflected electromagnetic radiation resulting from the emitter pulsing the laser mapping pattern, wherein the laser mapping exposure frame comprises information for determining real time measurements comprising one or more of: a distance from an endoscope to an object; an angle between an endoscope and the object; or surface topology information about the object.

Example 42 is a system as in any of Examples 1-41, wherein the laser mapping exposure frame comprises information for determining the real time measurements to an accuracy of less than 10 centimeters.

Example 43 is a system as in any of Examples 1-42, wherein the laser mapping exposure frame comprises information for determining the real time measurements to an accuracy of less than one millimeter.

Example 44 is a system as in any of Examples 1-43, wherein at least a portion of the pulses of electromagnetic radiation emitted by the emitter comprises a plurality of tool-specific laser mapping patterns for each of a plurality of tools within a scene.

Example 45 is a system as in any of Examples 1-44, wherein the laser mapping pattern emitted by the emitter comprises a first output and a second output that are independent from one another, wherein the first output is for light illumination and the second output is for tool tracking.

Example 46 is a system as in any of Examples 1-45, wherein the emitter is an emitter module comprising a first emitter and a second emitter, and wherein the first emitter comprises a plurality of lasers for emitting pulses of a first wavelength of electromagnetic radiation and the second emitter comprises a plurality of lasers for emitting pulses of a second wavelength of electromagnetic radiation.

Example 47 is a system as in any of Examples 1-46, wherein the image sensor is configured to generate a plurality of exposure frames, wherein each of the plurality of exposure frames corresponds to one or more pulses of electromagnetic radiation emitted by the emitter.

Example 48 is a system as in any of Examples 1-47, wherein the waveguide comprises an optical fiber bundle comprising between 2 and 150 fibers.

Example 49 is a system as in any of Examples 1-48, wherein the emitter comprises a third emitter comprising a plurality of lasers for emitting pulses of a third wavelength of electromagnetic radiation.

Example 50 is a system as in any of Examples 1-49, wherein the emitter comprises a fourth emitter comprising a plurality of lasers for emitting pulses of a fourth wavelength of electromagnetic radiation.

Example 51 is a system as in any of Examples 1-50, wherein the emitter comprises one or more hyperspectral emitters for emitting pulses of hyperspectral wavelengths of electromagnetic radiation for eliciting a spectral response.

Example 52 is a system as in any of Examples 1-51, wherein each of the one or more hyperspectral emitters comprises an emitter comprising a plurality of lasers.

Example 53 is a system as in any of Examples 1-52, wherein the emitter further comprises an optical element for mixing pulses of electromagnetic radiation before entry into the waveguide, wherein the optical element comprises one or more of a diffuser, a mixing rod, or a lens.

Example 54 is a system as in any of Examples 1-53, further comprising a dichroic mirror for reflecting blue wavelengths of electromagnetic radiation.

Example 55 is a system as in any of Examples 1-54, further comprising a dichroic mirror for reflecting green wavelengths of electromagnetic radiation.

Example 56 is a system as in any of Examples 1-55, further comprising a dichroic mirror for reflecting red wavelengths of electromagnetic radiation.

Example 57 is a system as in any of Examples 1-56, further comprising a dichroic mirror for reflecting electromagnetic radiation having a wavelength from about 513 nm to about 545 nm.

Example 58 is a system as in any of Examples 1-57, further comprising a dichroic mirror for reflecting electromagnetic radiation having a wavelength from about 565 nm to about 585 nm.

Example 59 is a system as in any of Examples 1-58, further comprising a dichroic mirror for reflecting electromagnetic radiation having a wavelength from about 900 nm to about 1000 nm.

Example 60 is a system as in any of Examples 1-59, further comprising a dichroic mirror for reflecting electromagnetic radiation having a wavelength from about 770 nm to about 790 nm.

Example 61 is a system as in any of Examples 1-60, further comprising a dichroic mirror for reflecting electromagnetic radiation having a wavelength from about 795 nm to about 815 nm.

Example 62 is a system as in any of Examples 1-61, further comprising a dichroic mirror for reflecting electromagnetic radiation of a certain band of wavelengths, wherein the dichroic mirror is transparent to electromagnetic radiation of other wavelengths.

Example 63 is a system as in any of Examples 1-62, further comprising a dichroic mirror for reflecting electromagnetic radiation of a certain wavelength, wherein the dichroic mirror is transparent at least to electromagnetic radiation having a red wavelength.

Example 64 is a system as in any of Examples 1-63, further comprising a dichroic mirror for reflecting electromagnetic radiation of a certain wavelength, wherein the dichroic mirror is transparent at least to electromagnetic radiation having a green wavelength.

Example 65 is a system as in any of Examples 1-64, further comprising a dichroic mirror for reflecting electromagnetic radiation of a certain wavelength, wherein the dichroic mirror is transparent at least to electromagnetic radiation having a blue wavelength.

Example 66 is a system as in any of Examples 1-65, further comprising a dichroic mirror for reflecting electromagnetic radiation of a certain wavelength, wherein the dichroic mirror is transparent at least to electromagnetic radiation having a wavelength from about 513 nm to about 545 nm.

Example 67 is a system as in any of Examples 1-66, further comprising a dichroic mirror for reflecting electromagnetic radiation of a certain wavelength, wherein the dichroic mirror is transparent at least to electromagnetic radiation having a wavelength from about 565 nm to about 585 nm.

Example 68 is a system as in any of Examples 1-67, further comprising a dichroic mirror for reflecting electromagnetic radiation of a certain wavelength, wherein the dichroic mirror is transparent at least to electromagnetic radiation having a wavelength from about 900 nm to about 1000 nm.

Example 69 is a system as in any of Examples 1-68, further comprising a dichroic mirror for reflecting electromagnetic radiation of a certain wavelength, wherein the dichroic mirror is transparent at least to electromagnetic radiation having a wavelength from about 770 nm to about 790 nm.

Example 70 is a system as in any of Examples 1-69, further comprising a dichroic mirror for reflecting electromagnetic radiation of a certain wavelength, wherein the dichroic mirror is transparent at least to electromagnetic radiation having a wavelength from about 795 nm to about 815 nm.

Example 71 is a system as in any of Examples 1-70, wherein the emitter comprises a plurality of laser emitters, and wherein the plurality of laser emitters have Gaussian cross-sectional intensity profiles.

Example 72 is a system as in any of Examples 1-71, wherein the emitter comprises a plurality of laser emitters, and wherein the plurality of laser emitter have a flat or approximately flat shaped intensity profile.

Example 73 is a system as in any of Examples 1-72, wherein the emitter comprises a plurality of laser emitters, and wherein the plurality of laser emitters have a top hat shaped intensity profile.

Example 74 is a system as in any of Examples 1-73, wherein the first emitter and the second emitter are aimed at a collection region such that the pulses of the first wavelength of electromagnetic radiation and the pulses of the second wavelength of electromagnetic radiation mix at the collection region and are received by the waveguide.

Example 75 is a system as in any of Examples 1-74, further comprising an intervening optical element disposed between the emitter and the waveguide, wherein the intervening optical element is configured to mix emissions from the first emitter and the second emitter prior to the emission reaching the waveguide.

Example 76 is a system as in any of Examples 1-75, further comprising an intervening optical element disposed between the emitter and the waveguide configured to homogenously mix independent emissions of electromagnetic radiation from the first emitter and the second emitter prior to reaching the waveguide.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
    an emitter for emitting pulses of electromagnetic radiation;
    an endoscope comprising an image sensor, wherein the image sensor comprises a pixel array for sensing reflected electromagnetic radiation;
    a waveguide for communicating the pulses of electromagnetic radiation from the emitter to the endoscope; and
    a controller in electronic communication with the emitter and the image sensor;
    wherein the image sensor captures data for generating a plurality of exposure frames in response to the pulses of electromagnetic radiation by the emitter, and wherein the plurality of exposure frames comprises a laser mapping exposure frame and further comprises two or more of:
        a hyperspectral exposure frame for identifying a spectral response of a tissue, wherein the hyperspectral exposure frame is sensed in response to an emission of electromagnetic radiation having a wavelength from about 513 nm to about 545 nm;
        a hyperspectral exposure frame for identifying a spectral response of a tissue, wherein the hyperspectral exposure frame is sensed in response to an emission of electromagnetic radiation having a wavelength from about 565 nm to about 585 nm;
        a hyperspectral exposure frame for identifying a spectral response of a tissue, wherein the hyperspectral exposure frame is sensed in response to an emission of electromagnetic radiation having a wavelength from about 900 nm to about 1000 nm; or
        a fluorescence exposure frame for identifying a fluorescent reagent, wherein the fluorescence exposure frame is sensed in response to an emission of a fluorescence excitation wavelength; and
    wherein the laser mapping exposure frame comprises data for calculating a three-dimensional topographical map of a scene and is sensed in response to the emitter pulsing a laser mapping pattern.

2. The system of claim 1, wherein:
    the emitter comprises a plurality of emitters disposed within an emitter module;
    the image sensor is located a distal end of a lumen of the endoscope; and
    the waveguide communicates the pulses of electromagnetic radiation from the emitter module to the distal end of the lumen of the endoscope.

3. The system of claim 1, wherein the waveguide comprises one of:
    a single optical fiber; or
    an optical fiber bundle comprising a plurality of optical fibers.

4. The system of claim 1, further comprising a lumen of the endoscope comprising a distal end, and wherein the distal end of the lumen is configured for insertion into a light deficient environment for optical imaging, and wherein:
    the waveguide is an optical fiber bundle comprising a plurality of optical fibers;
    the plurality of optical fibers are disposed within the lumen and terminate at the distal end of the lumen; and
    the plurality of optical fibers are aimed in at least two different directions at the distal end of the lumen such that a light cone generated by the pulses of electromagnetic radiation exiting the plurality of optical fibers has an increased area.

5. The system of claim 1, wherein the waveguide comprises:
    a first portion comprising a plurality of plastic optical fibers;
    a second portion comprising a plurality of glass optical fibers; and
    a connector for connecting the first portion and the second portion such that electromagnetic radiation is communicated from the first portion to the second portion.

6. The system of claim 1, wherein the waveguide comprises an optical diffuser for increasing the area of a light cone generated by the pulses of electromagnetic radiation exiting the waveguide.

7. The system of claim 1, wherein:
    the emitter comprises a plurality of emitters in an emitter module;
    the waveguide comprises a single optical fiber extending from the emitter module to a distal end of a lumen of the endoscope;
    the single optical fiber receives the pulses of electromagnetic radiation at the emitter module; and
    the single optical fiber terminates at the distal end of the lumen such that the pulses of electromagnetic radiation illuminate a scene located at the distal end of the lumen.

8. The system of claim 1, further comprising a lumen of the endoscope, wherein the lumen comprises:
    an inner cavity defined by an inner cylinder for receiving optical components of the endoscope; and
    a peripheral cavity defined by the inner cylinder and an outer cylinder for receiving the waveguide.

9. The system of claim 1, wherein:
    the waveguide comprises an optical fiber bundle comprising a plurality of plastic optical fibers, wherein the emitter emits the pulses of electromagnetic radiation into the optical fiber bundle;
    the waveguide further comprises an intervening optical component, wherein the pulses of electromagnetic radiation pass through the intervening optical component before entering the optical fiber bundle; and
    the intervening optical component comprises a plurality of glass optical fibers.

10. The system of claim 1, wherein the waveguide comprises:
    an optical fiber bundle, wherein the emitter emits the pulses of electromagnetic radiation into the optical fiber bundle; and
    a diffuser disposed at a distal end of the optical fiber bundle;

wherein the diffuser provides a light cone having a field of view angle between 110 degrees and 120 degrees.

11. The system of claim 1, wherein the waveguide comprises:
a single optical fiber, wherein the emitter emits the pulses of electromagnetic radiation into the single optical fiber; and
a diffuser disposed at a distal end of the single optical fiber;
wherein the diffuser provides a light cone having a field of view angle between 110 degrees and 120 degrees.

12. The system of claim 1, wherein each of the plurality of exposure frames corresponds to one or more pulses of electromagnetic radiation emitted by the emitter, and wherein the plurality of exposure frames further comprises:
a red exposure frame sensed in response to an emission of red electromagnetic radiation;
a green exposure frame sensed in response to an emission of green electromagnetic radiation; and
a blue exposure frame sensed in response to an emission of blue electromagnetic radiation.

13. The system of claim 12, wherein the pixel array of the image sensor senses reflected electromagnetic radiation to generate the plurality of exposure frames during readout periods of the pixel array, wherein a readout period comprises a duration of time when active pixels in the pixel array are read, and wherein a single exposure frame corresponds with a single readout period of the pixel array.

14. The system of claim 1, wherein the emitter is configured to emit, during a pulse duration, a plurality of sub-pulses of electromagnetic radiation having a sub-duration shorter than the pulse duration.

15. The system of claim 1, wherein one or more of the pulses of electromagnetic radiation emitted by the emitter comprises electromagnetic radiation emitted at two or more wavelengths simultaneously as a single pulse or a single sub-pulse.

16. The system of claim 1, wherein the controller is configured to provide the fluorescence exposure frame to a corresponding fluorescence system that determines a location of a tissue structure within the scene based on the fluorescence exposure frame.

17. The system of claim 16, wherein the fluorescence excitation emission comprises one or more of:
electromagnetic radiation having a wavelength from about 770 nm to about 790 nm; or
electromagnetic radiation having the wavelength from about 795 nm to about 815 nm.

18. The system of claim 17, wherein the controller is further configured to:
receive the location of the tissue structure from the corresponding fluorescence system;
generate an overlay frame comprising the location of the tissue structure; and
combine the overlay frame with a color image frame depicting the scene to indicate the location of the tissue structure within the scene.

19. The system of claim 18, wherein the controller is configured to:
provide the laser mapping exposure frame to a corresponding laser mapping system that calculates the three-dimensional topographical map based on the laser mapping exposure frame;
provide the location of the critical tissue structure to the corresponding laser mapping system; and receive a three-dimensional topology and/or dimension of the tissue structure from the corresponding laser mapping system.

20. The system of claim 19, wherein the tissue structure comprises one or more of a nerve, a ureter, a blood vessel, an artery, a blood flow, or a tumor.

21. The system of claim 1, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

22. The system of claim 1, wherein two or more pulses of electromagnetic radiation emitted by the emitter result in two or more instances of reflected electromagnetic radiation that are sensed by the pixel array to generate two or more exposure frames that are combined to form an image frame.

23. The system of claim 1, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the plurality of exposure frames corresponds to one or more pulses of electromagnetic radiation.

24. The system of claim 1, wherein the pulses of electromagnetic radiation are emitted in a pattern of varying wavelengths of electromagnetic radiation, and wherein the emitter repeats the pattern of varying wavelengths of electromagnetic radiation.

25. The system of claim 1, wherein the laser mapping exposure frame comprises information for determining real time measurements comprising one or more of:
a distance from the endoscope to an object;
an angle between the endoscope and the object; or
three-dimensional surface topology information about the object.

26. The system of claim 1, wherein at least a portion of the pulses of electromagnetic radiation emitted by the emitter comprises a plurality of tool-specific laser mapping patterns for each of a plurality of tools within a scene.

27. The system of claim 1, wherein the laser mapping pattern emitted by the emitter comprises a first output and a second output that are independent from one another, wherein the first output is for light illumination and the second output is for tool tracking, and wherein the laser mapping pattern comprises one or more of a raster grid of discrete points, an occupancy grid map, or a dot array.

28. The system of claim 1, wherein the controller is configured to provide the hyperspectral exposure frame to a corresponding hyperspectral system that determines a location of a tissue structure within a scene based on the hyperspectral exposure frame.

29. The system of claim 28, wherein the hyperspectral emission comprises:
the electromagnetic radiation having the wavelength from about 513 nm to about 545 nm and the electromagnetic radiation having the wavelength from about 900 nm to about 1000 nm; or
the electromagnetic radiation having the wavelength from about 565 nm to about 585 nm and the electromagnetic radiation having the wavelength from about 900 nm to about 1000 nm.

30. The system of claim 29, wherein the controller is further configured to:
- receive the location of the tissue structure from the corresponding hyperspectral system;
- generate an overlay frame comprising the location of the tissue structure; and
- combine the overlay frame with a color image frame depicting the scene to indicate the location of the tissue structure within the scene.

31. The system of claim 30, wherein the controller is further configured to:
- provide the laser mapping exposure frame to a corresponding laser mapping system that calculates the three-dimensional topographical map of the scene based on the laser mapping exposure frame;
- provide the location of the tissue structure to the corresponding laser mapping system; and
- receive a three-dimensional topographical map and/or dimension of the tissue structure from the corresponding laser mapping system.

32. The system of claim 31, wherein the tissue structure comprises one or more of a nerve, a ureter, a blood vessel, an artery, a blood flow, or a tumor.

\* \* \* \* \*